United States Patent
Chain et al.

(10) Patent No.: US 9,676,788 B2
(45) Date of Patent: Jun. 13, 2017

(54) AZA-EPOXY-GUAIANE DERIVATIVES AND TREATMENT OF CANCER

(71) Applicants: The United States of America, as represented by the Secretary, Department of Health and Human Services, Washington, DC (US); University of Hawaii, Honolulu, HI (US)

(72) Inventors: William J. Chain, Honolulu, HI (US); John A. Beutler, Union Bridge, MD (US); David Fash, Honolulu, HI (US); William D. Figg, Fairfax, VA (US); Zhenwu Li, West Haven, CT (US); Cody John Peer, Frederick, MD (US); Joe William Ramos, Honolulu, HI (US); Florian J. Sulzmaier, San Diego, CA (US)

(73) Assignees: The United States of America, as represented by the Secretary of Health and Human Services, Washington, DC (US); University of Hawaii, Honolulu, HI (US)

( * ) Notice: Subject to any disclaimer, the term of this patent is extended or adjusted under 35 U.S.C. 154(b) by 0 days.

(21) Appl. No.: 15/116,887

(22) PCT Filed: Feb. 5, 2015

(86) PCT No.: PCT/US2015/014601
§ 371 (c)(1),
(2) Date: Aug. 5, 2016

(87) PCT Pub. No.: WO2015/120140
PCT Pub. Date: Aug. 13, 2015

(65) Prior Publication Data
US 2016/0347764 A1    Dec. 1, 2016

Related U.S. Application Data

(60) Provisional application No. 62/018,381, filed on Jun. 27, 2014, provisional application No. 61/936,285, filed on Feb. 5, 2014.

(51) Int. Cl.
*C07D 493/08* (2006.01)
*A61K 9/00* (2006.01)
*A61K 45/06* (2006.01)
*A61K 31/352* (2006.01)

(52) U.S. Cl.
CPC .......... *C07D 493/08* (2013.01); *A61K 9/0053* (2013.01); *A61K 31/352* (2013.01); *A61K 45/06* (2013.01)

(58) Field of Classification Search
None
See application file for complete search history.

(56) References Cited

U.S. PATENT DOCUMENTS 8,410,292 B2 *   4/2013   Beutler ................ C07D 493/08
                                                  540/581
2010/0286259 A1   11/2010  Beutler et al.

FOREIGN PATENT DOCUMENTS

| EP | 2474550 A1 | 7/2012 |
| WO | WO 2009/088854 A1 | 7/2009 |
| WO | WO 2011/120886 A1 | 10/2011 |
| WO | WO 2012/084267 A1 | 6/2012 |
| WO | WO 2013/106226 A1 | 7/2013 |
| WO | WO 2014/078350 A1 | 5/2014 |

OTHER PUBLICATIONS

Akee et al., "Chlorinated Englerins with Selective Inhibition of Renal Cancer Cell Growth" *Journal of Natural Products* 75(3) 459-463 (2012).
Chan et al., "Chemical Synthesis and Biological Evaluation of the Englerin Analogues", *ChemMedChem, Wiley—VCH Verlag.*, 6 (3) 420-423 (Mar. 7, 2011).
Chain et al., "Synthetic Strategies toward the Guaiane Sesquiterpene Englerin A" *Synlett* 2605-2608 (2011).
(Continued)

*Primary Examiner* — Brian J Davis
(74) *Attorney, Agent, or Firm* — Leydig, Voit & Mayer, Ltd.

(57) ABSTRACT

Disclosed is a compound of formula (I) or formula (II): (Formulas should be inserted here) wherein $R^1$-$R^6$ are as defined herein. Also disclosed are a pharmaceutical composition comprising such a compound and a method of treating or preventing cancer in a mammal in need thereof, comprising administering to the mammal a compound of formula (I) or formula (II).

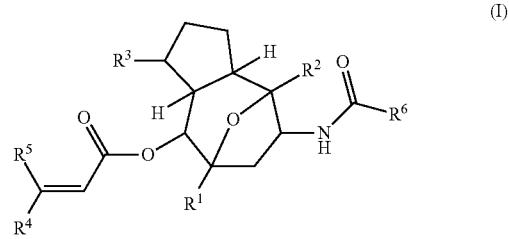

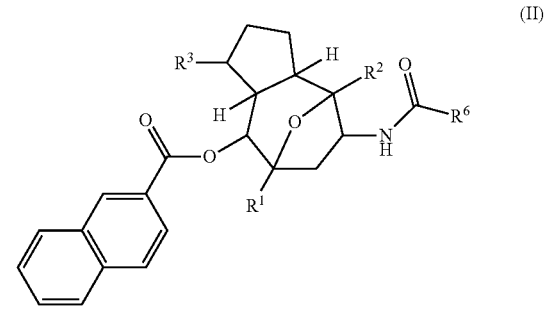

20 Claims, 21 Drawing Sheets

(56) References Cited

OTHER PUBLICATIONS

Currie et al., "Heat-shock response is associated with enhanced postischemic ventricular recovery", *Cir. Res.* 63, 395-397 (1988).
European Patent Office, International Search Report in International Patent Application No. PCT/US2015/014601, 5 pages, Mar. 20, 2015.
European Patent Office, Written Opinion of the International Searching Authority in International Patent Application No. PCT/US2015/014601, 6 pages, Mar. 20, 2015.
European Patent Office, International Preliminary Report on Patentability in International Patent Application No. PCT/US2015/014601, 7 pages, Mar. 20, 2015.
Kavanagh et al., "Restoring HSP70 deficiencies improves glucose tolerance in diabetic monkeys," *Am. J. Physiol. Endocrinol. Metab.*, 300 (5), E894-E901 (2011).
Lee et al., "A Formal Synthesis of (−)-Englerin A by Relay Ring Closing Metathesis and Transannular Etherification" *Organic Letters*, 14(11) 2682-2685 (2012).
Li et al., "A brief synthesis of (−)-englerin A," *J. Am. Chem. Soc.*, 133 (17), 6553-6556 (2011).
Molawi et al., "Enantioselective Synthesis of (−)-Englerins A and B" *Angew. Chem. Int. Ed.*49 (20) 3517-3519 (2010).
Nicolaou et al., "Total Synthesis of Englerin A" *Journal of the American Chemical Society, American Chemical Society*, 132 (23) 8219-8222 (May 24, 2010).
Pouwer et al. "Chemical Synthesis of the Englerins" *Chem. Asian J.*7, 22-35 (2012).
Radtke, et al., "Total Synthesis and Biological Evaluation of (−)-Englerin 14;A and B: Synthesis of Analogues with Improved Activity Profile", *Angewandte Chemie International Edition*, 50 (17) 3998-4002 (Apr. 18, 2011).
Ratnayake et al., "Englerin A, a Selective Inhibitor of Renal Cancer Cell Growth, from Phyllanthus engleri" *Organic Letters, American Chemical Society*, US, 11 (1) 57-60 (2008; Jan. 1, 2009).

Sourbier et al., "Englerin A Stimulates PKC0 to Inhibit Insulin Signaling and to Simultaneously Activate HSF1: Pharmacologically Induced Synthetic Lethality", *Cancer Cell* 23 (228) 2013.
Sulzmaier et al., "Englerin A selectively induces necrosis in human renal cancer cells." *PLoS ONE*, 7 e48032 (2012).
Szostak et al., "Concise Syntheses of Strychnine and Englerin A: the Power of Reductive Cyclizations Triggered by Samarium Iodide" *Angewandte Chemie, International Edition* 50(34) 7737-7739 (2011).
Takahashi et al., "Stereocontrolled Total Synthesis of (−)-Englerin A" *Journal of Organic Chemistry*, 77(17) 7364-7370 (2012).
Ushakov, et al. "Total Synthesis and Biological Evaluation of (−)-9-Deoxy-englerin A " *Org. Lett.* 13, 2090-2093 (2011).
Wang et al., "Collective Total Synthesis of Englerin A and B, Orientalol E and F, and Oxyphyllol: Application of the Organocatalytic [4+3] Cycloaddition Reaction" *Chemistry—A European Journal*, 19(7) 2539-2547 (2013).
Wang et al., "Concise formal synthesis of (+)-englerin A and total synthesis of (−)-orientalol F: establishment of the stereochemistry of the organocatalytic [4+3]-cycloaddition reaction" *Synlett*, 23(2) 263-266 (2012).
Willot et al., "Totasl Synthesis and Absolute Configuration of the Guaiane Sesquiterpene Englerin A" *Angew. Chem. Int. Ed.* 48 (48) 9105-9108 (2009).
Xu et al., "Enantioselective Formal Synthesis of (−)-Englerin A via a Rh-Catalyzed [4+3] Cycloaddition Reaction" *Org. Lett.* 12, 3708-3711 (2010).
Xu et al., "Formal Synthesis of (−)-Englerin A and Cytotoxicity Studies of Truncated Englerins" *Chemistry—An Asian Journal*, 7(5) 1052-1060 (2012).
Zahel et al., "A Short Enantioselective Total Synthesis of (−)-Englerin A" *Angewandte Chemie, International Edition*, 52(20) 5390-5392 (2013).
Zhang et al., "Total synthesis of (−)-Englerin A" *Tetrahedron Letters* 55(7), 1339-1341 (2014).
Zhou at al., "Asymmetric, Protecting-Group-Free Total Synthesis of (−)-Englerin A" *Angew. Chem. Int. Ed.* 49, 3513-3516 (2010).

\* cited by examiner

9

10

11

12

31

AZA-EPOXY-GUAIANE DERIVATIVES AND TREATMENT OF CANCER

CROSS-REFERENCE TO RELATED APPLICATIONS

This patent application is a U.S. National Phase of International Patent Application No. PCT/US2015/014601, filed Feb. 5, 2015, which claims the benefit of U.S. Provisional Patent Applications Nos. 61/936,285, filed Feb. 5, 2014, and 62/018,381, filed Jun. 27, 2014, which are incorporated by reference for all purposes.

BACKGROUND OF THE INVENTION

Cancer is a major cause of death; for example, renal cancer is an important contributor to morbidity and mortality. Attempts have been made to identify and isolate medicinal products for cancer treatment from plant materials. For example, certain *Phyllanthus* species have been found in tropical and subtropical regions of the world and used in traditional medicines. For example, certain epoxy guaianes and derivatives have been proposed; see, e.g., WO 2009/088854 A1.

Nevertheless, there is a desire to identify or produce new treatments for cancer, particularly renal cancer.

BRIEF SUMMARY OF THE INVENTION

The invention provides aza-epoxy guaiane derivatives. Thus, the invention provides a compound of formula (I) or formula (II):

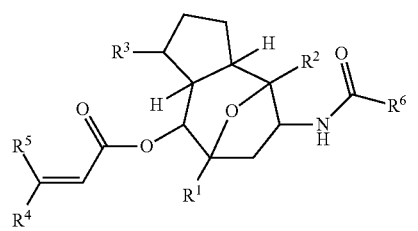

(I)

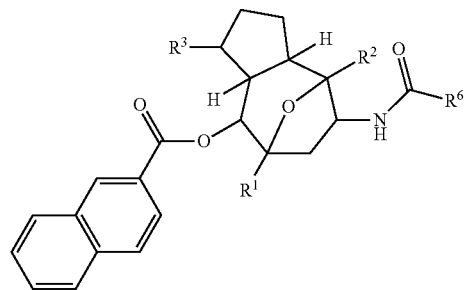

(II)

or an epimer thereof, wherein
$R^1$ is isopropyl or isopropylenyl,
$R^2$ and $R^3$ are independently $C_1$-$C_6$ alkyl,
$R^4$ is $C_6$-$C_{10}$ aryl or $C_3$-$C_8$ cycloalkyl, wherein the aryl is optionally substituted with $C_1$-$C_6$ alkyl, $C_1$-$C_6$ hydroxyalkyl, $C_1$-$C_6$ alkoxy, halo, or nitro,
$R^5$ is hydrogen or $C_1$-$C_6$ alkyl, and
$R^6$ is $C_1$-$C_6$ alkyl, hydroxy $C_1$-$C_6$ alkyl, or fluoro $C_1$-$C_6$ alkyl.

The invention also provides a pharmaceutical composition comprising a pharmaceutically acceptable carrier and a compound of the invention.

The invention further provides a method of treating cancer in a mammal comprising administering to the animal an effective amount of a compound of formula (I) or formula (II):

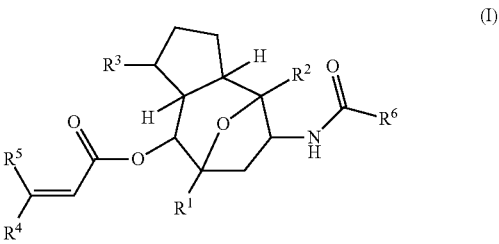

(I)

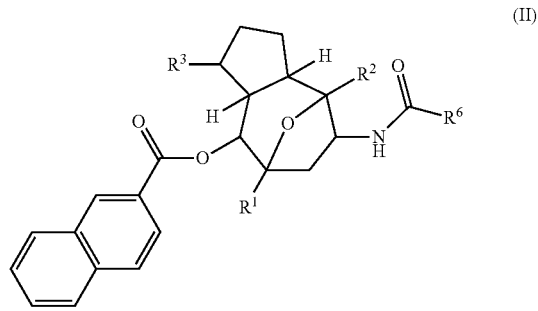

(II)

or an epimer thereof, wherein
$R^1$ is isopropyl or isopropylenyl,
$R^2$ and $R^3$ are independently $C_1$-$C_6$ alkyl,
$R^4$ is $C_6$-$C_{10}$ aryl or $C_3$-$C_8$ cycloalkyl, wherein the aryl is optionally substituted with $C_1$-$C_6$ alkyl, $C_1$-$C_6$ hydroxyalkyl, $C_1$-$C_6$ alkoxy, halo, or nitro,
$R^5$ is hydrogen or $C_1$-$C_6$ alkyl, and
$R^6$ is $C_1$-$C_6$ alkyl, hydroxy $C_1$-$C_6$ alkyl, or fluoro $C_1$-$C_6$ alkyl.

The compounds of the invention advantageously exhibit oral bioavailability and sufficient stability to thereby allow for oral administration of the compounds to a mammal in need thereof.

BRIEF DESCRIPTION OF THE SEVERAL VIEWS OF THE DRAWING(S)

FIGS. 1A-1I depict the dose response curves for compound 9 against various cancer cell lines in a 60-cell test. FIG. 1A depicts the dose response curves against leukemia cell lines. FIG. 1B depicts the dose response curves against non-small cell lung cancer cell lines. FIG. 1C depicts the dose response curves against colon cancer cell lines. FIG. 1D depicts dose response curves against CNS cancer cell lines. FIG. 1E depicts dose response curves against melanoma cell lines. FIG. 1F depicts dose response curves against ovarian cancer cell lines. FIG. 1G depicts does response curves against renal cancer cell lines. FIG. 1H depicts dose response curves against prostate cancer cell lines. FIG. 1I depicts dose response curves against breast cancer cell lines.

FIGS. 2A-2I depict the dose response curves for compound 12 against various cancer cell lines in a 60-cell test. FIG. 2A depicts the dose response curves against leukemia cell lines. FIG. 2B depicts the dose response curves against non-small cell lung cancer cell lines. FIG. 2C depicts the dose response curves against colon cancer cell lines. FIG. 2D depicts dose response curves against CNS cancer cell lines. FIG. 2E depicts dose response curves against melanoma cell lines. FIG. 2F depicts dose response curves against ovarian cancer cell lines. FIG. 2G depicts does response curves against renal cancer cell lines. FIG. 2H depicts dose response curves against prostate cancer cell lines. FIG. 2I depicts dose response curves against breast cancer cell lines.

FIGS. 3A-3I depict the dose response curves for compound 11 against various cancer cell lines in a 60-cell test. FIG. 3A depicts the dose response curves against leukemia cell lines. FIG. 3B depicts the dose response curves against non-small cell lung cancer cell lines. FIG. 3C depicts the dose response curves against colon cancer cell lines. FIG. 3D depicts dose response curves against CNS cancer cell lines. FIG. 3E depicts dose response curves against melanoma cell lines. FIG. 3F depicts dose response curves against ovarian cancer cell lines. FIG. 3G depicts does response curves against renal cancer cell lines. FIG. 3H depicts dose response curves against prostate cancer cell lines. FIG. 3I depicts dose response curves against breast cancer cell lines.

FIGS. 4A-3I depict the dose response curves for compound 10 against various cancer cell lines in a 60-cell test. FIG. 4A depicts the dose response curves against leukemia cell lines. FIG. 4B depicts the dose response curves against non-small cell lung cancer cell lines. FIG. 4C depicts the dose response curves against colon cancer cell lines. FIG. 4D depicts dose response curves against CNS cancer cell lines. FIG. 4E depicts dose response curves against melanoma cell lines. FIG. 4F depicts dose response curves against ovarian cancer cell lines. FIG. 4G depicts does response curves against renal cancer cell lines. FIG. 4H depicts dose response curves against prostate cancer cell lines. FIG. 4I depicts dose response curves against breast cancer cell lines.

DETAILED DESCRIPTION OF THE INVENTION

Figure 1A:
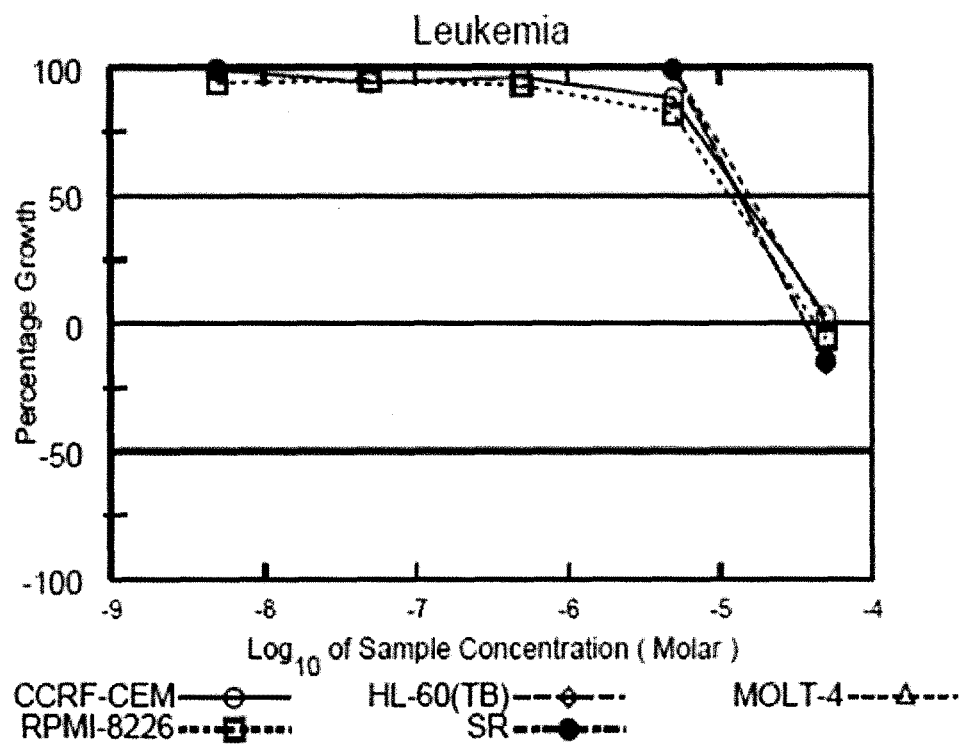
Figure 1B:
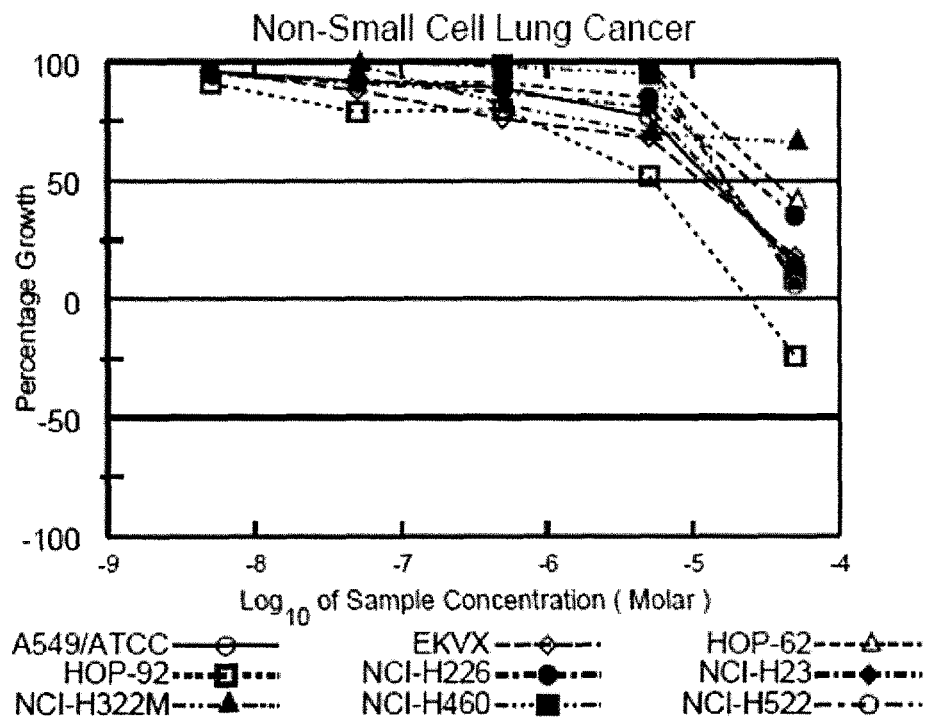
Figure 1C:
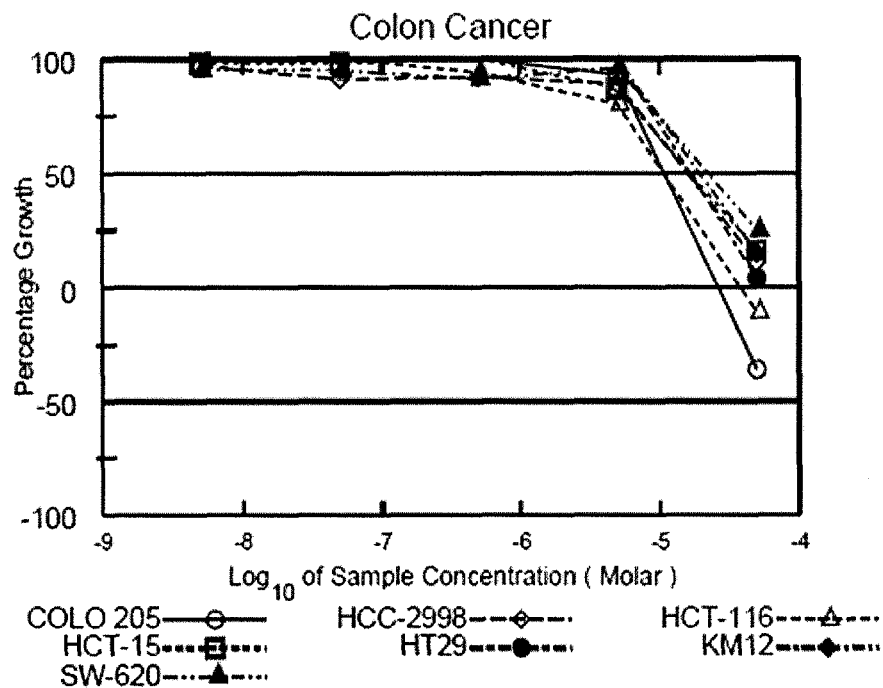
Figure 1D:
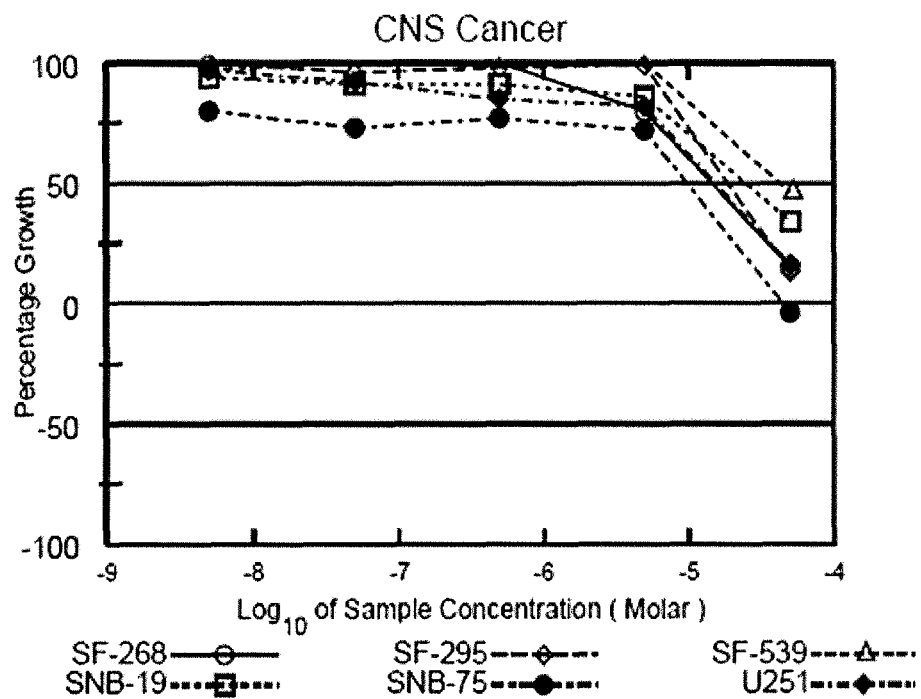
Figure 1E:
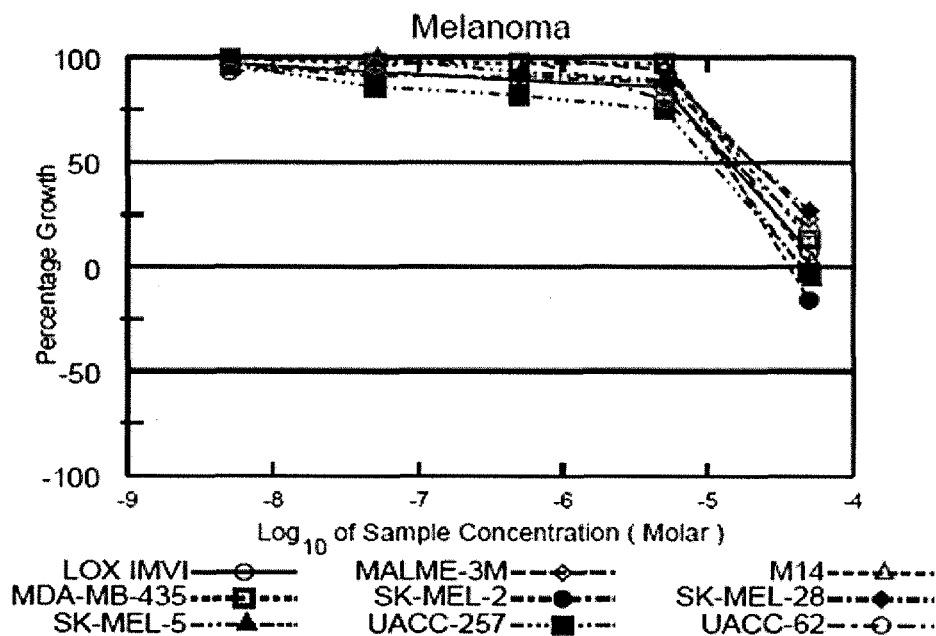
Figure 1F:
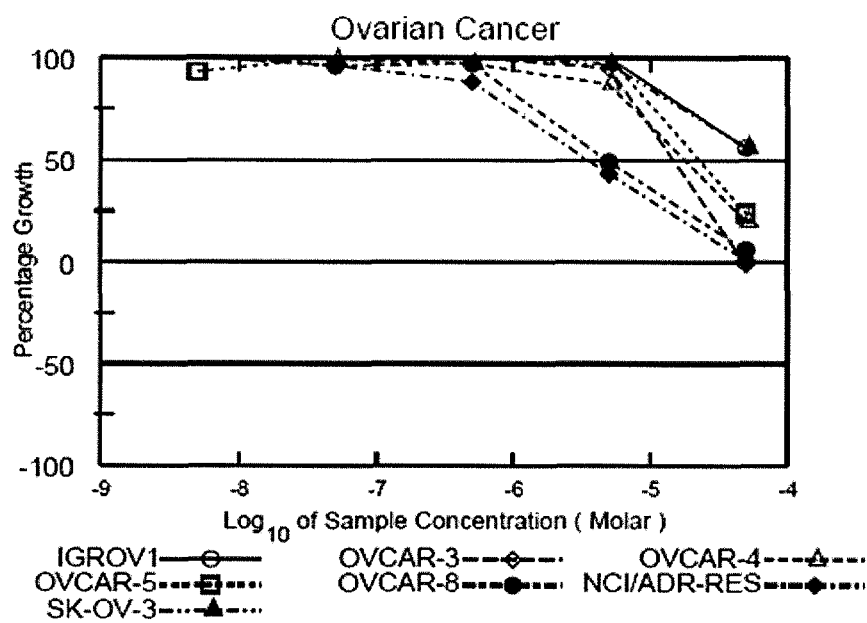
Figure 1G:
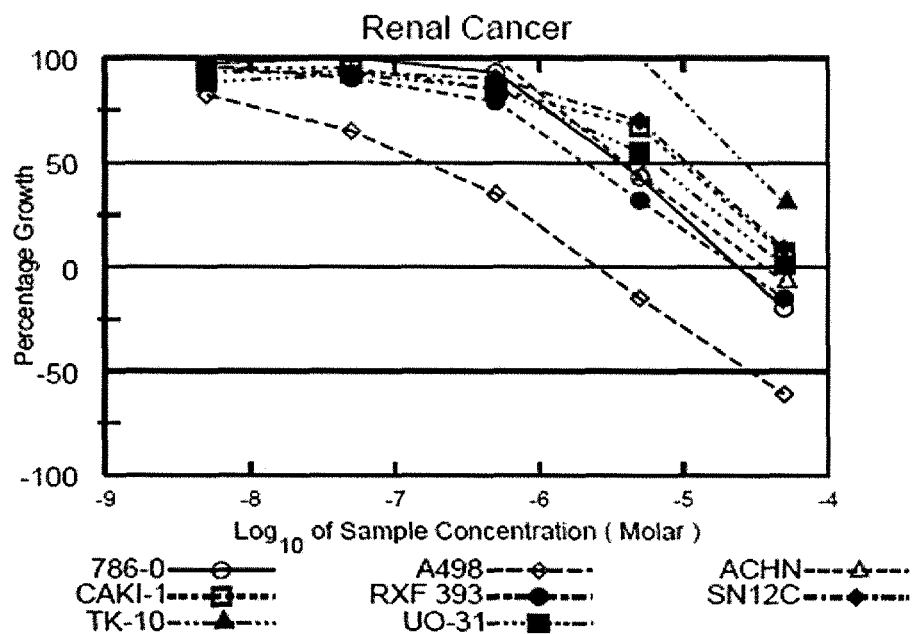
Figure 1H:
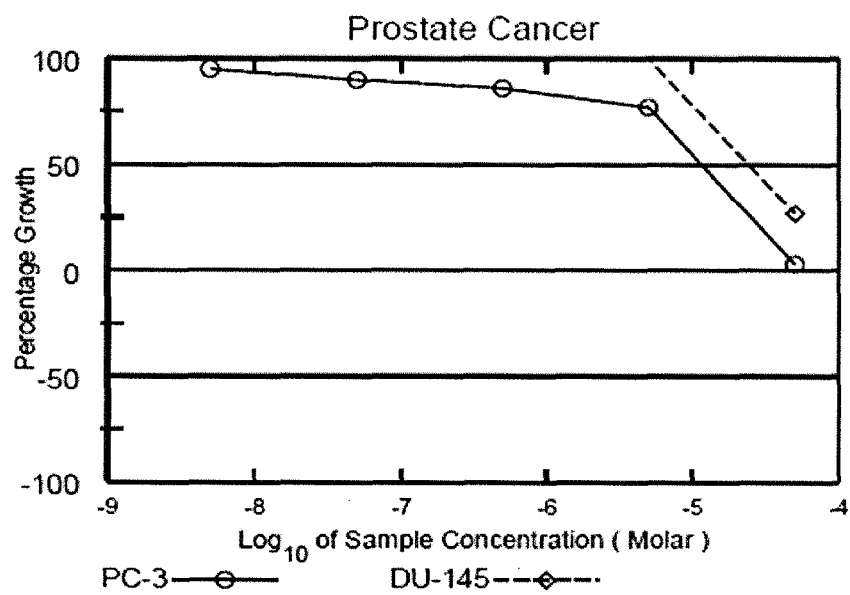
Figure 1I:
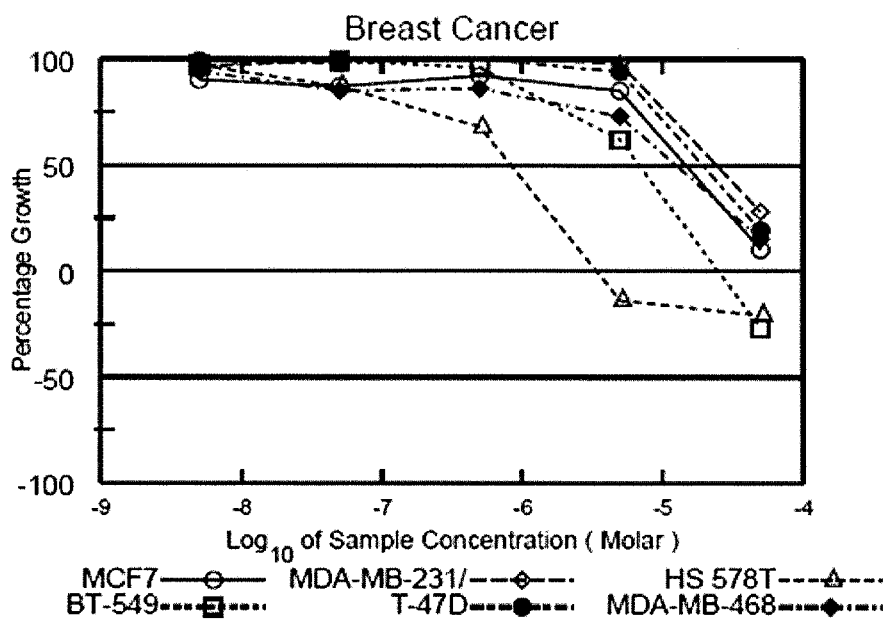
Figure 2A:
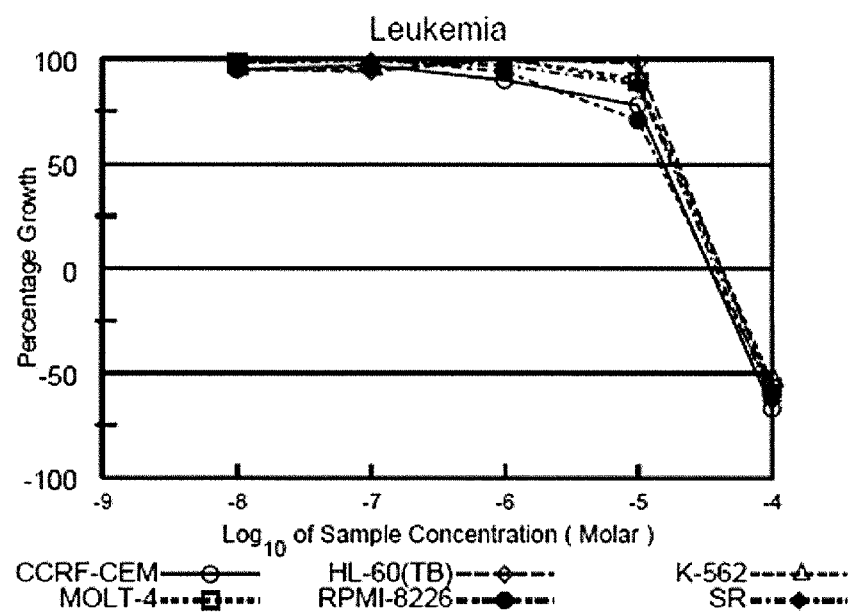
Figure 2B:
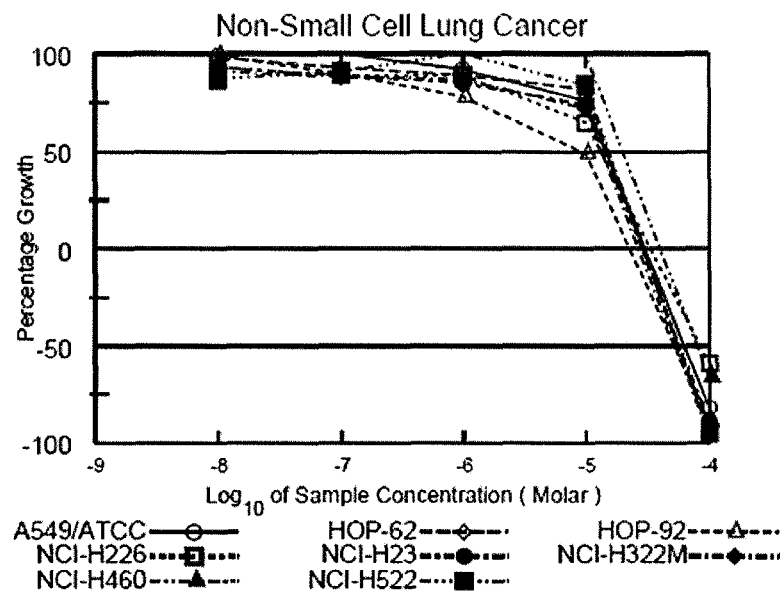
Figure 2C:
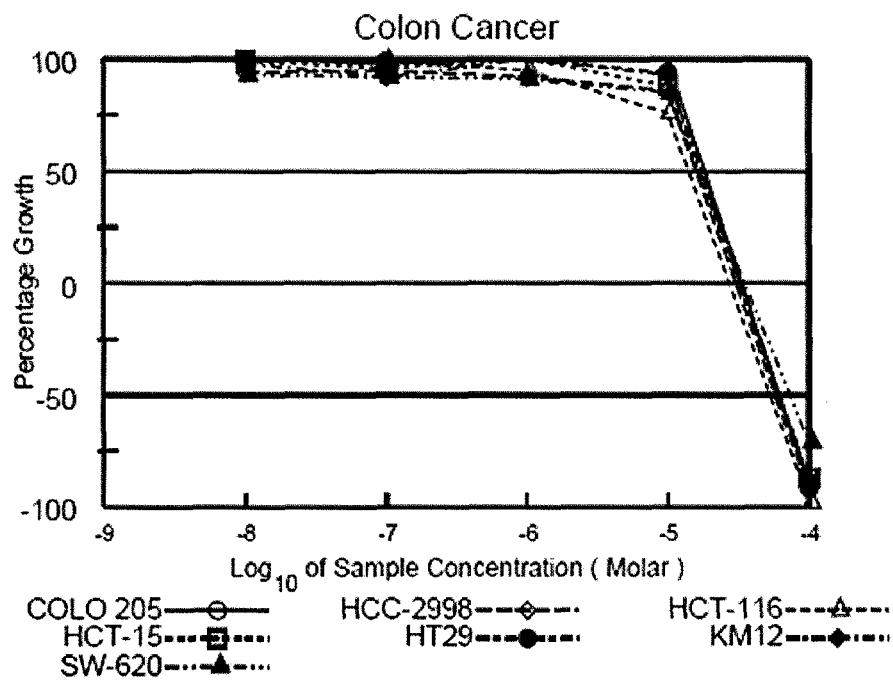
Figure 2D:
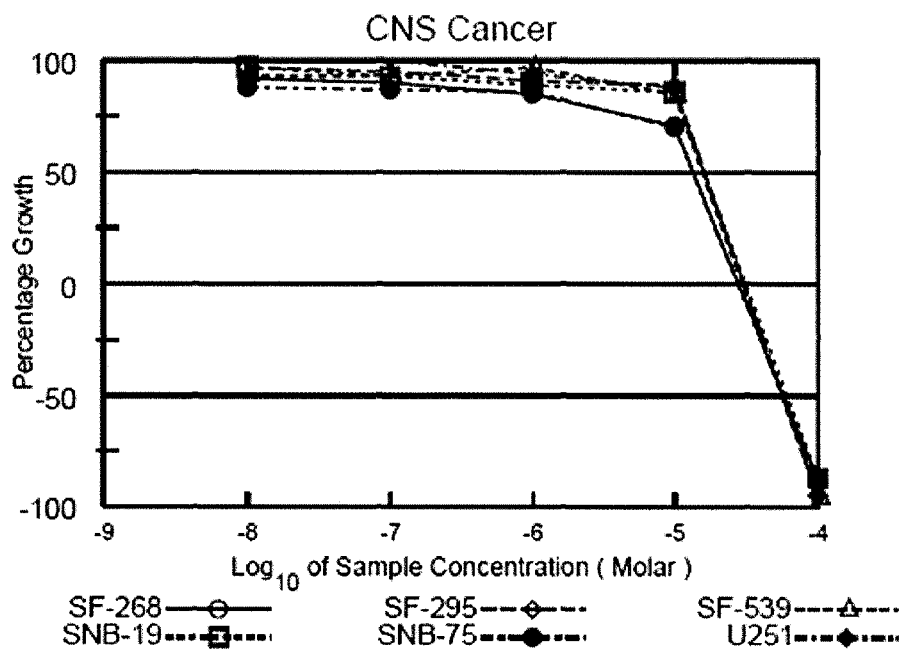
Figure 2E:
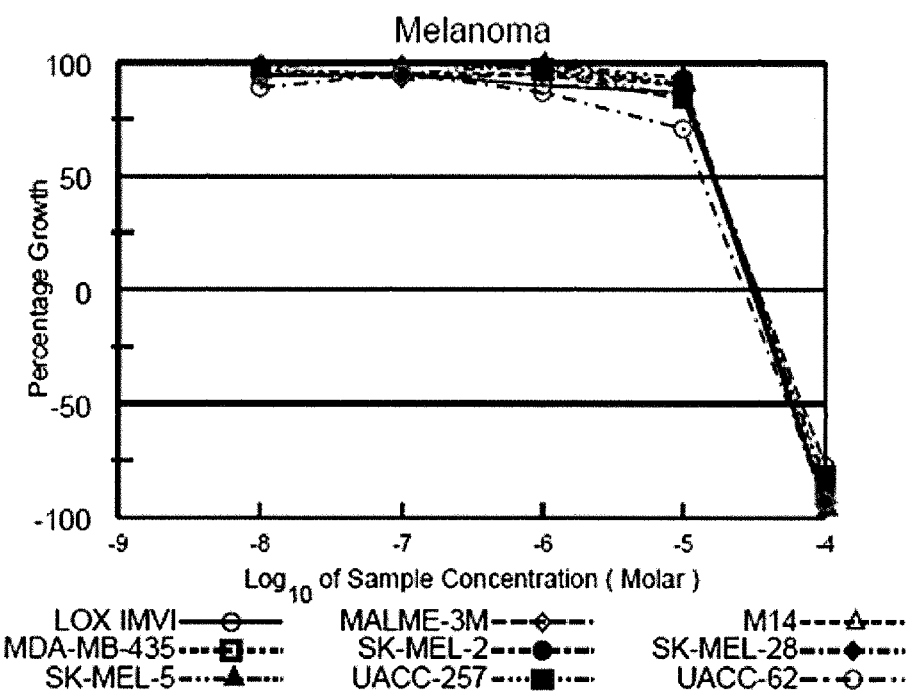
Figure 2F:
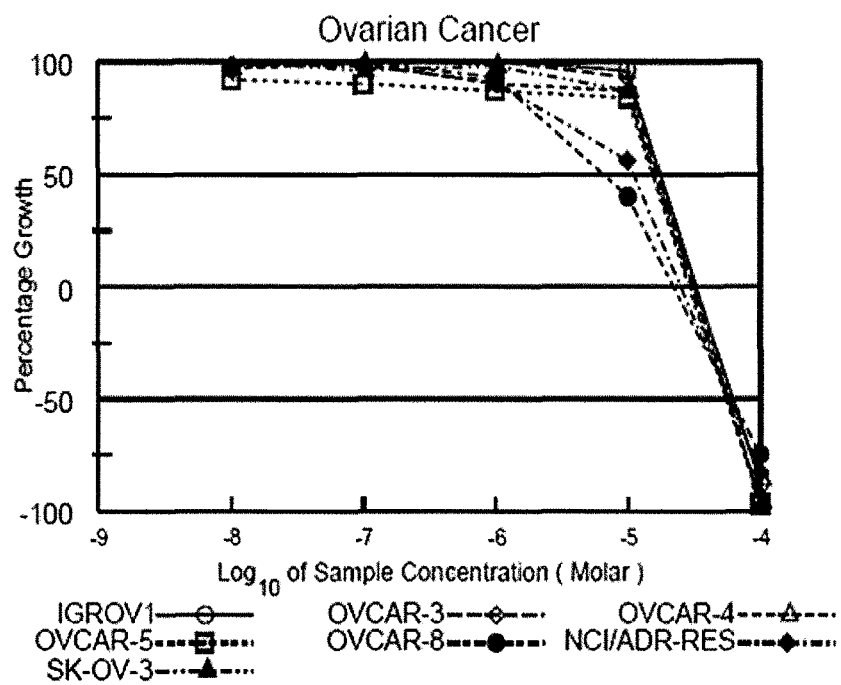
Figure 2G:
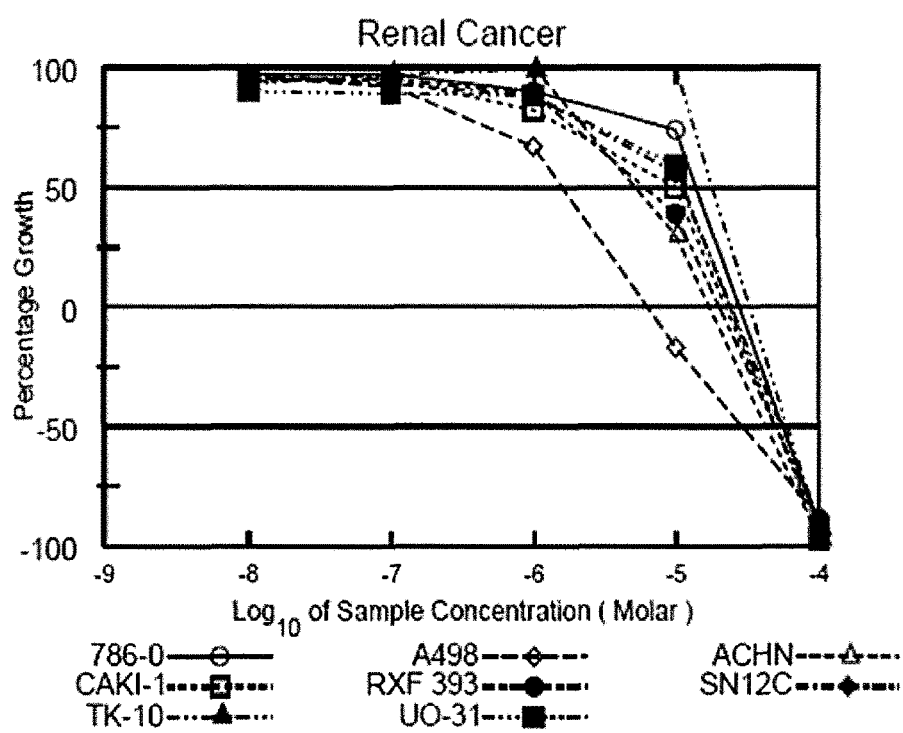
Figure 2H:
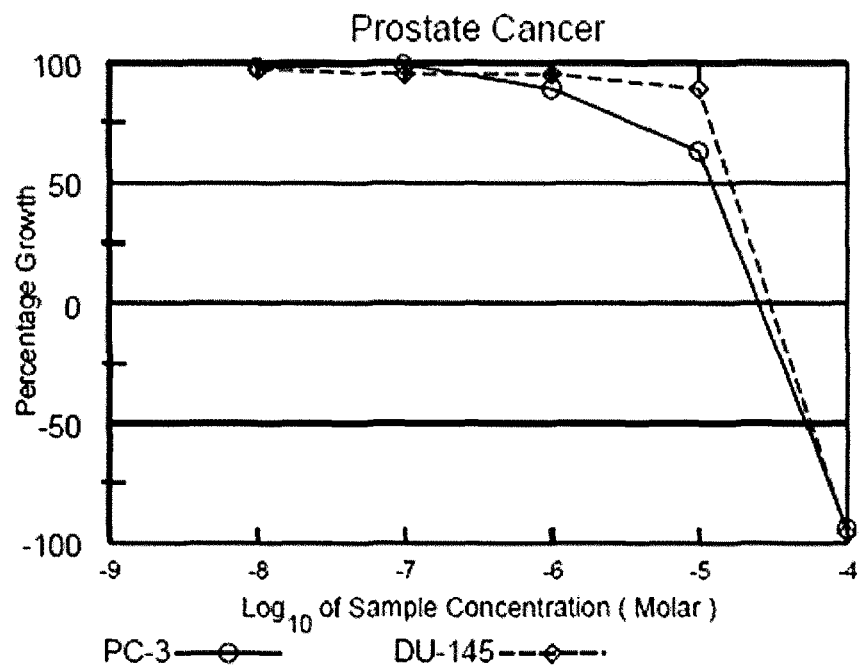
Figure 2I:
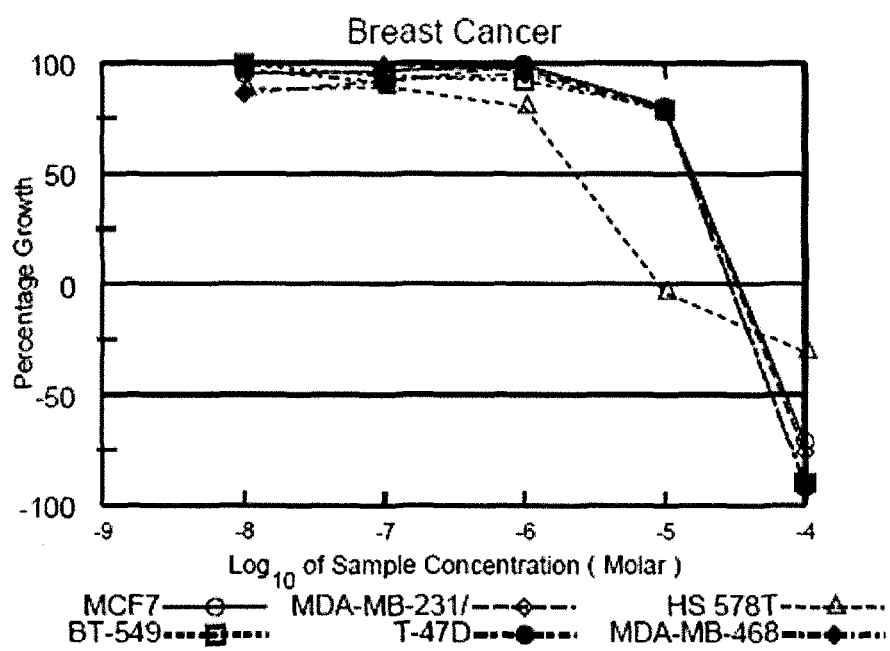

The invention provides a compound of formula (I) or formula (II):

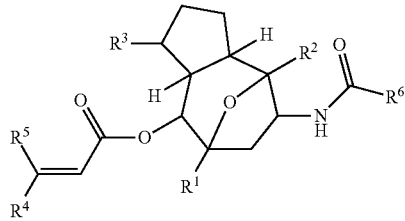

(I)

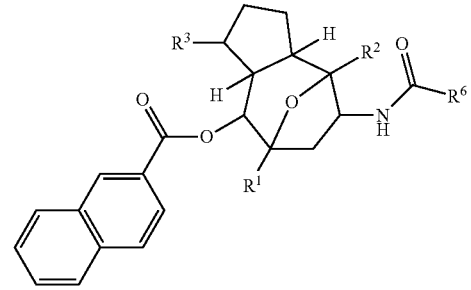

(II)

or an epimer thereof, wherein
$R^1$ is isopropyl or isopropylenyl,
$R^2$ and $R^3$ are independently $C_1$-$C_6$ alkyl,
$R^4$ is $C_6$-$C_{10}$ aryl or $C_3$-$C_8$ cycloalkyl, wherein the aryl is optionally substituted with $C_1$-$C_6$ alkyl, $C_1$-$C_6$ hydroxyalkyl, $C_1$-$C_6$ alkoxy, halo, or nitro,
$R^5$ is hydrogen or $C_1$-$C_6$ alkyl, and
$R^6$ is $C_1$-$C_6$ alkyl, hydroxy $C_1$-$C_6$ alkyl, or fluoro $C_1$-$C_6$ alkyl.

In certain embodiments, $R^2$ and $R^3$ are methyl.
In an embodiment, the compound is of formula (I).
In any of the above embodiments, $R^6$ is hydroxy $C_1$-$C_6$ alkyl or fluoro $C_1$-$C_6$ alkyl.

In certain preferred embodiments, the compound is

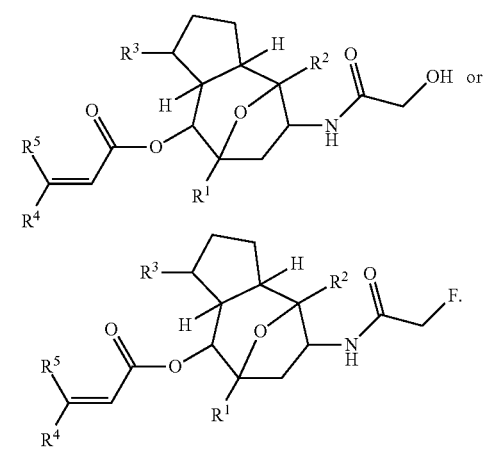

In any of the above embodiments, $R^4$ is $C_6$-$C_{10}$ aryl.
In certain embodiments, $R^4$ is phenyl.
In any of the above embodiments, $R^5$ is hydrogen or methyl.

In certain particular embodiments, the compound is

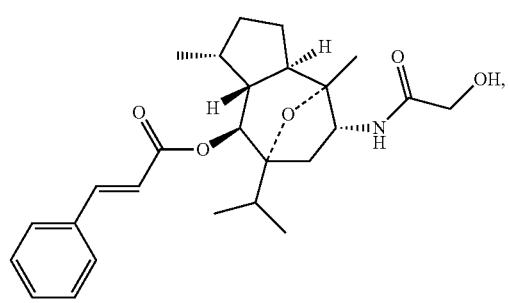

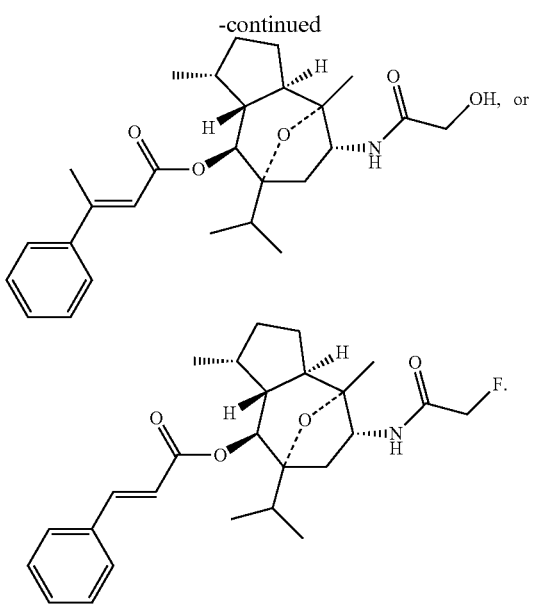

In certain embodiments of formula (I) or formula (II), $R^4$ is $C_3$-$C_8$ cycloalkyl.

In any of the above embodiments, $R^5$ is hydrogen.

In a particular embodiment, the compound is

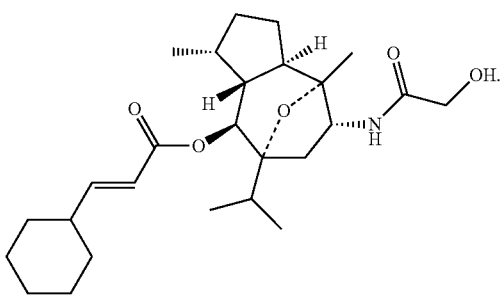 [SMILES: CC(C)[C@@]12C[C@@H](NC(=O)CO)[C@@](C)(O1)[C@@H]1CC[C@@H](C)[C@H]1[C@@H]2OC(=O)/C=C/C1CCCCC1]

In certain embodiments, the compound is of formula (II).

In certain of these embodiments, $R^6$ is hydroxy $C_1$-$C_6$ alkyl or fluoro $C_1$-$C_6$ alkyl.

In a particular embodiment, the compound is

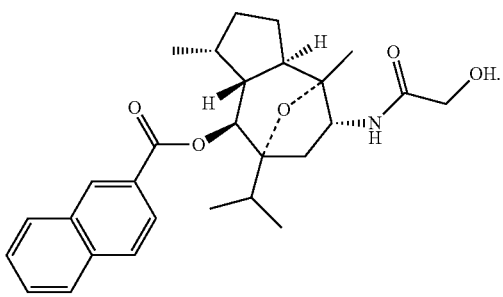 [SMILES: CC(C)[C@@]12C[C@@H](NC(=O)CO)[C@@](C)(O1)[C@@H]1CC[C@@H](C)[C@H]1[C@@H]2OC(=O)c1ccc2ccccc2c1]

The compounds of formula (I) and formula (II) can be prepared by any suitable synthetic methodology. For example, in a embodiment, as depicted below, compound 100 can be prepared based on the procedure described in Z. Li et al., *J. Am. Chem. Soc.,* 2011, 133(17): 6553-6556. Compound 100 can be acylated using any suitable acylating agent, for example, an acid chloride, acid anhydride, mixed anhydride, carboxylic acid, and the like, in the presence of a base, for example triethylamine, dimethylaminopyridine, mixtures thereof, and the like, or in the presence of a condensing agent, for example, dicyclohexylcarbodiimide, N-(3-dimethylaminopropyl)-N-ethylcarbodiimide hydrochloride, HATU, and the like, in any suitable solvent, for example, dichloromethane, pyridine, and the like, to provide compound 101. The carbonyl group of compound 101 can be reduced using any suitable reducing agent, for example, sodium borohydride and the like, in a suitable solvent, for example methanol and the like, to provide compound 102. The hydroxyl group of compound 102 can be converted into a suitable leaving group ("OL"), for example, an imidazole-sulfonyl group, methanesulfonyl group, p-toluenesulfonyl group, and the like, by reacting compound 102 with, for example, N,N''-sulfuryldiimidazole, methanesulfonyl chloride, p-toluenesulfonyl chloride, and the like in the presence of a base, for example, lithium hexamethyldisilazane, sodium hydride, potassium t-butoxide, and the like, in any suitable solvent, for example, tetrahydrofuran, diethyl ether, and the like, to provide compound 103. Compound 103 can be reacted with a nitrogen nucleophile, for example, sodium azide, in any suitable solvent, for example, dimethylformamide, dimethyl sulfoxide, and the like, to provide, for example, azido compound 104. When the nitrogen nucleophile is an azide, the azido compound 104 can be reduced using any suitable reducing agent, for example, by catalytic hydrogenation, zinc reduction, and the like, in any suitable solvent, for example, methanol, ethanol, and the like, to provide amino compound 105. Compound 105 can be acylated using any suitable acylating agent, for example, glycolic acid, fluoroacetic acid, and the like, using any suitable coupling agent, for example, N-(3-dimethylaminopropyl)-N-ethylcarbodiimide hydrochloride and the like, in the presence of any suitable catalyst, for example, N-hydroxybenzotriazole and the like, in the presence of any suitable base, for example, Hünig's base and the like, in any suitable solvent, for example, dimethylformamide and the like, to provide target compound 106. "R" in compounds 101-106 can be a fragment of the structure:

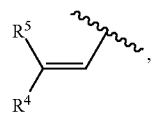

wherein $R^4$ and $R^5$ are as described herein, or a fragment of the structure:

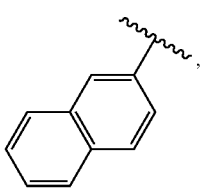 [SMILES: *c1ccc2ccccc2c1]

as described herein.

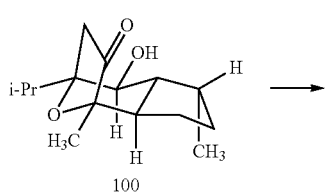

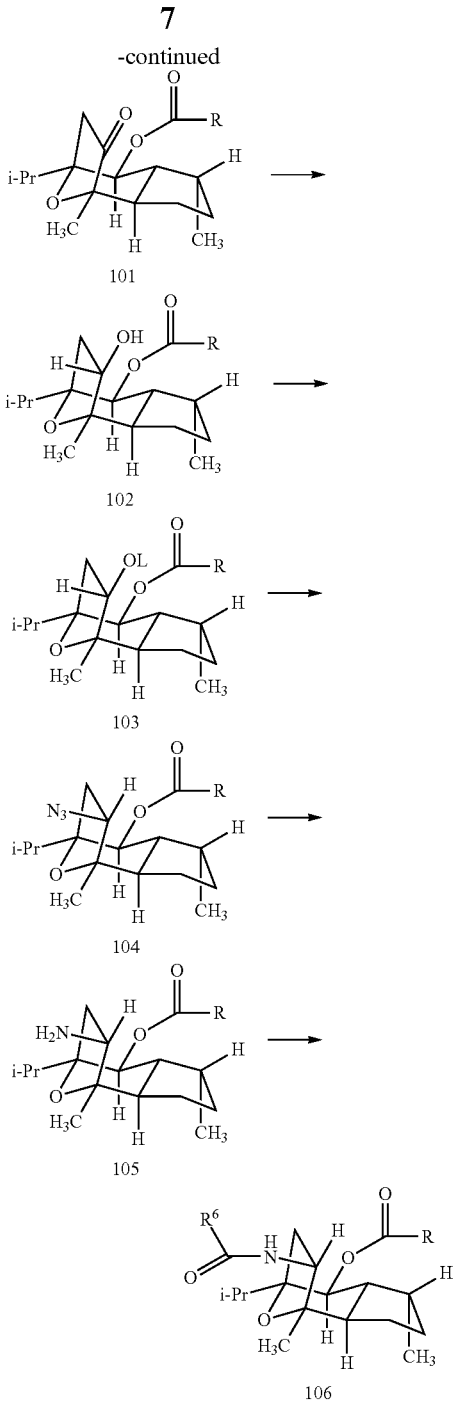

The invention also provides a pharmaceutical composition comprising a pharmaceutically acceptable carrier and a compound or epimer as described above.

The invention also provides a method of treating cancer in an animal comprising administering to the animal an effective amount of a compound or epimer of any of the embodiments described above. The cancer can be any suitable cancer, for example, leukemia, non-small cell lung cancer, colon cancer, melanoma, prostate cancer, kidney cancer, breast cancer, CNS cancer, Ewing's sarcoma, and ovarian cancer, particularly renal cancer, breast cancer, or Ewing's sarcoma.

Figure 5:
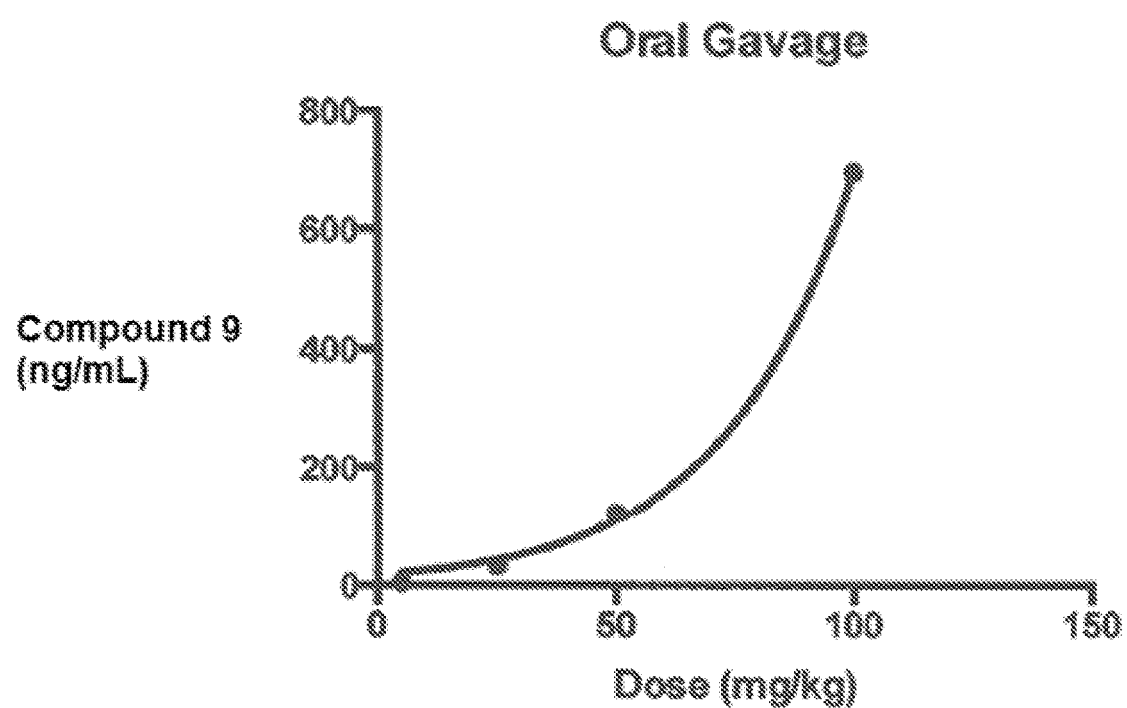
FIG. 5 depicts the plasma concentration of compound 9 in mice as a function of dosage 30 minutes after oral gavage of the compound.
Figure 6:
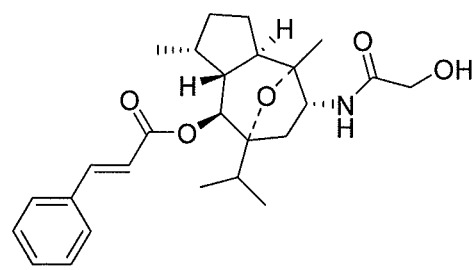
FIG. 6 depicts compound structures in accordance with an embodiment of the invention.
Figure 6:
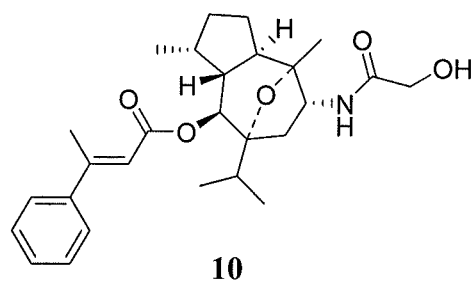
Figure 6:
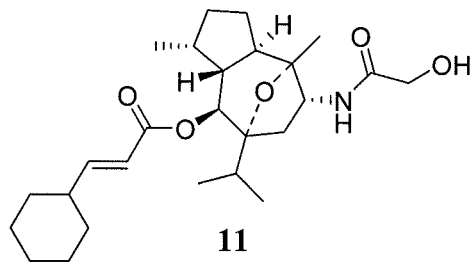
Figure 6:
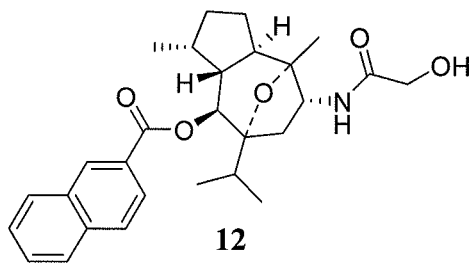
Figure 6:
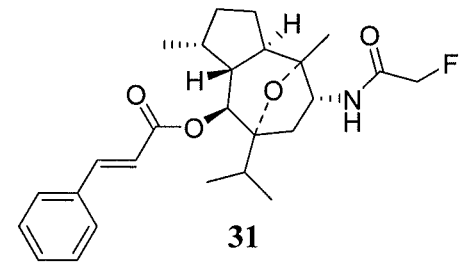

In accordance with an embodiment of the invention, aza englerins, particularly compounds 9, 10, 11, 12, and 31, as shown in FIG. 5, are active against, e.g., decrease the growth of, renal cancer cell lines, e.g., 786-0, A-498, ACHN, CAKI-1, RXF 393, SN 12C, TK-10 and UO-31. In accordance with an embodiment, compounds 9, 10, 11, 12, and 31 are active against, e.g., decrease the growth of breast cancer cell lines, e.g., MCF7, MDA-MB-231/ATCC, HS 578T, BT-549, T-47D, and MDA-MB-468. In accordance with an embodiment of the invention, compounds 9, 10, 11, 12, and 31 are active against CNS cancer cell lines, e.g., SF-268, SF-295, SF-539, SNB-19, SNB-75, and U251. In accordance with an embodiment, compounds 9, 10, 11, 12, and 31 are active against, e.g., decrease the growth of, ovarian cancer cell lines, e.g., IGROV1, OVCAR-3, OVCAR-5, OVCAE-8, NCI/ADR-RES, and Sk-OV-3. In accordance with an embodiment, compounds 9, 10, 11, 12, and 31 are active against, e.g., decrease the growth of, colon cancer cell lines, e.g., COLO 205, HCT-116, HCT-15, HT29, KM12, and SW-620. In accordance with an embodiment, compounds 9, 10, 11, 12, and 31 are active against, e.g., decrease the growth of, leukemia cell lines, e.g., CCRF-CEM, HL-60 (TB), K-562, MOLT-4, RPMI-8226, and SR. In accordance with an embodiment, compounds 9, 10, 11, 12, and 31 are active against, e.g., decrease the growth of, non-small cell lung cancer cell lines, e.g., A549/ATCC, EKVX, HOP-62, HOP-92, NCI-H226, NCI-H23, NCI-H322M, NCI-H460, and NCI-H522. In accordance with an embodiment, compounds 9, 10, 11, 12, and 31 are active against, e.g., decrease the growth of, melanoma cell lines, e.g., LOX IMVI, MALME-3M, M14, MDA-MB-435, SK-MEL-2, SK-MEL-28, SK-MEL-5, UACC-257, and UACC-62. In accordance with an embodiment, compounds 9, 10, 11, 12, and 31 are active against, e.g., decrease the growth of prostate cancer cell lines, e.g., PC-3 and DU-145. For example, these compounds have a $GI_{50}$ or $IC_{50}$ of 1 μM or less, preferably 0.1 μM or less.

As used herein, the term "treat" does not necessarily imply complete elimination of a cancer. Rather, there are varying degrees of treatment of which one of ordinary skill in the art recognizes as having a benefit or therapeutic effect. In this respect, the cancer can be treated to any extent through the present inventive method. For example, at least 10% (e.g., at least 20%, 30%, or 40%) of the growth of a cancerous tumor desirably is inhibited upon administration of a compound described herein. Preferably, at least 50% (e.g., at least 60%, 70%, or 80%) of the growth of a cancerous tumor is inhibited upon administration of a compound described herein. More preferably, at least 90% (e.g., at least 95%, 99%, or 100%) of the growth of a cancerous tumor is inhibited upon administration of a compound described herein. In addition or alternatively, the inventive method may be used to inhibit metastasis of a cancer.

An aspect of the present invention involves activation of the heat shock protein 70 (HSP70). Heat shock proteins (HSPs) are the largest family of transcriptionally regulated molecular chaperone proteins that respond to cellular stress. HSPs aid in repair of protein damage and survival of normal cellular functions. Insulin resistance and hyperglycemic people have reduced HSP70 protein and gene expression. HSP70 assists in protein folding and re-folding. Heat shock factor 1 (HSF1) mediates most transcriptional activation by binding to heat shock elements in the promoter region of the HSP genes, with the resultant transcription of HSP70 mRNA being most abundant. In resting cells, HSF1 is complexed with various heat shock proteins such as HSP70 and/or HSP90. After stress, damaged proteins become abundant and liberate the heat shock factor from its HSP70 or HSP90 complex. This process sets the stage for the trimerization, nuclear translocation and phosphorylation of HSF1, which are all prerequisites for its binding the special nucleotide segments, called heat shock elements in the promoter region of the HSP genes. HSF1 thus undergoes modifications such as trimerization, phosphorylation, and acetylation as well as product feedback inhibition to modulate the activation-attenuation cycle.

Induction of HSPs not only protects de novo proteins being translated through the endoplasmic reticulum but also protects oxidized proteins and upregulates intracellular antioxidant mechanisms, which together minimize the chronic inflammatory state associated with insulin resistance. See, for example, Kavanagh, K., et al. *Am. J Physiol Endocrinol Metab.* 300: E894-E901, 2011, which also shows that restoring HSP70 deficiencies improves glucose tolerance in diabetic monkeys. HSP70 is also known to prevent damage to cardiac muscle by both ischemia and reperfusion. Curie et al., Heat-shock response is associated with enhanced postischemic ventricular recovery, *Cir. Res.* 63, 395-397 (1988). Aged organisms contain an increased amount of misfolded proteins, and the induction of HSP70 is impaired in both aged rats and humans. Induction of heat shock proteins also leads to increased life expectancy in yeast, *Drosophila* or *C. elegans.*

In accordance with an embodiment, the invention provides a method of treating an animal for a disease or condition associated with insulin resistance comprising administering to the animal an effective amount of a compound of formula (I) or (II) or an epimer thereof. In accordance with an embodiment of the present invention, the disease or condition associated with insulin resistance is diabetes, obesity, inflammation, metabolic syndrome, polycystic ovary disease, arteriosclerosis, non-alcoholic fatty liver disease, reproductive abnormality in a female, and growth abnormality. In an embodiment, the disease associated with insulin resistance is type 1 and/or type 2 diabetes, particularly type 2 diabetes.

Polycystic ovary syndrome or disease is a condition in which there is an imbalance of a woman's female sex hormones. The hormone imbalance may cause changes in the menstrual cycle, e.g., absent periods or irregular menstrual periods, development of male sex characteristics, skin changes, e.g., acne or dark or thick skin markings around the armpits, groin, neck, and breasts, small cysts in the ovaries, trouble getting pregnant, and other problems.

Obesity relates to excess body fat. Obesity is associated with an increased incidence of diabetes, hypertension, increased levels of very low density lipoproteins (VLDL) triglycerides, low density lipoproteins (LDL) cholesterol, and decreased levels of high density lipoproteins (HDL) cholesterol, all of which are risk factors for the development of vascular disease. Obesity is also a known risk factor for non-alcoholic fatty liver disease, hypertension, stroke, gall bladder disease, osteoarthritis, obstructive sleep apnea and other breathing problems, as well as some forms of cancer.

In accordance with an embodiment of the invention, the treatment of arteriosclerosis includes delaying or preventing the development of coronary artery disease, stroke, or peripheral vascular disease. In accordance with an embodiment of the invention, the treatment of fatty liver includes delaying or preventing the progression of cirrhosis of the liver.

In an embodiment, the present invention provides a method of treating an HIV-infected animal comprising co-administering to the animal an effective amount of a compound of formula (I) or formula (II) or an epimer thereof.

In another embodiment, the present invention provides a method of treating an HTLV-infected animal comprising co-administering to the animal an effective amount of a compound of formula (I) or formula (II) or an epimer thereof and at least one antiviral agent.

In another embodiment, the present invention provides a method of increasing the activity of latent infected CD4+ cells of an animal carrying HIV comprising administering to the animal an effective amount of a compound of formula (I) or formula (II) or an epimer thereof.

In another embodiment, the present invention provides a method of inhibiting Treg activation and number in an animal carrying HTLV comprising administering to the animal an effective amount of a compound of formula (I) or formula (II) or an epimer thereof.

In another embodiment, the present invention provides a method of decreasing Glut1 expression in an ATL cell in an animal carrying HTLV comprising administering to the animal an effective amount of a compound of formula (I) or formula (II) or an epimer thereof.

The invention provides methods for using a compound of formula (I) or formula (II) or an epimer thereof as an adjuvant therapy for HIV 1-infected patients, patients having AIDS, patients having ATL, and other immunodeficient patients carrying viral infection.

In accordance with some embodiments, the compound of formula (I) or formula (II) or an epimer thereof is administered as an adjuvant in combination with an anti-viral agent or combination of agents. For example, in some embodiments, the combinatorial formulation may include one or more compounds from a highly active antiretroviral therapy protocol (HAART protocols) in combination with a compound of formula (I) or formula (II) or an epimer thereof, among other combinations. Other combinatorial formulations may, for example, include a compound of formula (I) or formula (II) or an epimer thereof and/or compounds effective in treating the opportunistic infections of AIDS as well as compounds from HAART protocols. In other embodiments, the combinatorial formulation may include one or more additional chemotherapeutic agents.

To practice coordinate administration methods of the invention, a compound of formula (I) or formula (II) or an epimer thereof may be administered, simultaneously or sequentially, in a coordinate treatment protocol with one or more of the secondary or adjunctive therapeutic agents contemplated herein. Thus, in certain embodiments compound of formula (I) is administered coordinately with a different agent, or any other secondary or adjunctive therapeutic agent contemplated herein, using separate formulations or a combinatorial formulation as described above (i.e., comprising both compound of formula (I) or formula (II) or an epimer thereof, and another therapeutic agent). This coordinate administration may be done simultaneously or sequentially in either order, and there may be a time period while only one or both (or all) active therapeutic agents individually and/or collectively exert their biological activities.

In one embodiment, such coordinate treatment methods may, for example, follow or be derived from various highly active antiretroviral therapy protocols (HAART protocols) and include regimens such as, but not limited to, two nucleoside analogue reverse transcriptase inhibitors plus one or more protease inhibitor or non-nucleoside analogue reverse transcriptase inhibitor with a compound of formula (I) or formula (II) or an epimer thereof, among other combinations. Other coordinate treatment methods may, for example, include a compound of formula (I) or formula (II)

or an epimer thereof and/or treatments for opportunistic infections as well as compounds from HAART protocols. A distinguishing aspect of all such coordinate treatment methods is that the compound of formula (I) or formula (II) or an epimer thereof exerts at least some activity, which yields a favorable clinical response in conjunction with a complementary AIDS symptom decreasing, or distinct, clinical response provided by the secondary or adjunctive therapeutic agent. Often, the coordinate administration of the compound of with the secondary or adjunctive therapeutic agent will yield improved therapeutic or prophylactic results in the subject beyond a therapeutic effect elicited by the compound of formula (I) or formula (II) or an epimer thereof, or the secondary or adjunctive therapeutic agent administered alone. This qualification contemplates both direct effects, as well as indirect effects.

Within exemplary embodiments, a compound of formula (I) or formula (II) or an epimer thereof will be coordinately administered (simultaneously or sequentially, in combined or separate formulation(s)), with one or more secondary treating agents, or other indicated or adjunctive therapeutic agents, e.g., selected from, for example, protease inhibitors, including, but not limited to, saquinavir, indinavir, ritonavir, nelfinavir, atazanavir, darunavir, fosamprenavir, tipranavir and amprenavir; nucleoside reverse transcriptase inhibitors including but not limited to, zidovudine, didanosine, stavudine, lamivudine, zalcitabine, emtricitabine, tenofovir disoproxil fumarate, AVX754 and abacavir; non-nucleoside reverse transcriptase inhibitors including, but not limited to, nevaripine, delavirdine, calanolide A, TMC125 and efavirenz; combination drugs including, but not limited to, efavirenz/emtricitabine/tenofovir disoproxil fumarate, lamivudine/zidovudine, abacavir/lamivudine, abacavir/lamivudine/zidovudine, emtricitabine/tenofovir disoproxil fumarate, sulfamethoxazole/trimethoprim, and lopinavir/ritonavir; entry and fusion inhibitors, including, but not limited to, enfuvirtide, AMD070, BMS-488043, fozivudine tidoxil, GSK-873,140, PRO 140, PRO 542, Peptide T, SCH-D, TNX-355, and UK-427,857; treatments for opportunistic infections and other conditions associated with AIDS and HIV including, but not limited to, acyclovir, adefovir dipivoxil, aldesleukin, amphotericin b, azithromycin, calcium hydroxylapatite, clarithromycin, doxorubicin, dronabinol, entecavir, epoetin alfa, etoposide, fluconazole, ganciclovir, immunoglobulins, interferon alfa-2, ionomycine, isoniazid, itraconazole, megestrol, paclitaxel, peginterferon alfa-2, pentamidine, poly-1-lactic acid, ribavirin, rifabutin, rifampin, somatropin, testosterone, trimetrexate, and valganciclovir; integrase inhibitors including, but not limited to, GS 9137, MK-0518; microbicides, including, but not limited to, BMS-378806, C31G, carbopol 974P, carrageenan, cellulose sulfate, cyanovirin-N, dextran sulfate, hydroxyethyl cellulose, PRO 2000, SPL7013, tenofovir, and UC-781, and IL-2.

In accordance with the invention, the term "animal" includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The compound (or epimer thereof) is administered in a dose sufficient to treat the cancer. Such doses are known in the art (see, for example, the *Physicians' Desk Reference* (2004)). The compounds can be administered using techniques such as those described in, for example, Wasserman et al., *Cancer*, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response, e.g., as determined by measuring cancer-specific antigens or other measurable parameters related to the tumor load of a patient.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. Other preferred pharmaceutical carriers are Labrasol™ (e.g., caprylocaproyl polyoxylglycerides and PEG-8 caprylic/capric glycerides) and soybean oil. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound or epimer of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound or epimer of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound or epimer in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Thus, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, Remington's Pharmaceutical Science (17th ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

The following examples further illustrate the invention but, of course, should not be construed as in any way limiting its scope.

General Information: All reactions were performed in single neck oven- or flame-dried round-bottom flasks fitted with rubber septa under a positive pressure of argon, unless otherwise noted. Air- and moisture-sensitive liquids were transferred via syringe or stainless steel cannula. Organic solutions were concentrated by rotary evaporation below 35° C. at 10 Torr (diaphragm vacuum pump) unless otherwise noted. Analytical thin-layer chromatography (TLC) was performed using glass plates pre-coated with silica gel (0.25 mm, 60-Å pore size, 230-400 mesh, Sorbent Technologies) impregnated with a fluorescent indicator (254 nm). TLC plates were visualized by exposure to ultraviolet light (UV), then were stained by submersion in aqueous acidic dinitrophenylhydrazine solution (DNP), Ceric Ammonium Molybdate (CAM), or aqueous basic potassium permanganate solution (KMn04), followed by brief heating on a hot plate (215° C., 1 Q.-30 s). Flash chromatography was performed as described by Still et al. 1 employing silica gel (60-Å pore size, 40-63 µm, standard grade, Sorbent Technologies).

Materials: Commercial reagents and solvents were used as received with the following exceptions. Triethylamine, dichloromethane, ethyl ether, dimethylsulfoxide, tetrahydrofuran, hexane, toluene, and benzene were purified by the method of Pangborn, et. Al. 2-Chloropropanoate, 3-methyl-2-butanone, hexamethyldisilazane, and N,N-diisopropylamine were distilled from calcium hydride under an atmosphere of argon at 760 Torr. Hexamethylphosphoramide (HMPA) and N,N-dimethylformamide (DMF) were distilled from calcium hydride under reduced pressure (0.1 Torr) and stored under argon. 1,2-Diiodoethane was recrystallized from ethyl ether and stored under an atmosphere of argon. Lithium chloride was flame dried under vacuum (0.1 Torr, 10 min), cooled under an atmosphere of argon, and the dried solid was stored at 150° C. (drying oven, 760 Torr); the dried solid was also flame dried under vacuum (0.1 Torr, 10 min) immediately prior to use. The molarity of solutions of n-butyllithium was determined by titration against diphenylacetic acid as an indicator (average of three determinations). Where noted, solvents were deoxygenated before use by bubbling with argon for 20 minutes.

Instrumentation: Proton nuclear magnetic resonance ($^1$H NMR) spectra and carbon nuclear magnetic resonance ($^{13}$C NMR) spectra were recorded on Varian Mercury 300 MHz/75 MHz or Varian INOVA 500 MHz/125 MHz NMR spectrometers at 23° C. Proton chemical shifts are expressed in parts per million (ppm, δ scale) downfield from tetramethylsilane and are referenced to residual protium in the NMR solvent (CHCl$_3$: δ 7.26, CD$_2$HOD: δ 3.31, CD$_3$SOCD$_2$H: δ 2.50). Carbon chemical shifts are expressed in parts per million (ppm, δ scale) downfield from tetramethylsilane and are referenced to the carbon resonance of the NMR solvent (CDCl$_3$: δ 77.00, CD$_3$OD: δ 49.00, CD$_3$SOCD$_3$: δ 39.52). Data are represented as follows: chemical shift, multiplicity (s=singlet, d=doublet, t=triplet, q=quartet, m=multiplet, br=broad, app=apparent), integration, and coupling constant (J) in Hertz (Hz). Infrared (IR) spectra were obtained using a Perkin Elmer 1600 FT-IR spectrophotometer referenced to a polystyrene standard and data are represented as frequency of absorption (cm$^{-1}$). Optical rotations were determined using a JASCO-DIP-370 polarimeter equipped with a sodium lamp source (589 nm). Reported readings are the average of three determinations for each sample. High-resolution mass spectra were obtained using an Agilent 1100 quaternary LC system coupled to an Agilent 6210 LC/MSD-TOF fitted with an ESI or an APCI source.

EXAMPLE 1

This example demonstrates synthesis of compounds in accordance with an embodiment of the invention.

The following procedure for the preparation of the known 3-furanone 4 (S. K. Mukerji et al., 1983, Tetrahedron 39: 2231-2235) was adapted from a literature report for the synthesis of 3-silyloxyfurans (J. D. Winkler et al., Org. Lett. 2005, 7: 387-389).

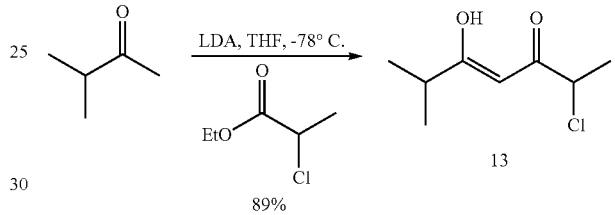

A solution of n-butyllithium (2.50 M, 14.4 ml, 36.0 mmol, 1.20 equiv) was added to a stirred solution of N,N-diisopropylamine (5.34 ml, 38.0 mmol, 1.26 equiv) in tetrahydrofuran (250 ml) at −78° C. The resulting solution was warmed briefly to 0° C., then was cooled to −78° C. whereupon a solution of 3-methyl-2-butanone (3.20 ml, 30.0 mmol) in tetrahydrofuran (15 ml) was added dropwise. The resultant mixture was stirred at −78° C. for 30 min, whereupon ethyl 2-chloropropanoate (4.20 ml, 33.0 mmol, 1.10 equiv) was added. The resultant mixture was allowed to warm to 23° C. and stirred at that temperature for 8 h. The resultant yellow solution was cooled to 0° C. and was quenched with saturated aqueous ammonium chloride solution (30 ml). The layers were separated and the aqueous layer was extracted with dichloromethane (3×30 ml). The combined organic layers were dried over anhydrous sodium sulfate and the dried solution was concentrated. Purification of the residue by flash column chromatograph (4% ethyl acetate-hexanes) afforded 13 (4.60 g, 89%) as a colorless oil. Chlorodiketone 13: TLC: 4% ethyl acetate-hexanes, R$_f$=0.50 (UV, KMnO$_4$). $^1$H NMR: (300 MHz, CDCl$_3$). δ: 5.84 (s, 1H), 4.38 (q, J=6.9 Hz, 1H), 2.58-2.49 (m, 1H), 1.68 (d, J=7.2 Hz, 3H), 1.18 (d, J=7.0 Hz, 6H). $^{13}$C NMR: (75 MHz, CDCl$_3$). δ: 198.6, 192.1, 94.8, 56.6, 36.7, 21.9, 19.5. FTIR (NaCl, thin film), cm$^{-1}$: 2974, 1604. HRMS: ESI [M+]$^+$ Calcd. for C$_8$H$_{14}$ClO$_2$: 177.0677. Found: 177.0675.

The following describes a preparation of compound 4.

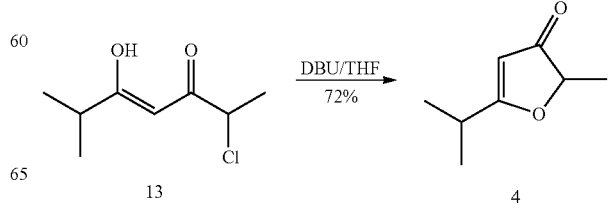

1,8-Diazabicyclo[5.4.0]undec-7-ene (6.00 ml, 40.0 mmol, 1.40 equiv) was added dropwise to a stirred solution of 13 (3.50 g, 28.5 mmol, 1 equiv) in tetrahydrofuran (100 ml) at 23° C. A pale yellow precipitate formed immediately. The resultant suspension was stirred at 23° C. for 12 h, then was partitioned between water (100 ml) and ethyl acetate (100 ml). The layers were separated and the aqueous phase was extracted with ethyl acetate (6×50 ml). The combined organic layers were dried over anhydrous sodium sulfate and the dried solution was concentrated. Purification of the residue by flash column chromatography (20% ethyl acetate-hexanes) gave 4 (2.80 g, 72%) as a pale yellow liquid. 3-furanone 4: TLC: 20% ethyl acetate-hexanes, $R_f$=0.35 (UV, KMnO$_4$). $^1$H NMR (300 MHz, CDCl$_3$), δ: 5.38 (s, 1H), 4.49 (q, J=6.9 Hz, 1H), 2.76-2.66 (m, 1H), 1.43 (d, J=7.0 Hz, 3H), 1.24 (s, 3H), 1.22 (s, 3H). $^{13}$C NMR (75 MHz, CDCl$_3$). δ: 206.1, 198.7, 100.7, 82.6, 30.5, 19.7, 19.7, 16.6. FTIR (NaCl, thin film), cm$^1$: 2975, 1742, 1707, 1586. HRMS: ESI [M+]$^+$ Calcd for $C_8H_{13}O_2$: 141.0910. Found: 141.0911.

The following literature procedure for the synthesis of 5 was performed (D. E. Chavez et al., *Org. Lett.* 2003, 5(14): 2563-2565).

The second generation Grubbs catalyst (933 mg, 1.10 mmol, 0.05 equiv) was added in portions to a solution of 14 (S. Takano et al., *Chem. Lett.* 1989, 1283-1284) (3.60 g, 22.0 mmol) in dichloromethane (200 mL) heated at reflux. The resultant brown solution was heated at reflux for 48 h, then was cooled and concentrated. Purification of the residue by flash column chromatography (4% ethyl acetate-hexanes) gave 5 (2.40 g, 99%) as a pale yellow oil. Aldehyde 5: TLC: 4% ethyl acetate-hexanes, $R_f$=0.30 (UV, KMnO$_4$). [α]$_D^{23}$=−6.2° (c=0.58, CH$_2$Cl$_2$). $^1$H NMR (300 MHz, CDCl$_3$). δ: 9.76 (s, 1H), 6.80 (m, 1H), 3.06-2.98 (m, 1H), 2.68-2.55 (m, 1H), 2.27-2.14 (m, 1H), 1.63-1.53 (m, 2H), 1.13 (d, J=7.0 Hz, 3H). $^{13}$C NMR (75 MHz, CDCl$_3$). δ: 190.0, 153.2, 151.8, 36.8, 32.6, 32.1, 19.4. FTIR (NaCl, thin film), cm$^{-1}$ 2957, 1716, 1683, 1458. HRMS: ESI [M+H]$^+$ Calcd for $C_7H_9O$: 111.0804. Found: 111.0810. Assay of enantiomeric excess: Chiral HPLC analysis (Regis (S, S)-Whelk-0 #1 25×4.6 mm, 1 mL/min flow rate, 5% iso-propanol-hexanes, $t_R$ (major)= 7.30 min, $t_R$ (minor)=6.92 min) 79% ee, average of three determinations.

The following describes a preparation of compound 6.

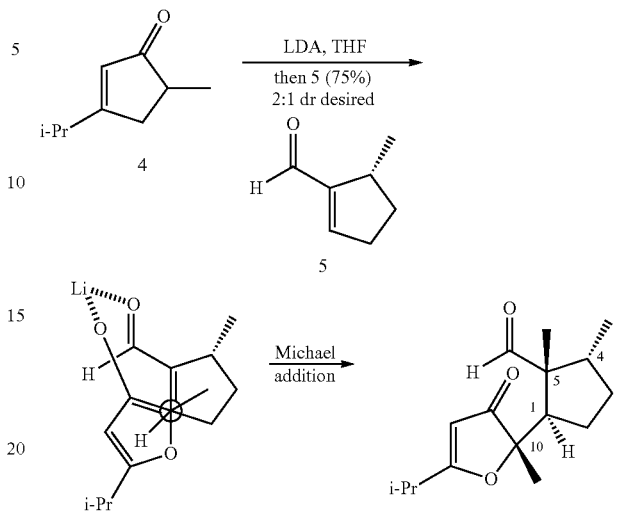

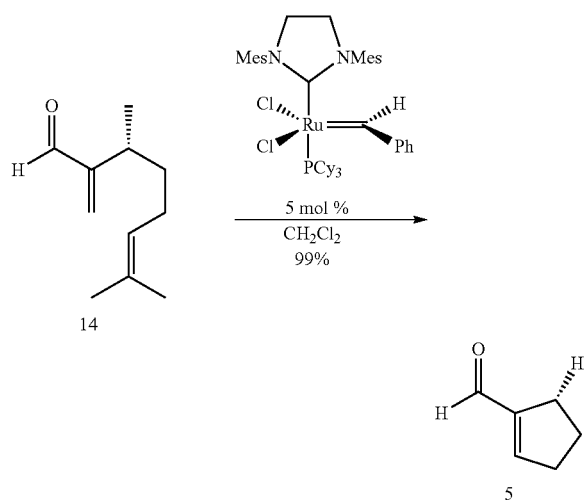

To prepare compound 6, a solution of n-butyllithium (2.50 M, 2.20 mL, 5.50 mmol, 1.28 equiv) was added to a stirred solution of N,N-diisopropylamine (0.85 mL, 6.00 mmol, 1.40 equiv) in tetrahydrofuran (50 ml) at −78° C. The resultant solution was warmed briefly to 0° C., then was cooled to −78° C. whereupon a solution of the 3-furanone 4 (600 mg, 4.30 mmol, 1 equiv) in tetrahydrofuran (5 ml) was added dropwise. The resultant mixture was stirred at −78° C. for 30 min, whereupon a solution of 5 (550 mg, 5.00 mmol, 1:16 equiv) in tetrahydrofuran (5 mL) was added. The reaction mixture was stirred at −78° C. for 30 min, was warmed to 23° C. and stirred at that temperature for 1 h. The reaction mixture was cooled to 0° C. whereupon saturated aqueous ammonium chloride solution (30 mL) was added carefully. The layers were separated and the aqueous layer was extracted with dichloromethane (3×30 mL). The combined organic layers were dried over anhydrous sodium sulfate and the dried solution was concentrated. Purification of the residue by flash column chromatography (20% ethyl acetate-hexanes) afforded the Michael adduct 6 (807 mg, 75%, 2:1 dr desired: Σ: others) as a yellow oil. Michael adduct 6: TLC: 20% ethyl acetate-hexanes, R$_f$=0.35 (UV, DNP). [α]$_D^{23}$=+36.1° (c=0.38, CHCl$_3$). Major isomer: $^1$H NMR (300 MHz, CDCl$_3$). δ: 9.62 (d, J=3.2 Hz, 1H), 5.32 (s, 1H), 2.90 (dd, J$_1$=8.8 Hz, J$_2$=15.6 Hz, 1H), 2.69-2.62 (m, 2H), 2.38-2.27 (m, 1H), 1.99-1.90 (m, 1H), 1.83-1.73 (m, 2H), 1.59-1.48 (m, 1H), 1.29 (s, 3H), 1.19 (d, J=7.0 Hz, 6H), 0.98 (d, J=7.0 Hz, 3H). Major isomer: $^{13}$C NMR: (75 MHz, CDCl$_3$). δ: 206.9, 204.4, 197.7, 101.2, 91.2, 54.5, 43.9, 39.0, 34.6, 30.5, 26.7, 21.0, 19.8, 19.5, 16.0. FTIR (NaCl, thin film), cm$^{-1}$ 2964, 1717, 1588. FIRMS: ESI [M+H]$^+$ Calcd for $C_{15}H_{23}O_3$: 251.1642. Found: 251.1649.

The following describes a preparation of compound 7.

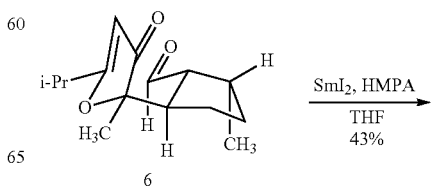

-continued

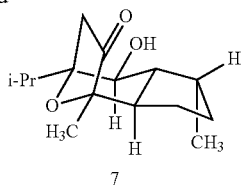

7

A solution of samarium (II) iodide in tetrahydrofuran (0.1 M, 8.64 mL, 864 μmol, 4.00 equiv), freshly prepared from samarium powder (195 mg, 1.30 mmol, 6.00 equiv) and 1,2-diiodoethane (244 mg, 864 μmol, 4.00 equiv)) 8 was added dropwise to a solution of the Michael adduct 6 (54.0 mg, 216 μmol, 1 equiv) and hexamethylphosphoramide (700 μL, 4.00 mmol, 18.5 equiv) in deoxygenated tetrahydrofuran (10 ml). The resultant deep purple mixture was stirred at 23° C. for 3 h, was cooled to 0° C. and quenched by the addition of aqueous hydrochloric acid solution (1 N, 10 ml). The layers were separated and the aqueous layer was extracted with dichloromethane (3×10 mL). The combined organic layers were washed with saturated aqueous sodium bicarbonate solution (10 mL) dried over anhydrous sodium sulfate, and the dried solution was concentrated. Purification of the residue by flash column chromatography (10% ethyl acetate-hexanes) gave the ketoalcohol 7 (16.0 mg, 43%) as a pale yellow oil. Ketoalcohol 7: TLC: 20% ethyl acetate-hexanes, $R_f$=0.30 (CAM). $[\alpha]_D^{23}$=-47.4° (c=1.0, CHCl$_3$). $^1$H NMR (300 MHz, CDCl$_3$). δ: 3.90 (dd, $J_1$=10.3 Hz, $J_2$=4.3 Hz, 1H), 2.46 (d, J=18.5 Hz, 1H), 2.31 (d, J=18.5 Hz, 1H), 2.33-2.24 (m, 1H), 2.10 (sept, J=7.0 Hz, 1H), 1.98-1.94 (m, 1H), 1.67-1.58 (m, 2H), 1.39 (d, J=4.3 Hz, 1H), 1.22 (s, 3H), 1.18-1.12 (m, 2H), 1.09 (d, J=7.0 Hz, 3H), 1.08 (d, J=7.0 Hz, 3H), 0.901 (d, J=7.0 Hz, 3H). $^{13}$C NMR (125 MHz, CDCl$_3$). δ: 215.7, 83.5, 82.8, 70.4, 49.3, 46.4, 41.5, 32.3, 31.0, 30.4, 24.2, 17.9, 17.5, 17.0, 16.7. FTIR (NaCl, thin film), cm$^{-1}$ 3470, 2958, 1749. HRMS: ESI [M+H]$^+$ Calcd for C$_{15}$H$_{25}$O$_3$: 253.1798. Found: 253.1792.

The following describes a preparation of compound 8.

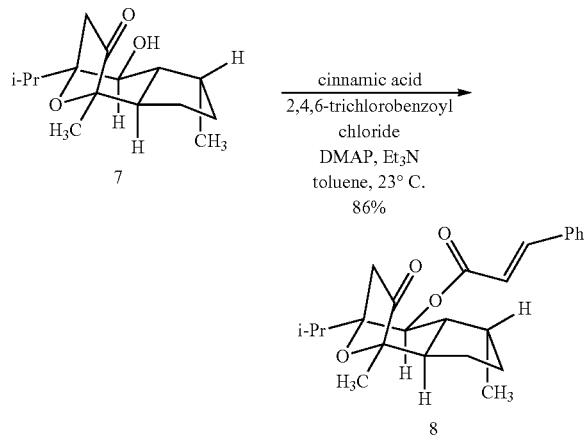

To prepare compound 8, cinnamic acid (18.0 mg, 120 μmol, 2.00 equiv), triethylamine (25.0 μL, 180 μmol, 3.00 equiv), 2,4,6-trichlorobenzoyl chloride (25.0 μL, 155 μmol, 2.58 equiv) and 4-dimethylaminopyridine (1.0 mg, 8.2 μmol, 0.14 equiv) were added sequentially to a solution of 7 (16.0 mg, 60.0 μmol, 1 equiv) in toluene (2 ml). The resultant mixture was stirred at 23° C. for 2 d, and was quenched with aqueous hydrochloric acid solution (1 N, 5 ml). The layers were separated and the aqueous layer was extracted with dichloromethane (3×5 ml). The combined organic layers were washed with saturated aqueous sodium bicarbonate (10 mL), and were then dried over anhydrous sodium sulfate and the dried solution was concentrated. Purification of the residue by flash column chromatography (4% ethyl acetate-hexanes) afforded 8 (20.0 mg, 86%) as a colorless oil. Ketoester 8: TLC: 4% ethyl acetate-hexanes, $R_f$=0.30 (UV, CAM). $[\alpha]_D^{23}$=-52.2° (c=0.32, CHCl$_3$). $^1$H NMR (300 MHz, CDCl$_3$). δ: 7.67 (d, J=16.1 Hz, 1H), 7.54-7.50 (m, 2H), 7.49-7.37 (m, 3H), 6.39 (d, J=16.1 Hz, 1H), 5.37 (d, J 10.6 Hz, 1H), 2.52 (ab, 1H), 2.14-2.06 (m, 1H). 2.01-1.92 (m, 1H), 1.91-1.75 (m, 2H), 1.68-1.47 (m, 2H), 1.256 (s, 3H), 1.23-1.18 (m, 2H), 1.03 (t, J=7.4 Hz, 6H), 0.94 (d, J=7.2 Hz, 3H). $^{13}$C NMR (75 MHz, CDCl$_3$). δ: 215.5, 165.7, 145.7, 134.4, 130.7, 129.2, 128.4, 117.9, 83.7, 82.6, 71.0, 48.6, 46.3, 42.9, 33.3, 31.3, 30.9, 23.5, 18.2, 17.7, 17.1, 17.0. FTIR (NaCl, thin film), cm$^{-1}$: 2960, 1754, 1713, 1636. HRMS: ESI [M+H]$^+$ Calcd. for C$_{24}$H$_{31}$O$_4$: 383.2217. Found: 383.2213.

The following describes a preparation of compound 15.

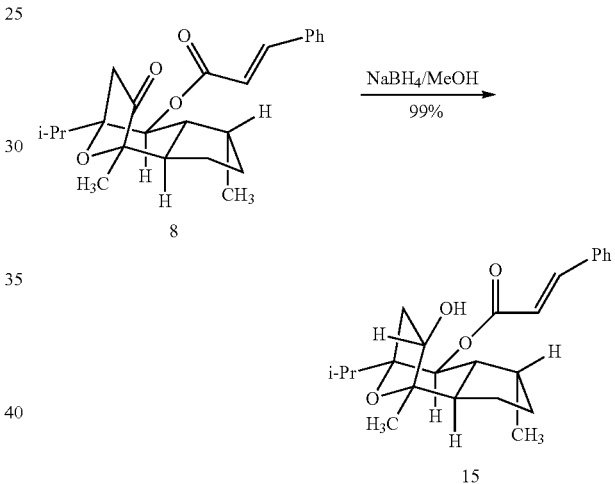

To prepare compound 15, sodium borohydride (2.50 mg, 65.0 μmol, 1.00 equiv) was added to a solution of S (25 mg, 65 μmol, 1 equiv) in methanol (2 ml) at 0° C. The resultant mixture was stirred at 0° C. for 30 min, and excess borohydride was quenched by the addition of saturated aqueous ammonium chloride solution (5 ml). The resultant mixture was extracted with dichloromethane (3×5 mL), the combined organic layers were dried over anhydrous sodium sulfate, and the dried solution was concentrated. Purification of the residue by flash column chromatography (20% ethyl acetate-hexanes) afforded 15 (25 mg, quantitative) as a colorless oil. Ketoalcohol 15: TLC: 20% ethyl acetate-hexanes, $R_f$=0.40 (UV, CAM). $[\alpha]_D^{23}$-32.6° (c=0.30, CHC13). $^1$H NMR (300 MHz, CDCl$_3$). δ: 7.66 (d, J=16.2 Hz, 1H), 7.54-7.50 (m, 2H), 7.39-7.36 (m, 3H), 6.40 (d, J=16.2 Hz, 1H), 5.22 (d, J=10.3 Hz, 1H), 4.19 (dd, $J_1$=10.7 Hz, $J_2$=4.8 Hz, 1H), 2.39-2.29 (m, 2H), 2.16-2.04 (m, 2H), 1.98-1.67 (m, 6H), 1.32 (s, 3H), 1.29-1.21 (m, 1H), 0.98-0.93 (m, 9H). $^{13}$C NMR (75 MHz, CDCl$_3$). δ: 166.1, 145.1, 134.6, 130.5, 129.1, 128.3, 118.6, 84.8, 81.6, 81.2, 72.7, 49.4, 46.4, 39.6, 33.1, 31.7, 31.4, 24.6, 23.5, 17.9, 17.3, 17.1. FTIR (NaCl, thin film), cm$^{-1}$ 2923, 1710, 1636. HRMS: ESI [M+H]$^+$ Calcd. For C$_{24}$H$_{33}$O$_4$: 385.2373. Found: 385.2389.

The following describes a preparation of compound 16.

The following describes a preparation of compound 17.

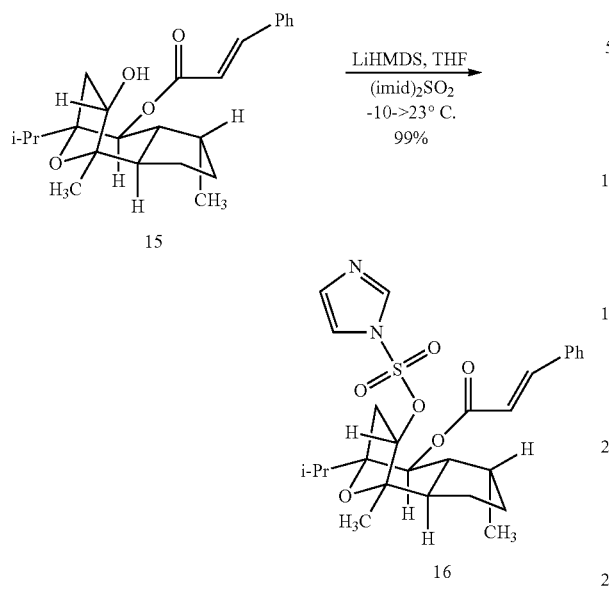

15

16

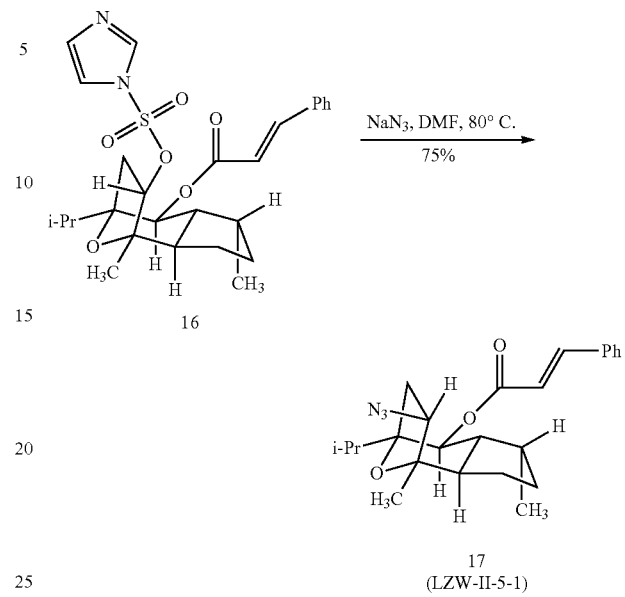

16

17
(LZW-II-5-1)

To prepare compound 16, a solution of n-butyllithium (2.50 M, 72.8 µL, 182 µmol, 7.00 equiv) was added to a stirred solution of hexamethyldisilazane (42 µL, 200 µmol, 7.70 equiv) in tetrahydrofuran (2 ml) at 0° C. The resultant solution was warmed briefly to 23° C., then was cooled to 0° C. whereupon a solution of 15 (10 mg, 26 µmol, 1 equiv) in tetrahydrofuran (1 mL) was added. The resultant mixture was stirred at 0° C. for 30 min, then was cooled to −10° C. whereupon N,N'-sulfuryldiimidazole (40 mg, 200 µmol, 7.70 equiv) was added. The reaction mixture was warmed to 23° C. and stirred at that temperature for 12 h. Excess N,N'-sulfuryldiimidazole was quenched by the addition of methanol (0.2 mL), and the resultant mixture was concentrated. The residue was partitioned between saturated aqueous sodium bicarbonate solution (5 mL) and dichloromethane (5 ml). The layers were separated and the aqueous phase was extracted with dichloromethane (3×5 ml). The combined organic layers were dried over anhydrous sodium sulfate and the dried solution was concentrated. Purification of the residue by flash column chromatography (20% ethyl acetate-hexanes) gave 16 (13 mg, quantitative) as a colorless oil. Imidazole 16: TLC: 20% ethyl acetate-hexanes, $R_f$=0.35 (UV, CAM). $[\alpha]_D^{23}$=−14.0° (c=0.71, CHCl$_3$). $^1$H NMR (300 MHz, CDCl$_3$). δ: 8.03 (s, 1H), 7.65 (d, J=16.1 Hz, 1H), 7.56-7.53 (m, 2H), 7.41-7.38 (m, 4H), 7.24 (s, 1H), 6.38 (d, J=16.4 Hz, 1H), 5.20 (d, J=10.1 Hz, 1H), 4.59 (dd, J1=10.7 Hz, J2=4.8 Hz, 1H), 2.31-2.22 (m, 1H), 2.18-2.13 (m, 2H), 2.06-1.99 (m, 2H), 1.92-1.88 (m, 1H), 1.83-1.67 (m, 3H), 1.23-1.21 (m, 1H), 1.19 (s, 3H), 0.95-0.89 (m, 9H). $^{13}$C NMR (75 MHz, CDCl$_3$). δ: 165.8, 145.7, 137.4, 134.4, 131.8, 130.7, 129.2, 128.4, 118.2, 117.9, 90.7, 85.4, 81.3, 71.3, 49.0, 46.5, 35.9, 32.8, 31.4, 31.3, 24.1, 22.7, 17.7, 17.0, 17.0. FTIR (NaCl, thin film), cm$^{-1}$ 2960, 1713, 1636. HRMS: ESI [M+H]$^+$ Calcd. for $C_{27}H_{35}N_2O_6S$: 515.2210. Found: 515.2215.

To prepare compound 17, dodium azide (25.0 mg, 380 µmol, 20.0 equiv) was added in one portion to a stirred solution of 16 (10.0 mg, 19.0 µmol, 1 equiv) in N,N-dimethylformamide (2 ml). The resultant mixture was heated at 80° C. for 2 d. The reaction mixture was cooled, diluted with dichloromethane (10 ml) and washed with water (10 ml). The aqueous layer was extracted with dichloromethane (3×5 mL), the combined organic layers were dried over anhydrous sodium sulfate, and the dried solution was concentrated. Purification of the residue by flash column chromatography (2% ethyl acetate-hexanes) afforded 17 (LZW II-5-1, 6.0 mg, 75%) as a colorless oil. 17 (LZW II 5-1): TLC: 4% ethyl acetate-hexanes, $R_f$=0.50 (UV, KMnO4). $[\alpha]_D^{23}$=−37.7° (c=0.5, CHCl$_3$). $^1$H NMR: (500 MHz, CDCl$_3$). δ: 7.67 (d, J=16.0 Hz, 1H), 7.54-7.52 (m, 2H), 7.40-7.38 (m, 3H), 6.50 (d, J=16.0 Hz, 1H), 5.13 (d, J=10.3 Hz, 1H), 3.64 (dd, J=8.4, 3.4, 1H), 2.60 (dd, J=14.4, 8.5 Hz, 1H), 2.15-2.10 (m, 1H), 1.95-1.89 (m, 3H), 1.81-1.70 (m, 2H), 1.50-1.44 (m, 1H), 1.33 (s, 3H), 1.30-1.24 (m, 2H), 1.03 (d, J=6.8 Hz, 3H), 0.98 (d, J=7.0 Hz, 3H), 0.94 (d, J=7.0 Hz,' 3H). $^{13}$C NMR: (125 MHz, CDCl$_3$). δ: 165.6, 145.2, 134.2, 130.4, 128.9, 128.1, 117.9, 85.6, 85.4, 71.3, 63.3, 48.1, 46.9, 38.7, 32.9, 31.1, 30.9, 24.7, 20.2, 18.2, 17.5, 17.0. FTIR (NaCl, thin film), cm$^{-1}$: 2930, 2092, 1711, 1640. HRMS: ESI [M+H]$^+$ Calcd. for $C_{24}H_{31}N_3O_3$: 410.2438. Found: 410.2443.

The following describes a preparation of compound 9.

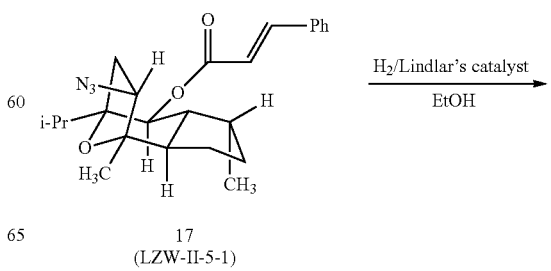

17
(LZW-II-5-1)

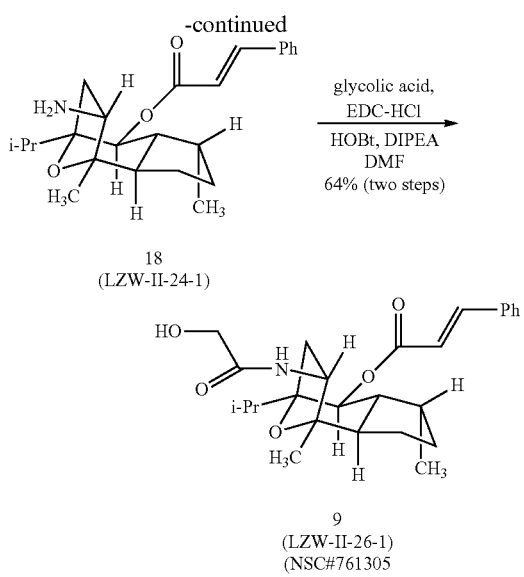

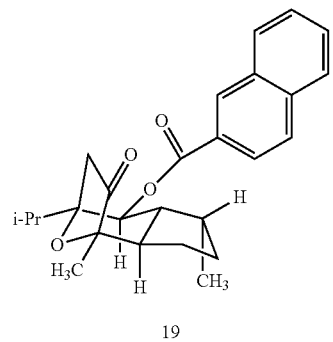

The following describes a preparation of compound 19.

To prepare compound 9, Lindlar's catalyst (5 mg) was added to a stirred solution of 17 (LZW-11-5-1, 9.0 mg, 22 µmol, 1 equiv) in ethanol (2 ml). The resultant mixture was bubbled with hydrogen (H$_2$, balloon) for 5 minutes and then stirred under a hydrogen atmosphere at room temperature for 30 min. The reaction mixture was then filtered through a pad of Celite, and the filtrate was concentrated. Purification of the residue by flash column chromatography (2% triethylamine-ethyl acetate) afforded 18 (lZW-11-24-1, which was advanced without further characterization) as a colorless oil.

Glycolic acid (26.0 mg, 350 µmol, 16.0 equiv), N (3-Dimethylaminopropyl)-N'-ethylcarbodiimide hydrochloride (67.0 mg, 350 µmol, 16.0 equiv) and 1-hydroxybenzotriazole (47.0 mg, 350 µmol, 16.0 equiv) were added sequentially to a stirred solution of 18 (lZW-II-24-1) in N,N-dimethylformamide (4 ml) at 23° C. The reaction mixture was cooled to 0° C. whereupon N,N-diisopropylethylamine (152 µL, 880 µmol, 40 equiv) was added. The resultant mixture was stirred at 0° C. for 1 h, then allowed to warm to 23° C. and stirred for an additional 24 h. The reaction mixture was diluted with water (10 ml), and the aqueous layer was extracted with dichloromethane (3×5 ml). The combined organic layers were dried over anhydrous sodium sulfate and the dried solution was concentrated. Purification of the residue by flash column chromatography (67% ethyl acetate-hexanes) afforded 9 (lZW-II-26-1, 6.0 mg, 64% two steps) as a colorless oil. 9 (LZW-11-26-1, NCI-NSC#761305): TLC: 67% ethyl acetate-hexanes, R$_f$=0.50 (UV, CAM). [α]$_D^{23}$=−37° (c=0.4, MeOH). $^1$H NMR: (500 MHz, MeOH-d$_4$), δ: 7.69 (d, J=15.9 Hz, 1H), 7.62-7.60 (m. 2H), 7.41-7.39 (m, 3H), 6.50 (d, J=16.0 Hz, 1H), 5.13 (d, J 9.6 Hz, 1H), 4.43 (dd, J 9.1, 4.2, 1H), 4.00 (d, J=4.3 Hz; 2H), 2.71 (dd, J=14.1, 9.1 Hz, 1H), 2.15-2.11 (m, 1H), 2.04-1.96 (m, 1H), 1.92-1.87 (m, 1H), 1.80-1.76 (m, 2H), 1.72-1.66 (m, 3H), 1.41-1.36 (m, 1H), 1.30-1.27 (m, 2H), 1.14 (s, 3H), 1.04 (d, J=6.8 Hz, 3H), 0.96 (d. J=7.1 Hz, 3H), 0.93 (d, J=7.2 Hz, 3H). $^{13}$C NMR: (125 MHz, MeOH-d$_4$), δ: 174.1, 167.4, 146.8, 135.7, 131.7, 130.0, 129.3, 118.9, 86.4, 86.2, 72.7, 62.4, 52.0, 49.6, 47.9, 40.9, 34.7, 32.4, 32.0, 25.4, 20.1 18.7, 17.8, 17.3. FTIR (NaCl, thin film), cm$^{-1}$: 3399, 2961, 1709, 1665, 1532. HRMS: ESI [M+H]$^+$ Calcd. for C$_{26}$H$_{35}$NO$_5$: 442.2588. Found: 442.2567.

To prepare compound 19, 2-naphthoyl chloride (59 mg, 0.31 mmol, 3.0 equiv) and 4-(dimethylamino)pyridine (38 mg, 0.31 mmol, 3.0 equiv) were added sequentially to a solution of 7 (26 mg, 0.10 mmol, 1.0 equiv) in 2:1 dichloromethane:triethylamine (30 ml). The reaction mixture was stirred at 23° C. for 2 d, and the excess acid chloride was quenched by the addition of 1N aqueous hydrochloric acid solution (20 ml). The layers were separated and the aqueous layer was extracted with dichloromethane (3×20 ml). The combined organic extracts were washed with saturated aqueous sodium bicarbonate solution (20 ml), dried over anhydrous sodium sulfate, and the dried solution was concentrated. The resulting residue was purified by flash column chromatography (5% ethyl acetate-hexanes) to afford 19 as a pale yellow oil (17 mg. 41%). Ketoester 19: TLC: 20% ethyl acetate-hexanes, R$_f$=0.68 (UV, CAM). $^1$H NMR (500 MHz, CDCl$_3$), δ: 8.55 (s, 1H), 8.00 (d, J=8.5 Hz, 1H), 7.95 (d, J=8.0 Hz, 1H), 7.89 (d, J=9.0 Hz, 2H), 7.63-7.55 (m, 2H), 5.57 (d, J=10.5 Hz, 2H), 2.65 (ab, 1H), 2.15-2.11 (m, 1H), 2.05-1.99 (m, 1H), 1.93-1.85 (m, 2H), 1.73-1.67 (m, 2H), 1.30 (s, 3H), 1.27-1.22 (m, 2H), 1.07 (d, J=7.0 Hz, 3H), 1.03 (d, J=7.0 Hz, 3H), 0.99 (d, J 7.0 Hz, 3H). $^{13}$C NMR (500 MHz, CDCl$_3$). δ: 215.3, 165.2, 135.6, 132.4, 131.2, 129.3, 128.5, 128.3, 127.8, 127.0, 126.8, 125.1, 83.6, 82.5, 71.3, 48.4, 46.2, 42.9, 33.1, 31.1, 30.7, 29.7, 23.3, 17.9, 17.6, 16.9. FTIR (NaCl, thin film), cm$^1$: 2925, 1715, 1631, 1276, 1196, 778. HRMS: APCI ESI [M+]$^+$ Calcd. for C$_{26}$H$_{31}$O$_4$: 407.2222. Found: 407.2226.

The following describes a preparation of compound 20.

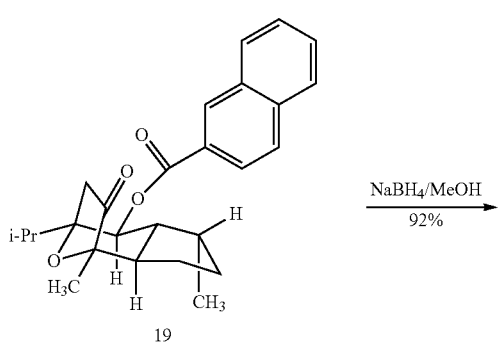

-continued

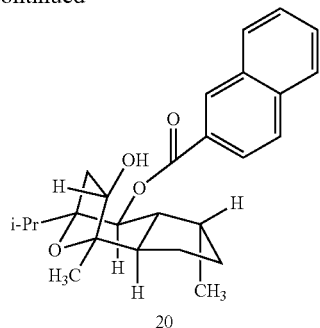

20

To prepare compound 20, sodium borohydride (15 mg, 0.40 mmol, 3.0 equiv) was added to a solution of 19 (54 mg, 0.13 mmol, 1.0 equiv) in methanol (25 mL) at 0° C. The resultant mixture was stirred at 0° C. for 1 h, and the excess borohydride was quenched by the addition of saturated aqueous ammonium chloride solution (25 mL). The mixture was extracted with dichloromethane (3×20 mL), the combined organic layers were dried over anhydrous sodium sulfate, and the dried solution was concentrated. Purification of the residue by flash column chromatography (20% ethyl acetate-hexanes) afforded 20 (50 mg, 92%) as a colorless oil. Hydroxy ester 20: TLC: 20% ethyl acetate-hexanes, $R_f$=0.36 (UV, CAM). $^1$H NMR (500 MHz, CDCl$_3$), δ: 8.58 (s, 1H), 8.05 (d, J=9.0 Hz, 1H), 7.95 (d, J=8.0 Hz, 1H), 7.88 (d, J=8.5 Hz, 2H), 7.61-7.53 (m, 2H), 5.42 (d, J=10.5 Hz, 2H), 4.25 (dd, J$_1$=11.0 Hz, J$_2$=5.0 Hz, 1H), 2.54-2.48 (m, 1H), 2.43 (dd, J$_1$=13.5 Hz, J$_2$=11.0 Hz, 1H), 2.25 (dd, J$_1$=13.5 Hz, J$_2$=5.0 Hz, 1H), 2.19-2.15 (m, 2H), 2.05-1.83 (m, 6H), 1.36 (s, 3H), 1.32-1.20 (m, 2H), 1.00 (d, J=7.0 Hz, 3H), 0.98 (d, J=7.0 Hz, 3H), 0.95 (d, J=7.0 Hz, 3H). $^{13}$C NMR (500 MHz, CDCl$_3$), δ: 165.4, 135.5, 132.5, 131.1, 129.3, 128.2, 128.1, 127.7, 127.6, 126.6, 125.3, 84.7, 81.5, 81.1, 73.0, 49.2, 46.3, 39.5, 33.0, 31.5, 31.1, 29.7, 24.4, 23.3, 17.8, 17.0. FTIR (NaCl, thin film), cm$^{-1}$: 2924, 1714, 1631, 1276, 1196, 778. HRMS: APCI ESI [M+H]$^+$ Calcd. for C$_{26}$H$_{33}$O$_4$: 409.2379. Found: 409.2364.

The following describes a preparation of compound 21.

To prepare compound 21, a solution of n-butyllithium (2.50 M in hexanes, 340 μL, 0.86 mmol, 7.00 equiv) was added to a stirred solution of hexamethyldisilazane (230 μL, 0.94 mmol, 7.70 equiv) in tetrahydrofuran (15 mL) at 0° C. The resultant solution was warmed briefly to 23° C., then was cooled to 0° C. whereupon a solution of 20 (50 mg, 0.12 mmol, 1 equiv) in tetrahydrofuran (5 ml) was added. The resultant mixture was stirred at 0° C. for 30 min, then was cooled to −10° C. whereupon N,N'-sulfuryldiimidazole (218 mg, 1.10 mmol, 9.00 equiv) was added. The reaction mixture was warmed to 23° C. and stirred at that temperature for 12 h. Excess N,N'-sulfuryldiimidazole was quenched by the addition of methanol (5 ml), and the resultant mixture was concentrated. The residue was partitioned between saturated aqueous sodium bicarbonate solution (20 ml) and dichloromethane (20 ml). The layers were separated and the aqueous phase was extracted with dichloromethane (3×25 ml). The combined organic layers were dried over anhydrous sodium sulfate and the dried solution was concentrated. Purification of the residue by flash column chromatography (20% ethyl acetate-hexanes) gave 21 (39 mg, 60%) as a colorless oil. Imidazole 21: TLC: 20% ethyl acetate-hexanes, $R_f$=0.33 (UV, CAM). $^1$H NMR (500 MHz, CDCl$_3$), δ: 8.53 (s, 1H), 8.07 (s, 1H), 8.02 (d. J=8.0 Hz, 1H), 7.98 (d, J=8.5 Hz, 1H), 7.90 (d, J=8.5 Hz, 2H), 7.63-7.58 (m, 2H), 7.42 (s, 1H), 7.28 (s, 1H), 5.38 (d, J=9.5 Hz, 2H), 4.64 (dd, J1=11.0 Hz, J2=5.0 Hz, 1H), 2.37 (dd, J$_1$ 14.5 Hz, J$_2$=11.0 Hz, 1H), 2.27-2.22 (m, 1H), 2.19-2.14 (m, 2H), 2.02-1.90 (m, 2H), 1.83-1.77 (m, 1H), 1.74-1.60 (m, 2H), 1.28-1.24 (m, 1H), 1.22 (s, 3H), 0.98 (d, J=7.0 Hz, 3H), 0.94 (d, J=7.0 Hz, 3H), 0.92 (d, J=7.0 Hz, 3H). $^{13}$C NMR (500 MHz, CDCl$_3$), δ: 165.2, 135.6, 132.5, 131.2, 129.4, 128.5, 128.3, 127.8, 127.0, 126.8, 125.2, 90.5, 85.0, 81.2, 71.6, 48.9, 46.4, 35.7, 32.7, 31.2, 31.1, 29.7, 23.9, 22.5, 17.5, 16.8. FTIR (NaCl, thin film), cm$^{-1}$: 2920, 1715, 1632, 1198, 778. HRMS: ESI [M+H]$^+$ Calcd. for C$_{29}$H$_{34}$N$_2$NaO$_6$S: 561.2035. Found: 561.2025.

The following describes a preparation of compound 22.

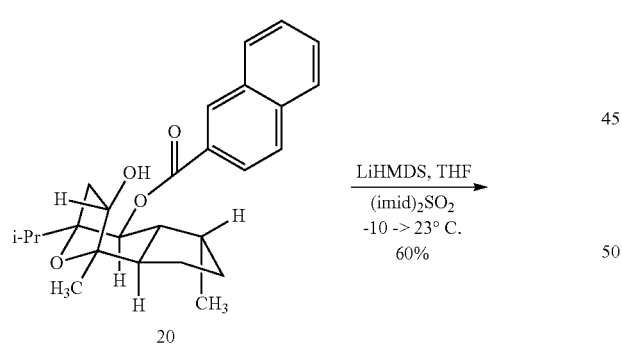

20

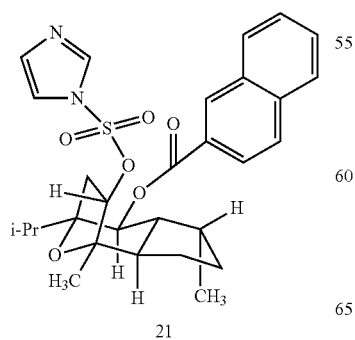

21

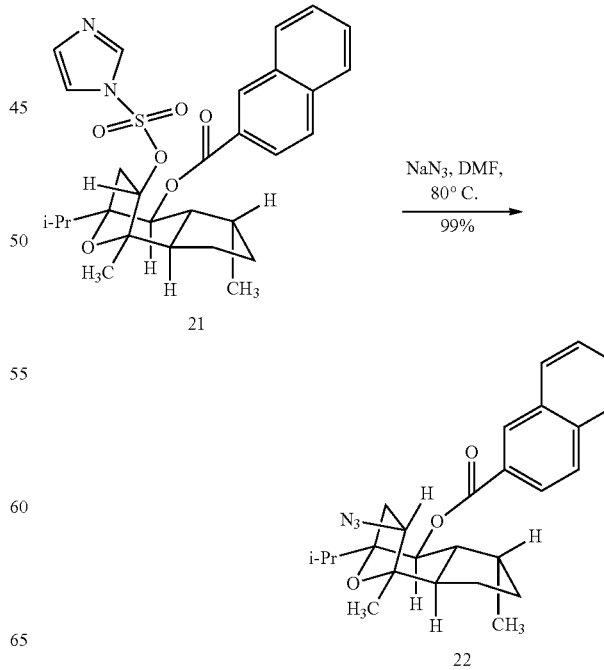

22

To prepare compound 22, sodium azide (94.0 mg, 1.44 mmol, 20.0 equiv) was added to a solution of 21 (39.0 mg, 72.4 µmol, 1.0 equiv) in N,N-dimethylformamide (5 ml). The reaction mixture was heated at 80° C. for 18 h, and quenched by the addition of 10% aqueous lithium chloride solution (20 mL). The mixture was extracted with dichloromethane (3×25 ml), the combined organic layers were dried over anhydrous sodium sulfate, and the dried solution was concentrated. Purification of the residue by flash column chromatography (5% ethyl acetate-hexanes) afforded the azide 22 (31 mg, 99%) as a colorless oil. Azide 22: TLC: 20% ethyl acetate-hexanes, $R_f$=0.66 (UV, CAM). $^1$H NMR (500 MHz, CDCl$_3$), δ: 8.56 (s, 1H), 8.02 (d, J=8.5 Hz, 1H), 7.96 (d, J=8.0 Hz, 1H), 7.89 (d, J=8.5 Hz, 2H), 7.63-7.55 (m, 2H), 5.32 (d, J=10.0 Hz, 2H), 3.72 (dd, J$_1$=8.5 Hz, J$_2$=3.5 Hz, 1H), 2.77 (dd, J$_1$=14.0 Hz, J$_2$=8.5 Hz, 1H), 2.17-2.13 (m, 1H), 2.05-2.0 (m, 1H), 1.99-1.92 (m, 2H), 1.88-1.75 (m, 3H), 1.63-1.60 (m, 2H), 1.37 (s, 3H), 1.05 (d, J=7.0 Hz, 3H), 1.00 (d, J=7.0 Hz, 3H), 0.90 (d, J=7.0 Hz, 3H). $^{13}$C NMR (500 MHz, CDCl$_3$), δ: 165.2, 135.6, 132.5, 131.1, 129.3, 128.3, 128.2, 127.8, 127.3, 126.8, 125.2, 85.7, 85.5, 71.9, 63.4, 48.2, 47.0, 38.9, 33.0, 31.1, 30.9, 29.7, 24.8, 20.2, 18.3, 17.5, 17.0. FTIR (NaCl, thin film), cm$^{-1}$ 2957, 2927, 2094, 1720, 1276, 1195. HRMS: APCI [M+H]$^+$ Calcd. for C$_{26}$H$_{32}$N$_3$O$_3$: 434.2444. Found: 434.2459.

The following describes a preparation of compound 12.

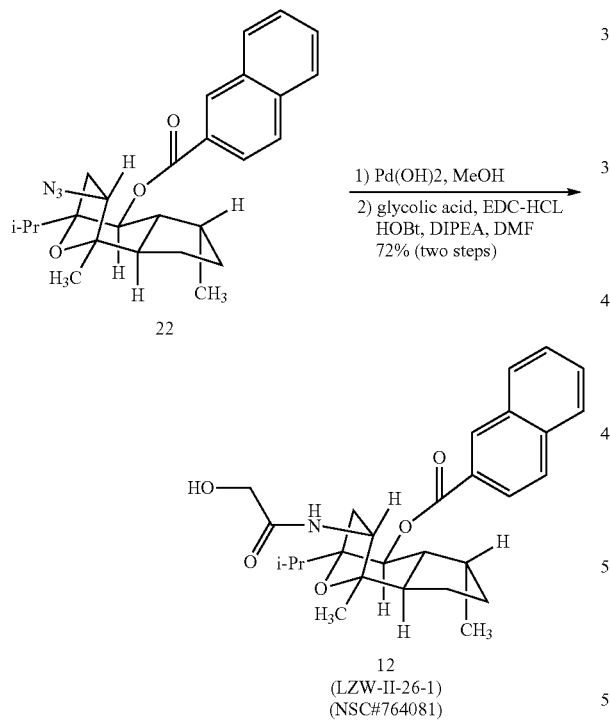

12
(LZW-II-26-1)
(NSC#764081)

To prepare compound 12, palladium hydroxide on carbon (Pearlman's catalyst, (1.4 mg, 20 wt % loading) was added to a solution of 22 (7.0 mg, 16 mol, 1.0 equiv) in methanol (5 ml). The reaction mixture was bubbled with hydrogen (H$_2$, balloon) for 10 min, and was then stirred under a hydrogen atmosphere (balloon) for 5 h. The reaction flask was purged with argon, the reaction mixture was filtered through a pad of Celite, and the pad was washed with methanol. The combined organic filtrates were concentrated and the resultant oily residue was dissolved in N,N-dimethylformamide (10 ml). Glycolic acid (12.0 mg, 0.161 mmol, 10.0 equiv), N-(3-dimethylaminopropyl)-N-ethylcarbodiimide hydrochloride (31.0 mg, 0.161 mmol, 10.0 equiv), and 1-hydroxybenzotriazole (22.0 mg, 0.161 mmol, 10.0 equiv) were added sequentially to the stirred solution at 23° C. The reaction mixture was cooled to 0° C. whereupon N,N-diisopropylethylamine (84 µL, 0.48 mmol, 30 equiv) was added. The resultant mixture was stirred at 0° C. for 1 h, then allowed to warm to 23° C. and stirred for an additional 18 h. The reaction mixture was quenched with 10% aqueous lithium chloride solution (20 ml) then extracted with dichloromethane (3×25 ml). The combined organic layers were dried over anhydrous sodium sulfate and the dried solution was concentrated. Purification of the residue by flash column chromatography (50% ethyl acetate-hexanes) afforded the glycolamide 12 (5.4 mg, 72% over two steps) as a colorless oil. Glycolamide 12: TLC: 50% ethyl acetate-hexanes, $R_f$ 0.20 (UV, CAM). $^1$H NMR (500 MHz, CD$_3$OD), δ: 8.56 (s, 1H), 8.02 (d, J=8.7 Hz, 1H), 7.96 (d, J=7.5 Hz, 1H), 7.88 (d, J=8.4 Hz, 2H), 7.63-7.53 (m, 2H), 6.52 (d, J=9.6 Hz, 2H), 4.58-4.50 (m, 1H), 4.17 (s, 3H), 3.51 (bs, 1H), 2.90 (dd, J$_1$=14.4 Hz, J$_2$=9.0 Hz, 1H), 2.33-2.28 (m, 1H), 2.20-2.13 (m, 1H), 1.99-1.65 (m, 7H), 1.38-1.31 (m, 2H), 1.22 (s, 3H), 1.04 (d, J=6.6 Hz, 3H), 0.98 (d, J=6.9 Hz, 3H), 0.97 (d, J=6.9 Hz, 3H). $^{13}$C NMR (500 MHz, CD$_3$OD), δ: 174.1, 166.9, 137.1, 134.0, 132.2, 130.4, 129.7, 129.5, 128.9, 128.6, 128.0, 126.1, 86.5, 86.3, 73.3, 62.4, 52.2, 49.7, 48.0, 41.2, 34.9, 32.5, 32.1, 25.5, 20.1, 18.8, 17.8, 17.3. FTIR (NaCl, thin film), cm$^{-1}$ 2954, 2926, 1714, 1659, 1276, 1196, 1096, 968. HRMS: APC [M+H]$^+$ Calcd. for C$_{26}$H$_{36}$NO$_5$: 466.2588. Found: 466.2607.

The following describes a preparation of compound 23.

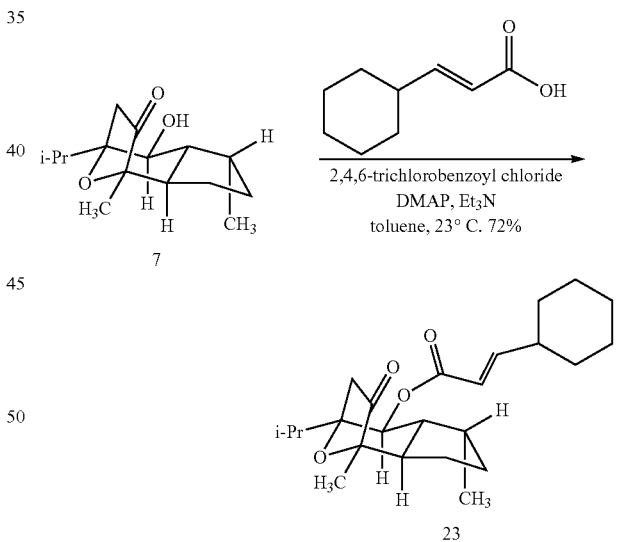

To prepare compound 23, (E)-3-cyclohexylacrylic acid (45 mg, 0.29 mmol, 2.0 equiv), triethylamine (61 µl, 0.44 mmol, 3.0 equiv), 2,4,6-trichlorobenzoyl chloride (57 µL, 0.37 mmol, 2.5 equiv), and 4-(dimethylamino)pyridine (3.6 mg, 29 µmol, 0.2 equiv) were added sequentially to a solution of 7 (37 mg. 0.15 mmol, 1.0 equiv) in toluene (30 ml). The reaction mixture was stirred at 23° C. for 2 d, then excess acid chloride was quenched with 1N aqueous hydrochloric acid solution (20 ml). The layers were separated and the aqueous layer was extracted with dichloromethane (3×20 ml). The combined organic extracts were washed with saturated aqueous sodium bicarbonate solution (20 ml), dried over anhydrous sodium sulfate, and the dried solution was concentrated. The resulting residue was purified by flash column chromatography (5% ethyl acetate-hexanes) to give 23 as a pale yellow oil (41 mg, 72%). Ketoester 23: TLC: 20% ethyl acetate-hexanes, $R_f$=0.69 (CAM). $^1$H NMR (500 MHz, CDCl$_3$). δ: 6.90 (dd, J$_1$=15.5 Hz, J$_2$=7.0 Hz, 1H), 5.70 (d, J=15.5 Hz, 1H), 5.29 (d, J=10.5 Hz, 1H), 2.47 (ab, 1H), 2.14-2.06 (m, 2H), 1.95-1.86 (m, 2H), 1.78-1.75 (m, 4H), 1.69-1.64 (m, 2H), 1.52-1.49 (m, 1H), 1.43 (s, 3H), 1.33-1.28 (m, 2H), 1.21-1.12 (m, 4H), 1.02 (d, J=7.0 Hz, 3H), 0.99 (d, J=7.0 Hz, 3H), 0.92 (d, J=7.0 Hz, 3H). $^{13}$C NMR (500 MHz, CDCl$_3$). δ: 215.4, 165.6, 155.4, 118.4, 83.5, 82.4, 70.3, 48.3, 46.0, 42.7, 40.5, 33.0, 31.6, 31.0, 30.7, 30.3, 29.7, 25.9, 25.7, 23.2, 17.9, 17.5, 16.9, 16.8. FTIR (NaCl, thin film), cm$^{-1}$: 2927, 2853, 1722, 1651. HRMS: APCI [M+H]$^+$ Calcd. for C$_{24}$H$_{37}$O$_4$: 389.2692. Found: 389.2661.

The following describes a preparation of compound 24.

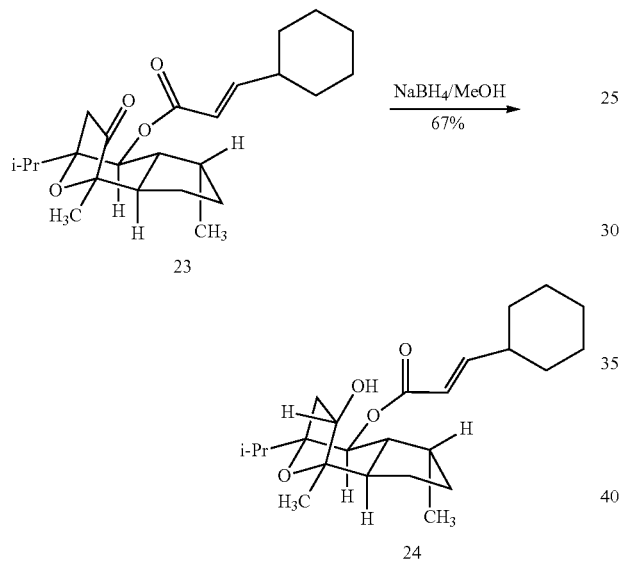

To prepare compound 24, sodium borohydride (30 mg, 0.78 mmol, 4.0 equiv) was added to a solution of 23 (76 mg, 0.20 mmol, 1.0 equiv) in methanol (40 ml) at 0° C. The resultant mixture was stirred at 0° C. for 30 min, and then the excess sodium borohydride was quenched by the addition of saturated aqueous ammonium chloride solution (25 ml). The mixture was extracted with dichloromethane (3×20 ml), the combined organic layers were dried over anhydrous sodium sulfate, and the dried solution was concentrated. Purification of the residue by flash column chromatography (20% ethyl acetate-hexanes) afforded 24 (41 mg, 67%) as a colorless oil. Hydroxyester 24: TLC: 20% ethyl acetate-hexanes, $R_f$=0.30 (CAM); $^1$H NMR (500 MHz, CDCl$_3$), δ: 6.88 (dd, J$_1$=16.0 Hz, J$_2$=6.5 Hz, 1H), 5.72 (d. J=16.0 Hz, 1H), 5.13 (d, J=10.5 Hz, 1H), 4.18-4.15 (m, 1H), 2.31-2.26 (m, 2H), 2.14-2.09 (m, 2H), 2.04-2.00 (m, 1H), 1.63-1.75 (m, 6H), 1.68-1.60 (m, 2H), 1.30 (s, 3H), 1.22-1.12 (m, 4H), 0.94 (d, J=6.5 Hz, 3H), 0.92 (d, J=7.0 Hz, 3H), 0.91 (d, J=7.0 Hz, 3H); $^{13}$C NMR (500 MHz, CDCl$_3$), δ: 165.9, 154.5, 119.0, 84.5, 81.0, 72.0, 54.3, 49.1, 46.2, 40.4, 39.3, 32.8, 32.2, 31.7, 31.4, 31.1 25.9, 25.7, 24.3, 23.3, 17.7[M+H]$^+$ Calcd. for C$_{24}$H$_{39}$O$_4$: 391.2848. Found: 391.2845.

The following describes a preparation of compound 25.

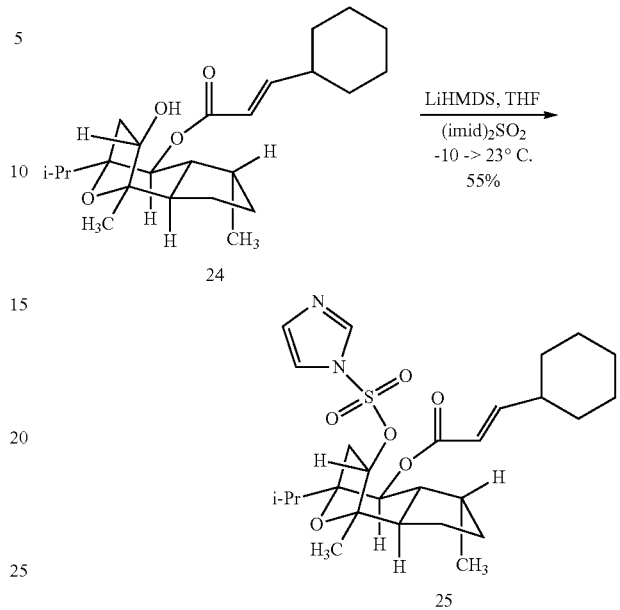

To prepare compound 25, a solution of n-butyllithium (2.50 M in hexanes, 0.33 ml, 0.82 mmol, 7.00 equiv) was added to a stirred solution of hexamethyldisilazane (0.19 ml, 0.91 mmol, 7.7 equiv) in tetrahydrofuran (10 mL) at 0° C. The resultant solution was warmed briefly to 23° C., then was cooled to 0° C. whereupon a solution of 24 (46 mg, 0.12 mmol, 1.0 equiv) in tetrahydrofuran (5 ml) was added. The resultant mixture was stirred at 0° C. for 30 min, then was cooled to −10° C. whereupon N,N'-sulfuryldiimidazole (210 mg, 1.06 mmol, 9.00 equiv) was added. The reaction mixture was warmed to 23° C. and stirred at that temperature for 12 h. Excess N,N-sulfuryldiimidazole was quenched by the addition of methanol (5 ml), and the resultant mixture was concentrated. The residue was partitioned between saturated aqueous bicarbonate solution (20 ml) and dichloromethane (20 ml). The layers were separated and the aqueous phase was extracted with dichloromethane (3×25 ml). The combined organic layers were dried over anhydrous sodium sulfate and the dried solution was concentrated. Purification of the residue by flash column chromatography (20% ethyl acetate-hexanes) gave 25 (34 mg, 55%) as a colorless oil. Imidazole 25: TLC: 20% ethyl acetate-hexanes, $R_f$0.32 (UV, CAM). $^1$H NMR (500 MHz, CDCl$_3$). δ: 8.02 (s, 1H), 7.37 (s, 1H), 7.23 (s, 1H), 6.89 (dd, J$_1$=16.0 Hz, J$_2$ 6.5 Hz, 1H), 5.79 (d, J=16.0 Hz, 1H), 5.11 (d, J=10.0 Hz, 1H), 4.56 (dd, J1=11.0 Hz, J2=5.0 Hz, 1H), 2.27-2.20 (m, 1H), 2.15-2.05 (m, 4H), 2.01-1.95 (m, 2H), 1.87-1.83 (m, 1H), 1.78-1.75 (m, 6H), 1.68-1.65 (m, 3H), 1.60-1.54 (m, 3H), 1.17 (s, 3H), 0.91-0.87 (m, 12H). $^{13}$C NMR (500 MHz, CDCl$_3$). δ: 165.6, 155.3, 131.6, 118.4, 90.5, 85.2, 81.0, 70.6, 48.7, 46.2, 40.5, 35.6, 32.5, 31.9, 31.6, 31.1, 30.3, 29.7, 25.9, 25.7, 23.9, 22.4, 17.4, 16.7. FTIR (NaCl, thin film), cm$^{-1}$ 2924, 2852, 1720, 1648, 1423. HRMS: ESI [M+]$^+$ Calcd. for C$_{27}$H$_{40}$N$_2$NaO$_6$S: 543.2505. Found: 543.2476.

The following describes a preparation of compound 26.

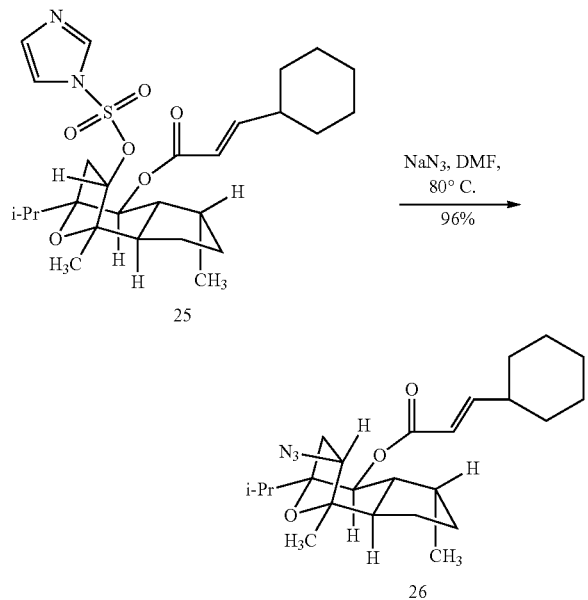

To prepare compound 26, sodium azide (85 mg, 1.3 mmol, 20 equiv) was added in one portion to a solution of 25 (34 mg, 65 μmol, 1.0 equiv) in N,N-dimethylformamide (5 mL). The reaction mixture was heated at 80° C. for 18 h. and then quenched with 10% aqueous lithium chloride solution (20 mL). The mixture was extracted with dichloromethane (3×20 mL), the combined organic layers were dried over anhydrous sodium sulfate, and the dried solution was concentrated. Purification of the residue by flash column chromatography (5% ethyl acetate-hexanes) afforded the azide 26 (26 mg, 96%) as a colorless oil. Azide 26: TLC: 20% ethyl acetate-hexanes, $R_f$=0.74 (CAM). $^1$H NMR (500 MHz, CDCl$_3$). δ: 6.89 (dd, $J_1$ 16.0 Hz, $J_2$=6.5 Hz, 1H), 5.71 (d, J 15.5 Hz, 1H), 5.04 (d, J 10.5 Hz, 1H), 3.60 (dd, $J_1$=8.0 Hz, $J_2$=3.0 Hz, 1H), 2.53 (dd, $J_1$=14.5 Hz, $J_2$=8.5 Hz, 1H), 2.14-2.09 (m, 3H), 1.91-1.84 (m, 4H), 1.79-1.72 (m, 6H), 1.70-1.66 (m, 2H), 1.60-1.54 (m, 3H), 1.43-1.40 (m, 1H), 1.31 (s, 3H), 1.00 (d, J=7.0 Hz, 3H), 0.94 (d, J=7.0 Hz, 3H), 0.91 (d, J=7.0 Hz, 3H). $^{13}$C NMR (500 MHz, CDCl$_3$). δ: 165.7, 155.0, 118.6, 85.6, 85.4, 70.9, 63.3, 48.0, 46.9, 40.4, 38.6, 32.8, 31.7, 31.1, 30.9, 25.9, 25.7, 24.7, 20.2, 18.2, 17.5, 16.9. FTIR (NaCl, thin film), cm$^{-1}$ 2928, 2853, 2094, 1722, 1713. HRMS APCI [M+H]$^+$ Calcd. for $C_{24}H_{38}N_3O_3$: 416.2908. Found: 416.2912.

The following describes a preparation of compound 11.

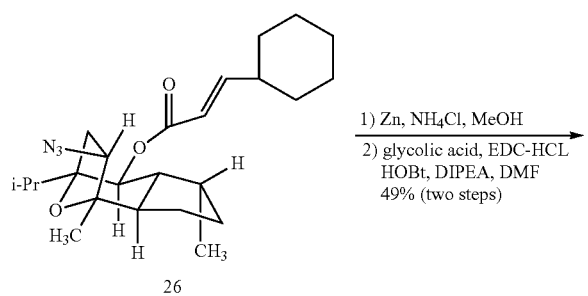

To prepare compound 11, ammonium chloride (5.0 mg, 96 μmol, 10 equiv) and zinc (dust, 6.0 mg, 96 μmol, 10 equiv) were added sequentially to a solution of 26 (4.0 mg, 9.6 μmol, 1.0 equiv) in methanol (3 ml). The reaction mixture was stirred vigorously at room temperature for 2 h, then was concentrated. The resulting residue was triturated with diethyl ether (3×10 mL) and the combined organic fractions were filtered through a pad of silica gel to afford the amine (3.5 mg, 93%), which was advanced without further purification.

Glycolic acid (8.0 mg, 0.10 mmol, 10 equiv), N-(3-dimethylaminopropyl)-N'-ethylcarbodiimide hydrochloride (20.0 mg, 0.103 mmol, 10.0 equiv), and 1-hydroxybenzotriazole (14 mg, 0.10 mmol, 10 equiv) were added sequentially to a stirred solution of the amine intermediate in N,N-dimethylformamide (10 mL) at 23° C. The reaction mixture was cooled to 0° C. whereupon N,N-diisopropylamine (54 μL, 0.31 mmol, 30.0 equiv) was added. The reaction mixture was stirred at 0° C. for 1 h, then allowed to warm to 23° C. and stirred for an additional 18 h. The reaction mixture was quenched with 10% aqueous lithium chloride solution (20 mL), then was extracted with dichloromethane (3×25 mL). The combined organic layers were dried over anhydrous sodium sulfate and the dried solution was concentrated. Purification of the residue by flash column chromatography (50% ethyl acetate-hexanes) afforded the glycolamide 11 (2.1 mg, 49% over two steps) as a colorless oil. Glycolamide 11 (DF-11-141, NSC#768544): TLC: 50% ethyl acetate-hexanes, $R_f$=0.35 (CAM). $^1$H NMR (500 MHz, CDCl$_3$). δ: 6.89 (dd, $J_1$=15.5 Hz, $J_2$=7.0 Hz, 1H), 6.42 (d, J=10.0 Hz, 1H), 5.71 (d, J=15.5 Hz, 1H), 5.03 (d, J 10.5 Hz, 1H), 4.46-4.41 (m, 1H), 4.14 (s, 2H), 2.65 (dd, $J_1$=14.5 Hz, $J_2$=9.0 Hz, 1H), 2.13-2.10 (m, 2H), 2.04-2.00 (m, 4H), 2.04-1.93 (m, 6H), 1.84-1.79 (m, 2H), 1.77-1.75 (m, 5H), 1.16 (s, 3H), 1.14-1.09 (m, 1H), 1.00 (d, J=7.0 Hz, 3H), 0.93 (d, J=7.0 Hz, 3H), 0.91 (d, J=7.0 Hz, 3H). $^{13}$C NMR (500 MHz, CDCl$_3$). δ: 170.1, 166.3, 155.0, 118.7, 85.1, 84.7, 71.0, 62.1, 50.8, 48.1, 46.7, 40.7, 40.4, 33.2, 31.9, 31.7, 30.9, 29.7, 25.9, 25.7, 24.5, 22.7, 20.0, 18.2, 17.5, 16.9. FTIR (NaCl, thin film), cm$^{-1}$ 3358, 2926, 2855, 1719, 1653. HRMS: APCI [M+]$_+$ Calcd. for $C_{26}H_{42}NO_5$: 448.3063. Found: 448.3051.

The following describes a preparation of compound 27.

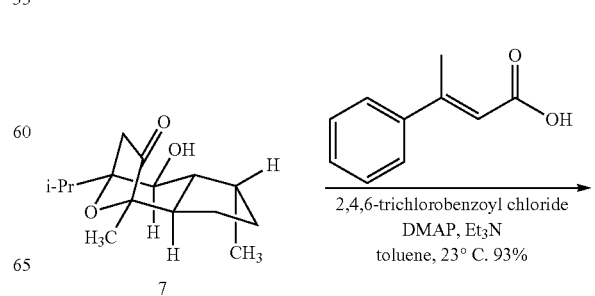

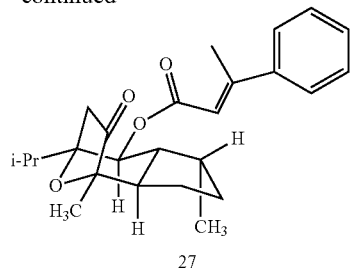

27

To prepare compound 27, (E)-3-phenylbut-2-enoic acid (129 mg, 0.793 mmol, 2.0 equiv), triethylamine (0.17 ml, 1.2 mmol, 3.0 equiv), 2,4,6-trichlorobenzoyl chloride (0.15 ml, 0.99 mmol, 2.5 equiv), and 4-dimethylaminopyridine (10 mg, 79 μmol, 0.2 equiv) were added sequentially to a solution of 7 (0.100 mg, 0.396 mmol, 1.00 equiv) in toluene (50 mL). The reaction mixture was stirred at 23° C. for 2 d, then excess acid chloride was quenched by the addition of 1N aqueous hydrochloric acid solution (20 ml). The layers were separated and the aqueous layer was extracted with dichloromethane (3×20 ml). The combined organic layers were washed with saturated aqueous sodium bicarbonate solution (20 ml), dried over anhydrous sodium sulfate, and the dried solution was concentrated. The resulting residue was purified by flash column chromatography (5% ethyl acetate-hexanes) to afford 27 (146 mg, 93%) as a pale yellow oil. Ketoester 27: TLC: 20% ethyl acetate-hexanes, $R_f$=0.57 (UV, CAM). $^1$H NMR (500 MHz, CDCl$_3$). δ: 7.48-7.47 (m, 2H), 7.38-7.37 (m, 3H), 6.06 (s, 1H), 5.34 (d, J=11.0 Hz, 1H), 2.58 (s, 3H), 2.49 (ab, 1H), 2.15-2.11 (m, 1H), 2.00-1.93 (m, 1H), 1.91-1.78 (m, 2H), 1.68-1.63 (m, 1H), 1.55-1.49 (m, 1H), 1.26 (s, 3H), 1.22-1.19 (m, 2H), 1.05 (d, J=7.0 Hz, 3H), 1.03 (d, J=7.0 Hz, 3H), 0.96 (d, J=7.0 Hz, 3H). $^{13}$C NMR (500 MHz, CDCl$_3$). δ: 215.3, 165.2, 156.6, 142.0, 129.2, 128.5, 126.3, 116.7, 83.5, 82.4, 70.0, 48.4, 46.1, 42.7, 33.0, 31.1, 30.7, 23.3, 18.1, 17.9, 17.5, 16.9. FTIR (NaCl, thin film), cm$^{-1}$ 2955, 2925, 1756, 1717, 1153. HRMS: APCI [M+Y]$^+$ Calcd. for C$_{25}$H$_{33}$O$_4$: 397.2373. Found: 397.2393.

The following describes a preparation of compound 28.

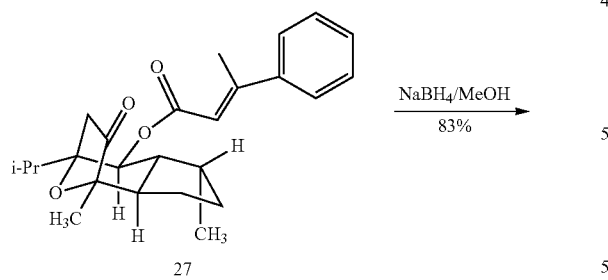

28

To prepare compound 28, sodium borohydride (5.2 mg, 0.14 mmol, 3.0 equiv) was added to a solution of 27 (18 mg. 45 μmol, 1.0 equiv) in methanol (25 ml) at 0° C. The resultant mixture was stirred at 0° C. for 30 min, and then the excess sodium borohydride was quenched by the addition of saturated aqueous ammonium chloride solution (25 ml). The mixture was extracted with dichloromethane (3×20 ml), the combined organic layers were dried over anhydrous sodium sulfate, and the dried solution was concentrated. Purification of the residue by flash column chromatography (20% ethyl acetate-hexanes) afforded 28 (15 mg, 83%) as a colorless oil. Hydroxyester 28: TLC: 20% ethyl acetate-hexanes, $R_f$=0.30 (UV, CAM). $^1$H NMR (500 MHz, CDCl$_3$). δ: 7.49-7.47 (m, 2H), 7.39-7.35 (m, 3H), 6.08 (s, 1H), 5.19 (d, J 10.0 Hz, 1H), 4.17 (dd, J=11.0 Hz, J 5.0 Hz, 1H), 2.58 (s, 3H), 2.36-2.30 (m, 2H), 2.19-2.15 (m, 1H), 2.03 (dd, J=14.0 Hz, J=5.0 Hz, 1H), 1.99-1.93 (m, 1H), 1.85-1.78 (m, 3H), 1.69-1.62 (m, 1H), 1.32 (s, 3H), 1.22-1.19 (m, 1H), 0.98-0.95 (m, 3H). $^{13}$C NMR (500 MHz, CDCl$_3$). δ: 215.3, 165.2, 156.6, 142.0, 129.2, 128.5, 126.3, 116.7, 83.5, 82.4, 70.0, 48.4, 46.1 42.7, 33.0, 31.1 30.7, 23.3, 18.1, 17.9, 17.5, 16.9. FTIR (NaCl, thin film), cm$^{-1}$ 3447, 2964, 2926, 1714, 1626, 1165. HRMS: APCI [M+H]$^+$ Calcd. for C$_{25}$H$_{35}$O$_4$: 399.2535. Found: 399.2519.

The following describes a preparation of compound 29.

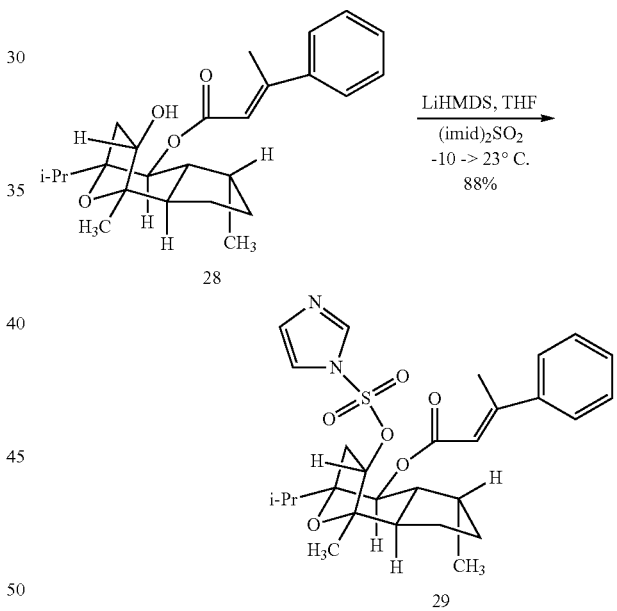

To prepare compound 29, a solution of n-butyllithium (2.50 M in hexanes, 84.0 μL, 0.21 mmol, 7.00 equiv) was added to a stirred solution of hexamethyldisilazane (49 μL, 0.23 mmol, 7.7 equiv) in tetrahydrofuran (5 ml) at 0° C. The reaction mixture was briefly warmed to 23° C. then was cooled to 0° C. whereupon a solution of 28 (12 mg, 30 μmol, 1.0 equiv) in tetrahydrofuran (2 ml) was added. The resultant mixture was stirred at 0° C. for 30 min, then was cooled to −10° C. whereupon N,N'-sulfuryldiimidazole (54 mg, 0.27 mmol, 9.0 equiv) was added. The reaction mixture was warmed to 23° C. and stirred at that temperature for 12 h. Excess N,N-sulfuryldiimidazole was quenched by the addition of methanol (5 ml), and the resultant mixture was concentrated. The residue was partitioned between saturated aqueous bicarbonate solution (20 ml) and dichloromethane (20 ml). The layers were separated and the aqueous phase was extracted with dichloromethane (3×25 mL). The combined organic layers were dried over anhydrous sodium sulfate and the dried solution was concentrated. The residue was purified by flash column chromatography (20% ethyl acetate-hexanes) to afford 29 (14 mg, 88%) as a colorless oil. Imidazole 29: TLC: 20% ethyl acetate-hexanes, $R_f$=0.33 (UV, CAM). $^1$H NMR (500 MHz, CDCl$_3$) δ: 8.01 (s, 1H), 7.49-7.47 (m, 3H), 7.39-7.35 (m, 4H), 7.22 (s, 1H), 6.06 (s, 1H), 5.16 (d, J=10.5 Hz, 1H), 4.57 (dd, J=11.0 Hz, J 4.5 Hz, 1H), 2.57 (s, 3H), 2.27-2.16 (m, 2H), 2.12-2.08 (dd, J=14.5 Hz, J=4.5 Hz, 1H), 2.04-1.94 (m, 2H), 1.89-1.83 (m, 1H), 1.76-1.67 (m, 3H), 1.23-122 (m, 1H), 1.19 (s, 3H), 0.95 (d, J=7.0 Hz, 3H), 0.93 (d, J=6.5 Hz, 3H), 0.92 (d, J=7.0 Hz, 3H). $^{13}$C NMR (500 MHz, CDCl$_3$). δ: 165.2, 156.5, 142.0, 137.1, 131.6, 129.2, 128.5, 126.3, 117.9, 116.8, 90.5, 85.3, 81.1, 70.4, 48.8, 46.4, 35.7, 32.5, 31.1, 29.7, 24.0, 22.5, 18.1, 17.4, 16.8. FTIR (NaCl, thin film), cm$^{-1}$ 2925, 2854, 1718, 1627, 1423, 1203, 1158. HRMS: ESI [M+H]$^+$ Calcd. for $C_{28}H_{37}N_2O_6S$: 529.2367. Found: 529.2346.

The following describes a preparation of compound 30.

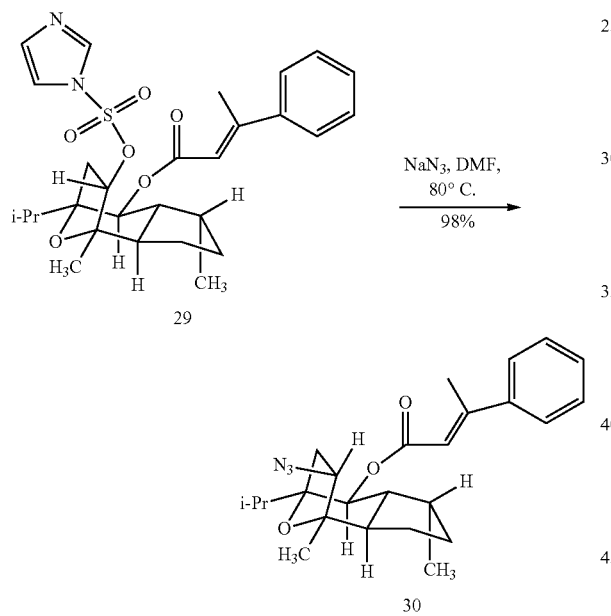

To prepare compound 30, sodium azide (44.0 mg, 0.530 mmol, 20.0 equiv) was added in one portion to a solution of 29 (14 mg, 27 μmol, 1.0 equiv) in N,N-dimethylformamide (5 ml). The reaction mixture was heated at 80° C. for 2 d, and then quenched by the addition of 10% aqueous lithium chloride solution (20 ml). The mixture was extracted with dichloromethane (3×25 ml), the combined organic layers were dried over anhydrous sodium sulfate, and the dried solution was concentrated. Purification of the residue by flash column chromatography (5% ethyl acetate-hexanes) afforded the azide 30 (11 mg, 98%) as a colorless oil. Azide 30: TLC: 20% ethyl acetate-hexanes, $R_f$=0.79 (UV, CAM). $^1$H NMR (500 MHz, CDCl$_3$). δ: 7.49-7.45 (m, 2H), 7.38-7.37 (m, 3H), 6.06 (s, 1H), 5.09 (d, J=10.5 Hz, 1H), 3.61 (dd, J=8.5 Hz, J=3.5 Hz, 1H), 2.58 (s, 3H), 2.54 (dd, J=14.5 Hz, J=8.5 Hz, 2H), 2.16-2.12 (m, 1H), 2.07-1.99 (m, 2H), 1.92-1.89 (m, 3H), 1.81-1.68 (m, 2H), 1.47-1.41 (m, 1H), 1.33 (s, 3H), 1.03 (d, J=7.0 Hz, 3H), 0.98 (d, J 7.0 Hz, 3H), 0.95 (d, J=7.0 Hz, 3H). $^{13}$C NMR (500 MHz, CDCl$_3$) δ: 165.3, 156.1, 142.2, 129.1, 128.5, 126.3, 117.1, 85.6, 85.5, 70.7, 63.4, 48.2, 47.1, 38.6, 32.9, 31.2, 29.7, 24.8, 20.2, 18.2, 17.5, 17.0. FTIR (NaCl, thin film), cm$^{-1}$ 2927, 2855, 2094, 1717, 1626, 1270, 1162.

The following describes a preparation of compound 10.

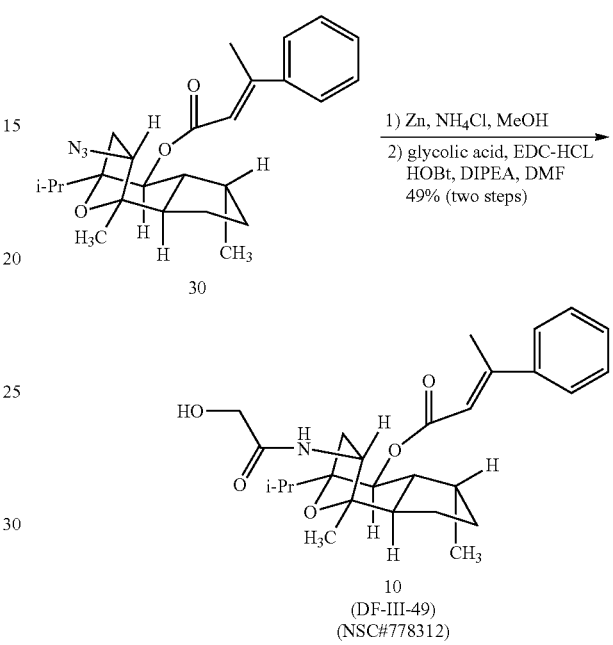

To prepare compound 10, ammonium chloride (16 mg, 0.31 mmol, 10 equiv) and zinc (dust, 20 mg, 0.31 mmol, 10 equiv) were added sequentially to a solution of 30 (13 mg, 31 μmol, 1.0 equiv) in methanol (3 mL). The reaction mixture was stirred vigorously at room temperature for 2 h, then was concentrated. The resulting residue was triturated with diethyl ether (3×10 mL) and the combined organic fractions were filtered through a pad of silica gel to afford the amine (8.0 mg, 66%), which was advanced without further purification. Glycolic acid (23 mg, 0.31 mmol, 10 equiv), N-(3-dimethylaminopropyl)-N'-ethylcarbodiimide hydrochloride (59 mg, 0.31 mmol, 10.0 equiv), and 1-hydroxybenzotriazole (41 mg, 0.31 mmol, 10 equiv) were added sequentially to a stirred solution of the amine intermediate in N,N-dimethylformamide (15 mL) at 23° C. The reaction mixture was cooled to 0° C. whereupon N,N-diisopropylamine (0.16 mL, 0.92 mmol, 30.0 equiv) was added. The reaction mixture was stirred at 0° C. for 1 h, then allowed to warm to 23° C. and stirred for an additional 18 h. The reaction mixture was quenched with 10% aqueous lithium chloride solution (20 mL), then extracted with dichloromethane (3×25 mL). The combined organic layers were dried over anhydrous sodium sulfate and the dried solution was concentrated. Purification of the residue by flash column chromatography (50% ethyl acetate-hexanes) afforded the glycolamide 10 (4.0 mg, 29% over two steps) as a colorless oil. Glycolamide 10 (DF-III-49, NSC#778312): TLC: 50% ethyl acetate-hexanes, $R_f$=0.35 (UV, CAM). FTIR (NaCl, thin film), cm$^{-1}$ 3397, 2965, 2925, 2854, 1717, 1653.

The following describes a preparation of compound 31.

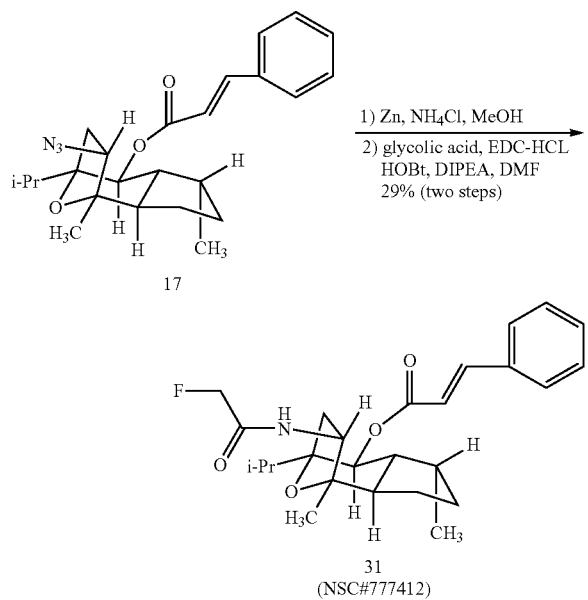

Ammonium chloride (26 mg, 0.49 mmol, 10 equiv) and zinc (dust, 32 mg, 0.49 mmol, 10 equiv) were added sequentially to a solution of 17 (20 mg, 49 µmol, 1.0 equiv) in methanol (3 mL). The reaction mixture was stirred vigorously at room temperature for 2 h, then was concentrated. The resulting residue was triturated with diethyl ether (3×10 mL) and the combined organic fractions were filtered through a pad of silica gel to afford the amine, which was advanced without further purification. Fluoroacetic acid (38 mg, 0.49 mmol, 10 equiv), N-(3-dimethylaminopropyl)-N′-ethylcarbodiimide hydrochloride (94 mg, 0.49 mmol, 10.0 equiv), and 1-hydroxybenzotriazole (66 mg, 0.49 mmol, 10 equiv) were added sequentially to a stirred solution of the amine intermediate in N,N-dimethylformamide (15 ml) at 23° C. The reaction mixture was cooled to 0° C. whereupon N,N-diisopropylamine (0.26 ml, 1.47 mmol, 30.0 equiv) was added. The reaction mixture was stirred at 0° C. for 1 h, then allowed to warm to 23° C. and stirred for an additional 18 h. The reaction mixture was quenched with 10% aqueous lithium chloride solution (20 ml), then extracted with dichloromethane (3×25 ml). The combined organic layers were dried over anhydrous sodium sulfate and the dried solution was concentrated. Purification of the residue by flash column chromatography (50% ethyl acetate-hexanes) afforded the glycolamide 31 (6.3 mg, 29% over two steps) as a colorless oil. Glycolamide 31 (NSC#771412): TLC: 20% ethyl acetate-hexanes, $R_f$=0.16 (UV, CAM). $^1$H NMR: (500 MHz, CDCl$_3$). δ: 7.66 (d, J=16.0 Hz, 1H), 7.54-7.52 (m, 2H), 7.40-7.38 (m, 3H), 6.40 (d, J=16.0 Hz, 1H), 6.30-6.28 (m, 1H), 5.15 (d, J=10.5 Hz, 1H), 4.87 (s, 1H), 4.78 (s, 1H), 4.51-4.46 (m, 1H), 2.73 (dd, J=14.5, 9.0, 1H), 2.17-2.13 (m, 1H), 1.97-1.93 (m, 1H), 1.90-1.78 (m, 2H), 1.75-1.63 (m, 2H), 1.38-1.29 (m, 2H), 1.27-1.23 (m, 5H), 1.19 (s, 3H), 1.03 (d, J=6.5 Hz, 3H), 0.97 (d, J=7.0 Hz, 3H), 0.94 (d, J=7.0 Hz, 3H). $^{13}$C NMR: (500 MHz, CDCl$^3$). δ: 179.5, 165.7, 145.2, 134.3, 130.4, 128.9, 128.1, 118.0, 85.2, 84.6, 71.4, 62.4, 50.7, 48.2, 46.7, 40.7, 33.2, 31.2, 29.7, 24.5, 19.9, 18.2, 17.5, 16.9. FTIR (NaCl, thin film), cm$^{-1}$ 2955, 2924, 1710, 1637, 1169. HRMS: APCI [M+H]$^+$ Calcd. for $C_{26}H_{34}FO_5$: 445.2385. Found: 445.2602.

EXAMPLE 2

This example demonstrates that compound 9 is orally bioavailable in mice, in accordance with an embodiment of the invention.

Mice were dosed at 5 mg/kg, 10 mg/kg, 50 mg/kg, and 100 mg/kg compound 9 in Labrasol vehicle via oral gavage. 30 minutes after dosing, plasma was assayed for the concentration of compound 9 using LC-MS. The results are depicted graphically in FIG. 5.

As is apparent from the results shown in FIG. 4, compound 9 was found in plasma in up to approximately 700 ng/mL of compound 9 after dosing at 100 mg/kg.

EXAMPLE 3

This example illustrates that compounds of the invention inhibit human cancer cell growth. Samples were tested in the standard National Cancer Institute 60-cell line protocol. First, they were tested against all 60 cell lines in a single final concentration of 10 micromolar. Then, they were separately tested in five 10-fold dilutions. The drug exposure was for two days, with an SRB endpoint. The results for the cell lines A498 (renal cancer), ACHN (renal cancer), and HS 578T (breast cancer) for both the one-dose protocol and as GI$_{50}$ values are set forth in Table 1.

TABLE 1

| Compound | A498 one dose (%) | A498 GI$_{50}$ (µM) | ACHN one dose (%) | ACHN GI$_{50}$ (µM) | HS 578T one dose (%) | HS 578T GI$_{50}$ (µM) |
| --- | --- | --- | --- | --- | --- | --- |
| 9 | −15.20 | 0.16 | 8.01 | 4.0 | 9.45 | 0.83 |
| 12 | −15.23 | 1.6 | 8.40 | 5.4 | −18.26 | 2.2 |
| 11 | 41.34 | 5.6 | 99.90 | 17 | 73.09 | 6.2 |
| 31 | 83.31 | — | 104.52 | — | 92.63 | — |
| 10 | −24.59 | 1.1 | 27.88 | 3.3 | −8.92 | 2.2 |

EXAMPLE 4

Figure 3A:
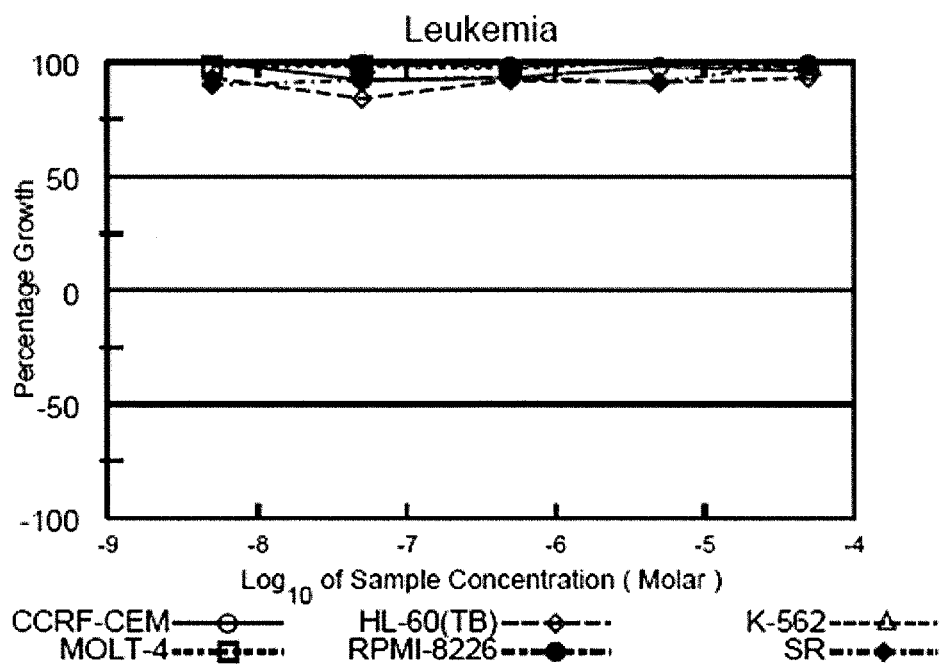
Figure 3B:
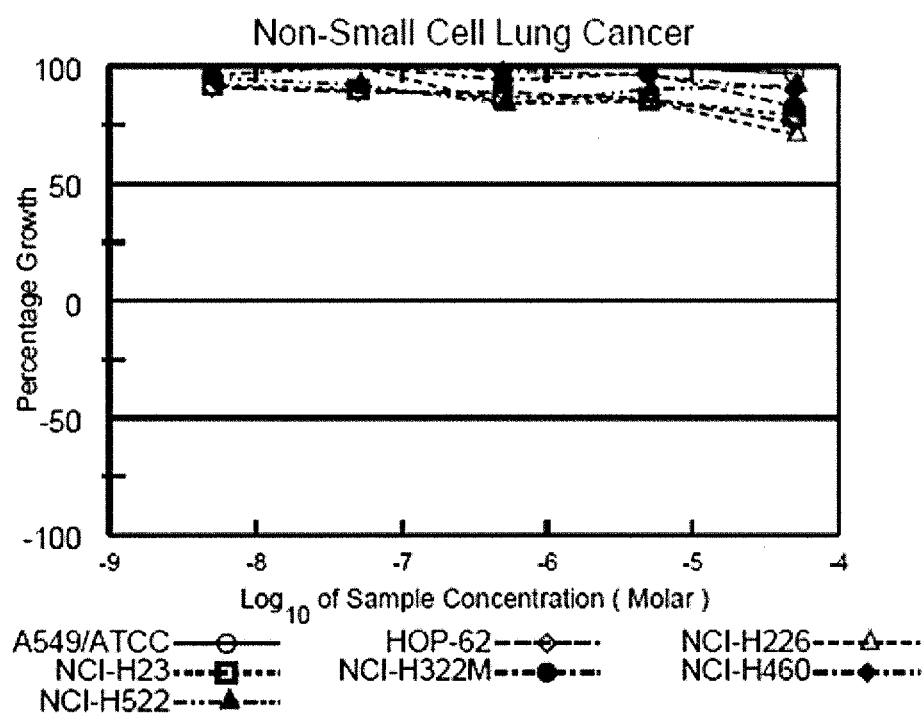
Figure 3C:
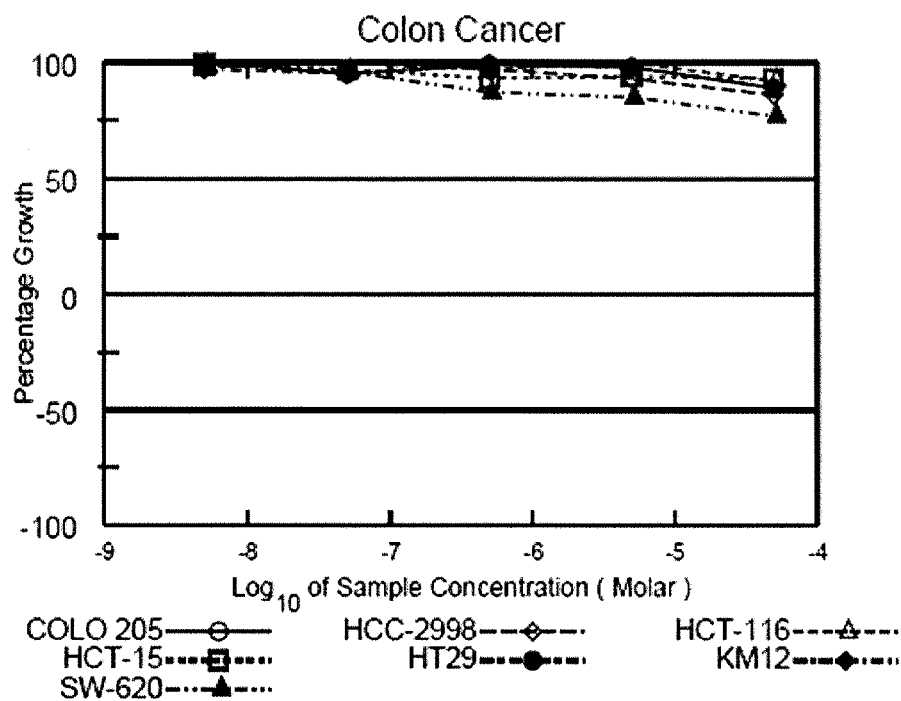
Figure 3D:
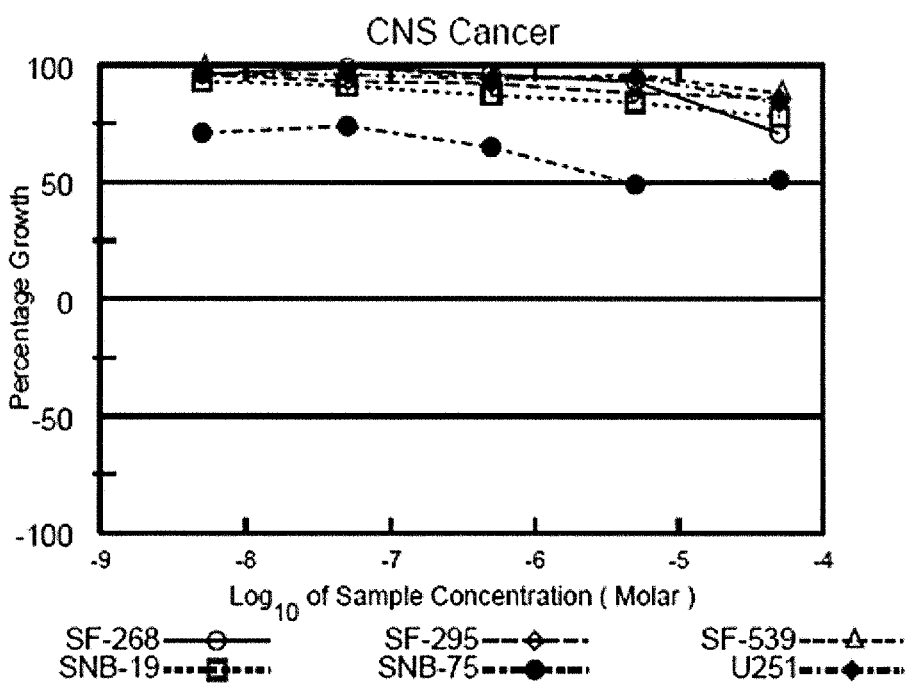
Figure 3E:
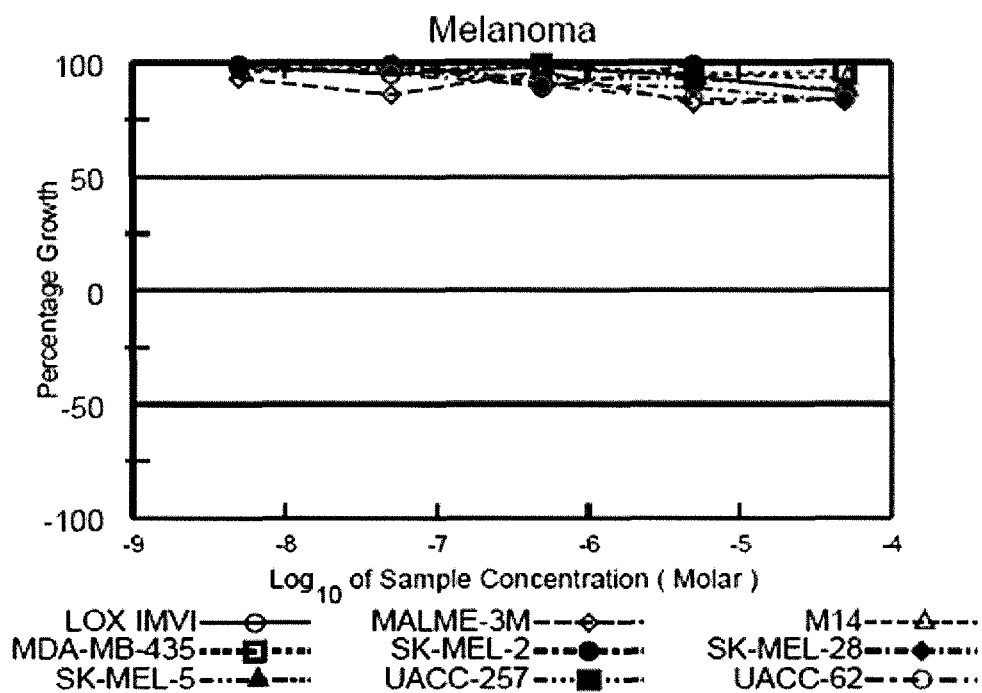
Figure 3F:
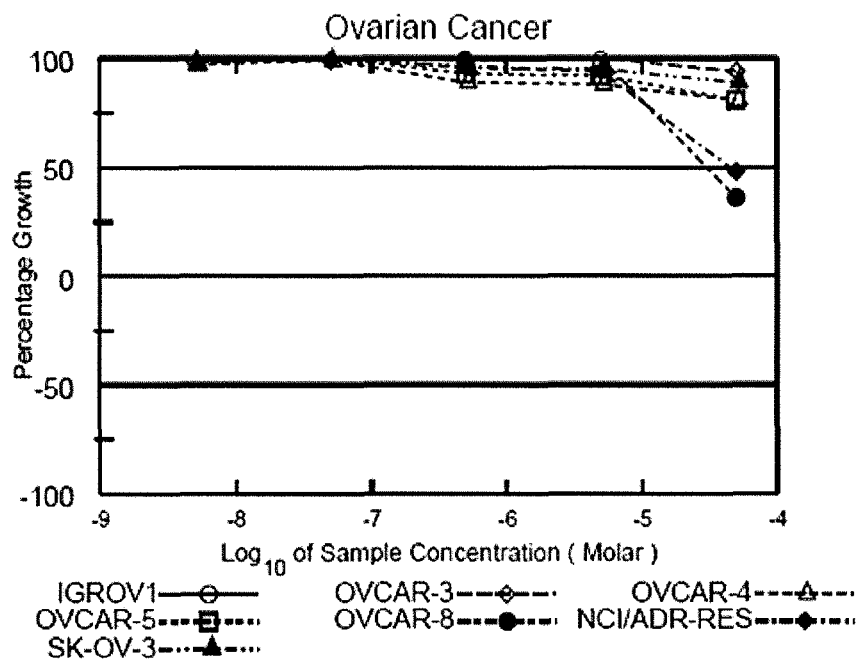
Figure 3G:
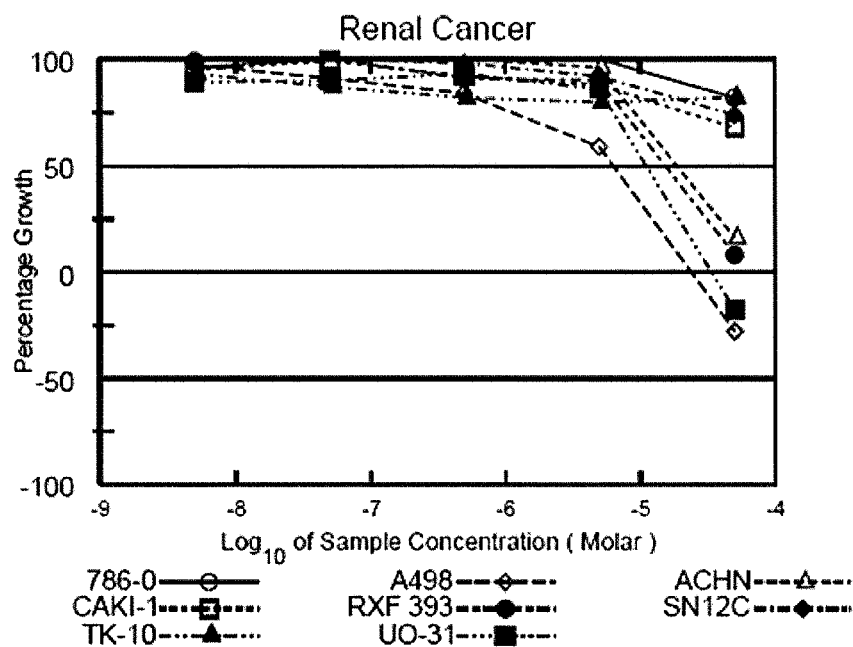
Figure 3H:
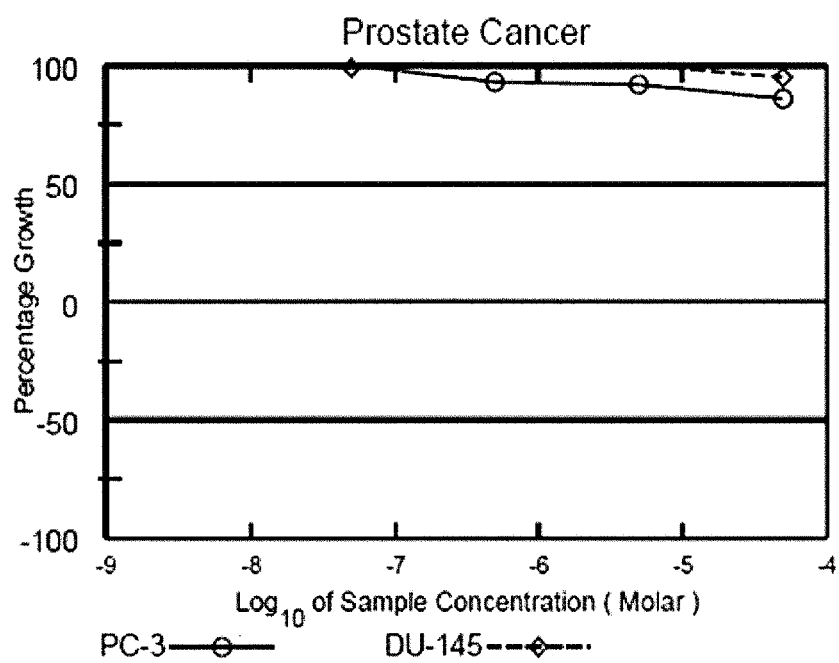
Figure 3I:
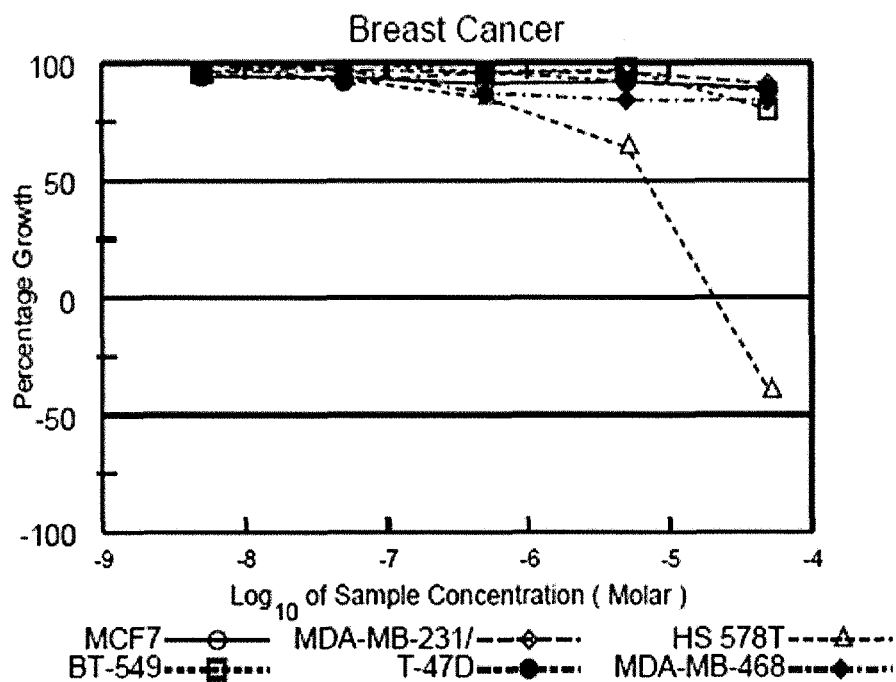
Figure 4A:
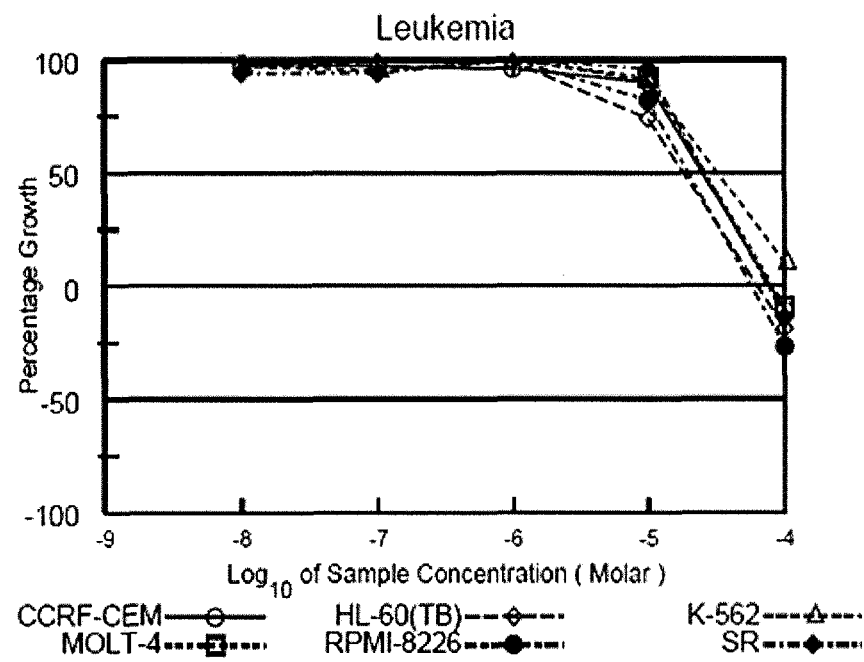
Figure 4B:
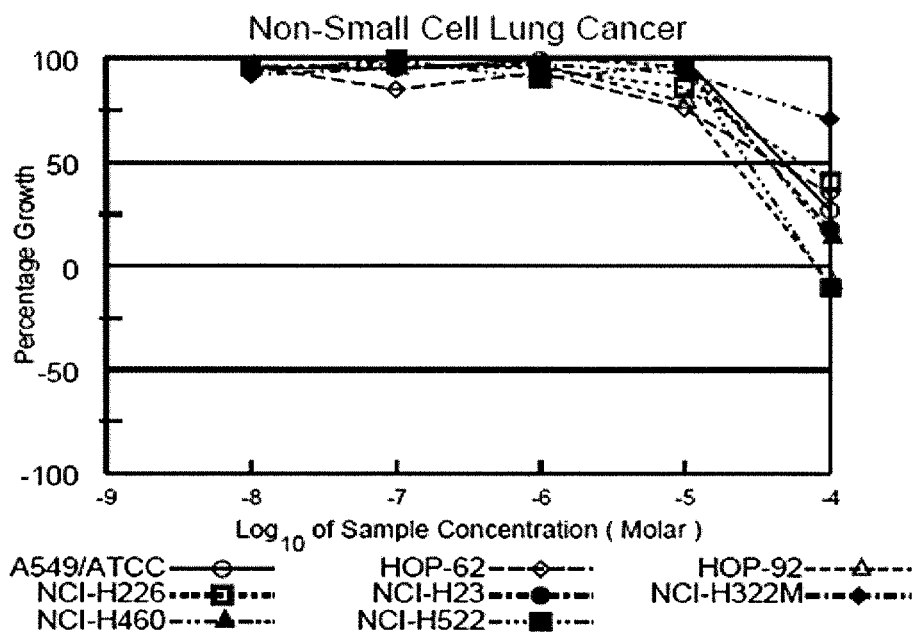
Figure 4C:
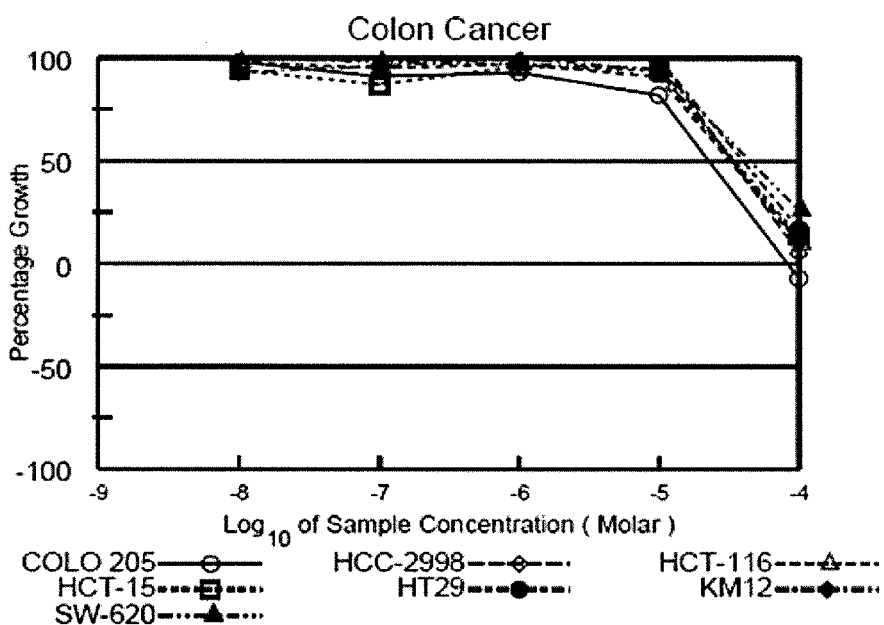
Figure 4D:
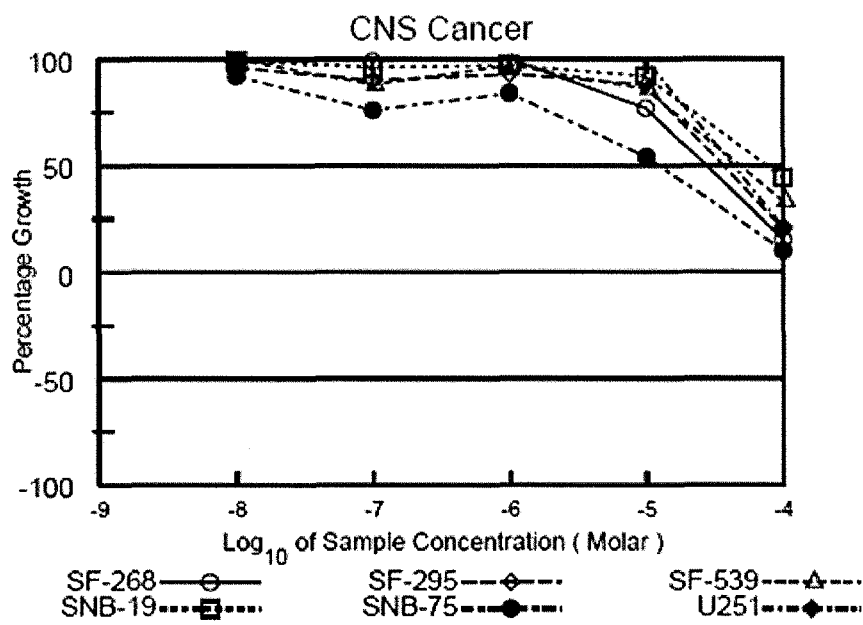
Figure 4E:
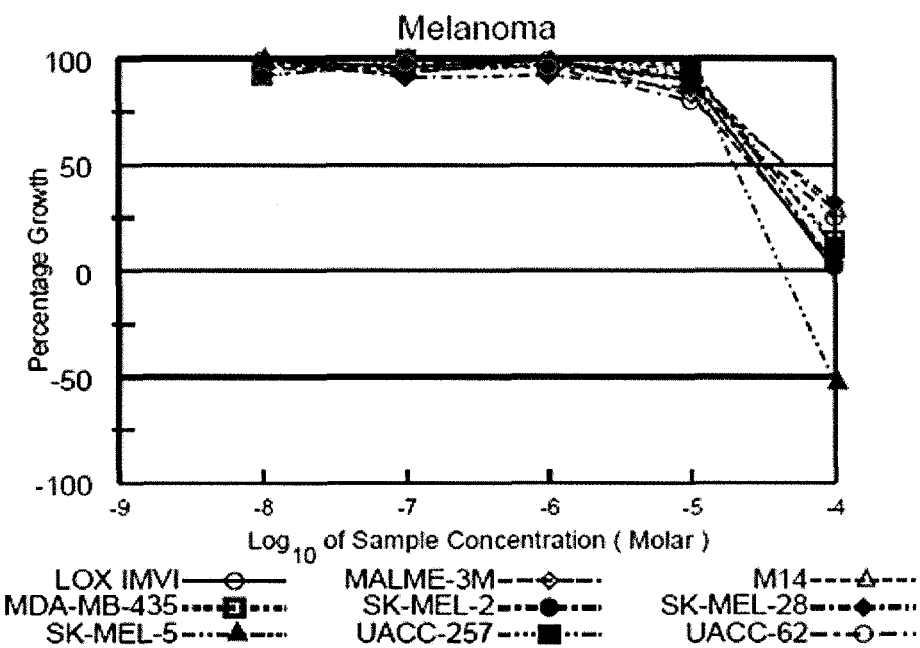
Figure 4F:
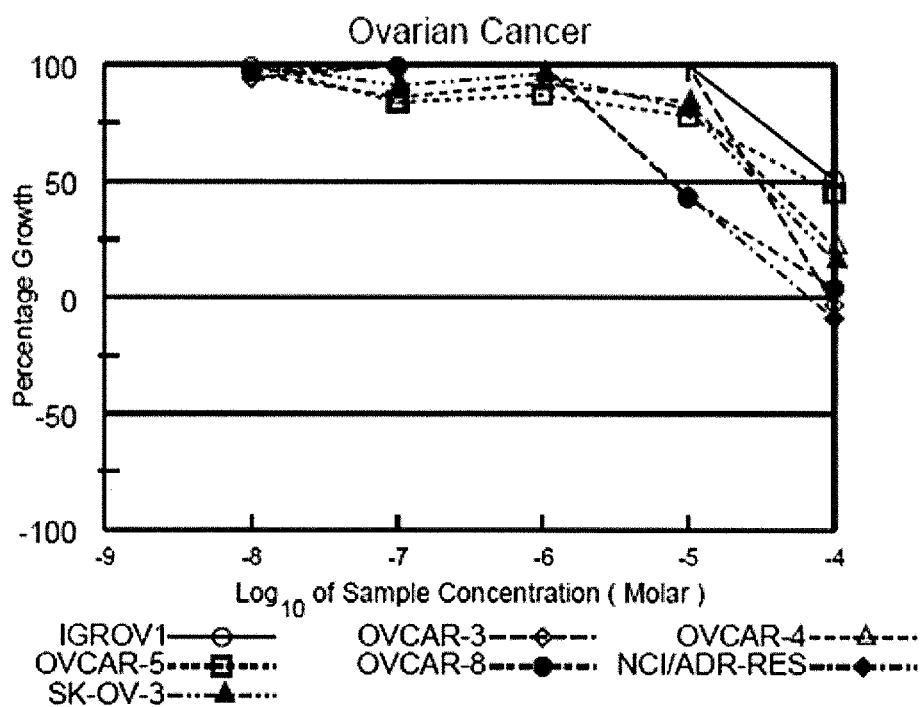
Figure 4G:
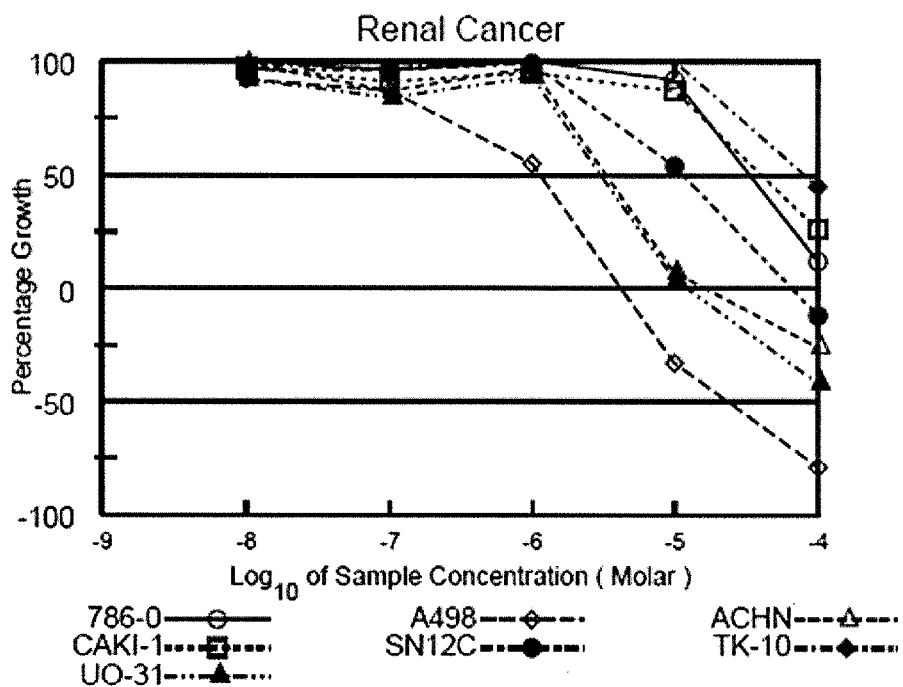
Figure 4H:
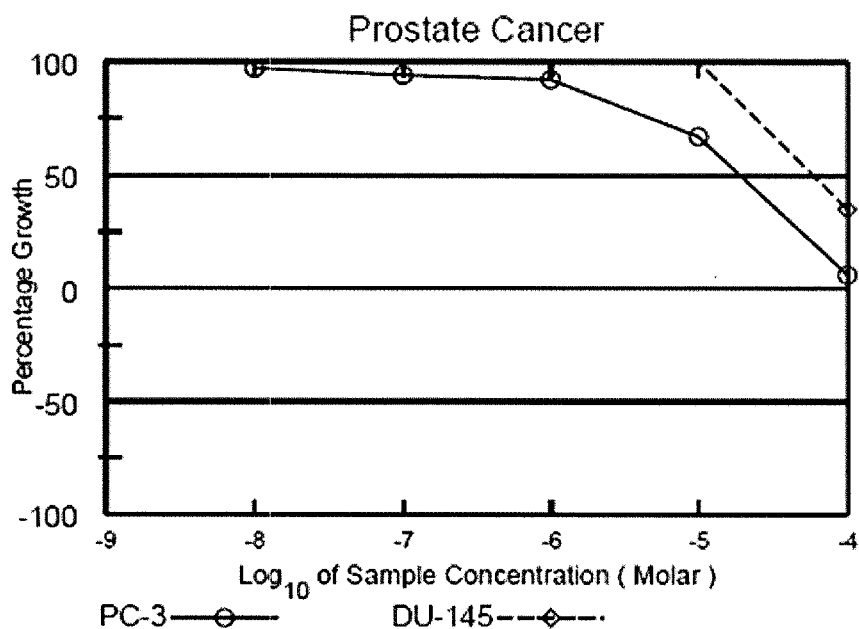
Figure 4I:
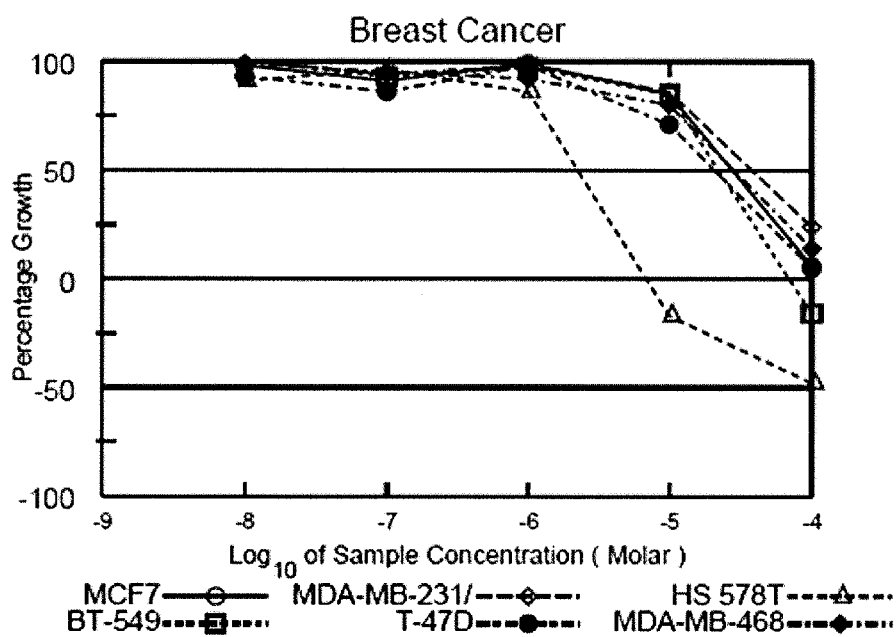

This example illustrates that compounds of the invention inhibit human cancer cell growth. Samples were tested in the standard National Cancer Institute 60-cell line protocol. First, they were tested against all 60 cell lines in a single final concentration of 10 micromolar. Then, they were separately tested in five 10-fold dilutions. The drug exposure was for two days, with an SRB endpoint. The results are depicted as dose-response curves are set forth in FIGS. 1A-1I for compound 9, FIGS. 2A-2I for compound 12, FIGS. 3A-3I for compound 11, and FIGS. 4A-3I for compound 10.

EXAMPLE 5

This example illustrates that compounds of the invention inhibit human cancer cell growth. Samples were tested in the standard National Cancer Institute 60-cell line protocol. The dosing protocol was a single dose of the compound at 10 μM concentration. The growth percent observed with compounds 31 and 10 are set forth in Tables 2 and 3, respectively.

TABLE 2

| Panel/Cell line | Growth Percent |
| --- | --- |
| Leukemia | |
| CCRF-CEM | 88.63 |
| HL-60(fB) | 104.52 |
| K-562 | 106.42 |
| MOLT-4 | 96.46 |
| RPMI-8226 | 94.34 |
| SA | 85.46 |
| Non-Small Cell Lung Cancer | |
| A549/ATCC | 94.42 |
| HOP-62 | 90.75 |
| HOP-92 | 75.85 |
| NCI-H226 | 84.54 |
| NCI-H23 | 101.57 |
| NCI-H322M | 97.44 |
| NCI-H460 | 103.56 |
| NCI-H522 | 102.51 |
| Colon Cancer | |
| COLO205 | 103.21 |
| HCC-2998 | 107.28 |
| HCT-116 | 87.42 |
| HCT-15 | 102.83 |
| HT29 | 108.62 |
| KM12 | 103.52 |
| SW-620 | 100.57 |
| CNS Cancer | |
| SF-268 | 97.74 |
| SF-295 | 104.84 |
| SF-539 | 87.89 |
| SNB-19 | 103.67 |
| SNB-75 | 87.93 |
| U251 | 105.6 |
| Melanoma | |
| LOX IMVI | 102.48 |
| MALME-3M | 106.46 |
| M14 | 96.67 |
| MDA-MB-435 | 106.48 |
| SK-MEL-2 | 116.95 |
| SK-MEL-28 | 109.79 |
| SK-MEL-5 | 110.24 |
| UACC-257 | 104.8 |
| UACC-62 | 99.56 |
| Ovarian Cancer | |
| IGROVI | 103.48 |
| OVCAR-3 | 114.72 |
| OVCAR-4 | 104.77 |
| OVCAR-5 | 101.93 |
| OVCAR-8 | 107.04 |
| NCI/ADR-RES | 98.53 |
| SK-OV-3 | 91.26 |
| Renal Cancer | |
| 786-0 | 97.31 |
| A498 | 83.31 |
| ACHN | 104.52 |
| CAKI-1 | 80.94 |
| SN12C | 103.21 |
| TK-10 | 104.2 |
| U031 | 91.08 |
| Prostate Cancer | |
| PC-3 | 83.98 |
| DU-145 | 114.9 |
| Breast Cancer | |
| MCF7 | 105.67 |
| MDA-MB-231/ATCC | 101.66 |
| HS 578T | 92.63 |
| BT-549 | 111.03 |
| T-470 | 78.42 |

TABLE 3

| Panel/Cell line | Growth Percent |
| --- | --- |
| Leukemia | |
| CCRF-CEM | 94.07 |
| K-562 | 92.32 |
| RPMI-8226 | 125.43 |
| SA | 117.13 |
| Non-Small Cell Lung Cancer | |
| A549/ATCC | 84.13 |
| HOP-62 | 97.57 |
| HOP-92 | 87.13 |
| NCI-H226 | 90.67 |
| NCI-H23 | 97.74 |
| NCI-H322M | 105.1 |
| NCI-H460 | 105.67 |
| NCI-H522 | 92.53 |
| Colon Cancer | |
| COLO205 | 107.4 |
| HCC-2998 | 103.84 |
| HCT-116 | 100.8 |
| HCT-15 | 99.96 |
| HT29 | 98.69 |
| KM12 | 111.83 |
| SW-620 | 103.14 |
| CNS Cancer | |
| SF-268 | 105.59 |
| SF-295 | 97.79 |
| SF-539 | 91.23 |
| SNB-19 | 108.35 |
| SNB-75 | 102.12 |
| U251 | 91.84 |
| Melanoma | |
| LOX IMVI | 100.2 |
| MALME-3M | 95.9 |
| M14 | 100.16 |
| MDA-MB-435 | 105.86 |
| SK-MEL-2 | 104.13 |
| SK-MEL-28 | 117.95 |
| SK-MEL-5 | 101.11 |
| UACC-257 | 92.39 |
| UACC-62 | 101.83 |
| Ovarian Cancer | |
| IGROVI | 104.22 |
| OVCAR-3 | 12076 |
| OVCAR-5 | 118.88 |
| OVCAR-8 | 61.25 |
| NCI/ADR-RES | 72.19 |
| SK-OV-3 | 109.87 |
| Renal Cancer | |
| 786-0 | 93.47 |
| A498 | −24.59 |
| ACHN | 27.88 |
| CAKI-1 | 99.02 |
| RXF 393 | 73.51 |

TABLE 3-continued

| Panel/Cell line | Growth Percent |
|---|---|
| SN12C | 84.62 |
| TK-10 | 109.09 |
| UO-31 | 17.49 |
| Prostate Cancer | |
| PC-3 | 83.12 |
| DU-145 | 118.84 |
| Breast Cancer | |
| MCF7 | 89.73 |
| MDA-MB-231/ATCC | 99.61 |
| HS 578T | −8.92 |
| BT-549 | 116.58 |
| T-47D | 89.34 |
| MDA-MB-468 | 101.49 |

EXAMPLE 6

This example demonstrates that compound 9 is orally bioavailable in mice, in accordance with an embodiment of the invention.

Ten mice were administered 50 mg/kg of compound 9 in Labrasol vehicle via oral gavage. Two mice at a time were sacrificed at the following time points: 5 min, 15 min, 1 h, 4 h, and 8 h. Plasma concentrations of compound 9 were measured by LC-MS/MS, and the results set forth in Table 4 and depicted graphically in FIG. 7.

TABLE 4

| Animal | Time (hr) | [Aza-Englerin] (ng/mL) | Mean |
|---|---|---|---|
| 1 | 0.0833 | 6.87 | 10.04 |
| 2 | 0.0833 | 13.20 | |
| 3 | 0.2500 | 22.76 | 40.73 |
| 4 | 0.2500 | 58.70 | |
| 5 | 1.0000 | 87.16 | 73.20 |
| 6 | 1.0000 | 59.24 | |
| 7 | 4.0000 | 31.12 | 58.97 |
| 8 | 4.0000 | 86.81 | |
| 9 | 8.0000 | 87.28 | 67.75 |
| 10 | 8.0000 | 48.21 | |

It was subsequently discovered that an error was made in weighing out compound 9 for formulation of a 5 mg/mL solution in Labrasol. The underweight formulation was confirmed to be about 40% of the expected concentration.

The $AUC_{LAST}$ was calculated as 524.4 hr*ng/mL (SE=97.3 hr*ng/mL).

Figure 7:
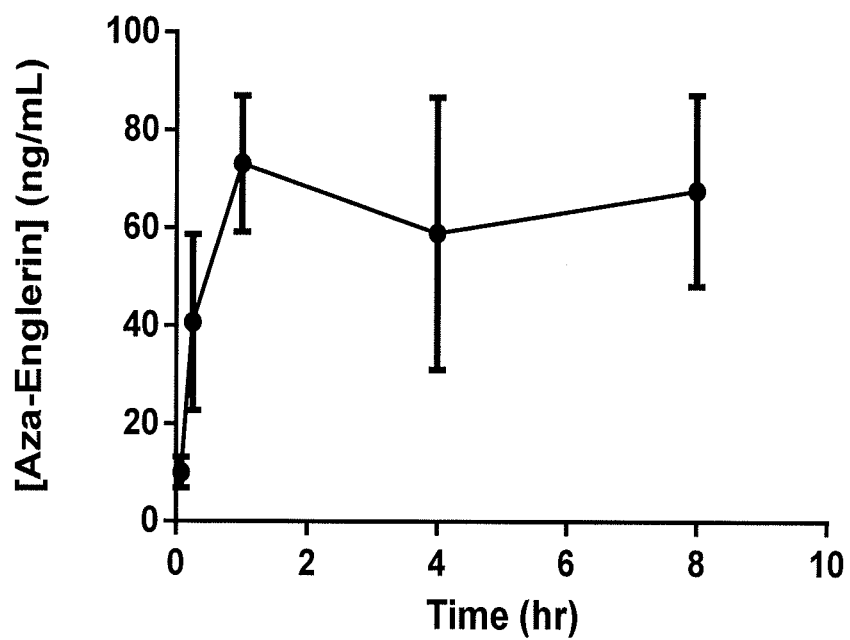
FIG. 7 depicts the plasma concentration of compound 9 in mice as a function of time after oral gavage of about 20 mg/kg the compound.

As is apparent from the results set forth in Table 4 and the graphical results depicted in FIG. 7, compound 9 is rapidly absorbed and the plasma concentrations of compound 9 are sustained for greater than 8 h.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I) or formula (II):

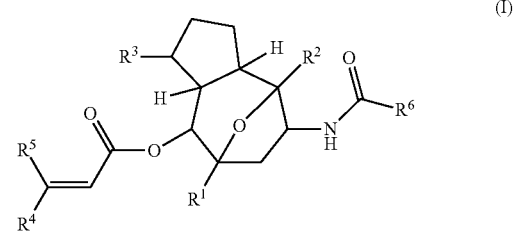

(I)

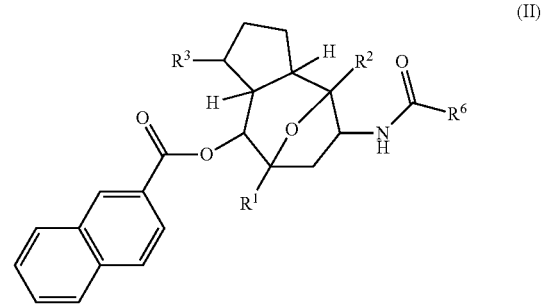

(II)

or an epimer thereof, wherein
$R^1$ is isopropyl or isopropylenyl,
$R^2$ and $R^3$ are independently $C_1$-$C_6$ alkyl,
$R^4$ is $C_6$-$C_{10}$ aryl or $C_3$-$C_8$ cycloalkyl, wherein the aryl is optionally substituted with $C_1$-$C_6$ alkyl, $C_1$-$C_6$ hydroxyalkyl, $C_1$-$C_6$ alkoxy, halo, or nitro,
$R^5$ is hydrogen or $C_1$-$C_6$ alkyl, and
$R^6$ is $C_1$-$C_6$ alkyl, hydroxy $C_1$-$C_6$ alkyl, or fluoro $C_1$-$C_6$ alkyl.

2. The compound or epimer of claim 1, wherein the compound is of formula (I), and $R^6$ is hydroxy $C_1$-$C_6$ alkyl or fluoro $C_1$-$C_6$ alkyl.

3. The compound or epimer of claim 2, which is

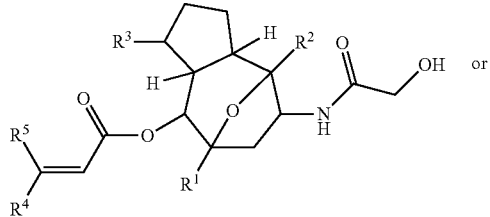

or

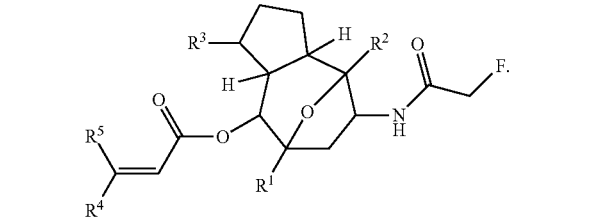

4. The compound or epimer of claim 2, wherein $R^4$ is phenyl and $R^5$ is hydrogen or methyl.

5. The compound or epimer of claim 4, wherein the compound is

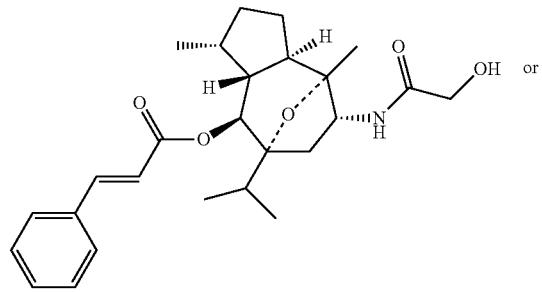

or

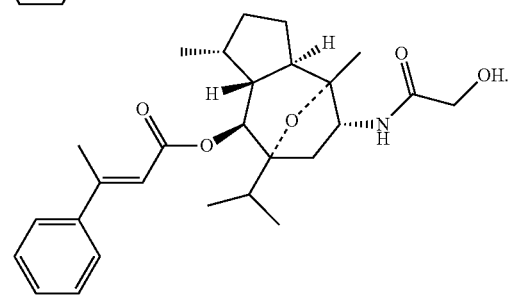

6. The compound or epimer of claim 2, wherein $R^4$ is $C_3$-$C_8$ cycloalkyl and $R^5$ is hydrogen.

7. The compound or epimer of claim 6, wherein the compound is

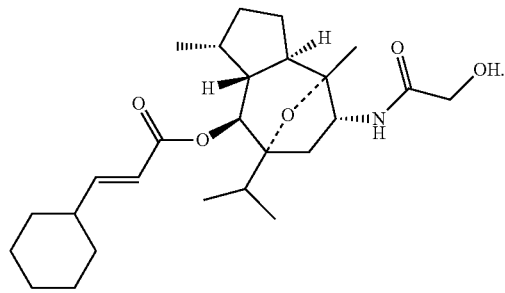 [SMILES: CC(C)[C@@]12C[C@@H](NC(=O)CO)[C@@](C)(O1)[C@@H]1CC[C@@H](C)[C@H]1[C@@H]2OC(=O)/C=C/C1CCCCC1]

8. The compound or epimer of claim 1, wherein the compound is of formula (II) and $R^6$ is hydroxy $C_1$-$C_6$ alkyl or fluoro $C_1$-$C_6$ alkyl.

9. The compound or epimer of claim 8, wherein the compound is

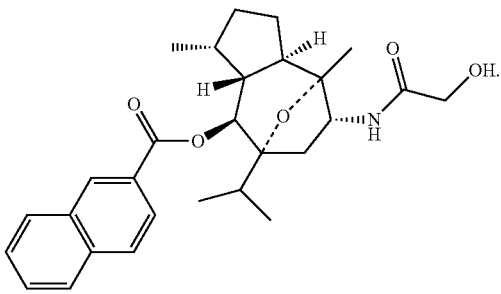 [SMILES: CC(C)[C@@]12C[C@@H](NC(=O)CO)[C@@](C)(O1)[C@@H]1CC[C@@H](C)[C@H]1[C@@H]2OC(=O)c1ccc2ccccc2c1]

10. A pharmaceutical composition comprising a pharmaceutically acceptable carrier and a compound or epimer of claim 1.

11. A method of treating cancer in a mammal comprising administering to the animal an effective amount of a compound or epimer of claim 1, wherein the cancer is selected from the group consisting of leukemia, non-small cell lung cancer, colon cancer, melanoma, prostate cancer, kidney cancer, breast cancer, CNS cancer, Ewing's sarcoma, and ovarian cancer.

12. The method of 11, wherein the compound or epimer is orally administered to the mammal.

13. A method for the synthesis of a compound of formula A:

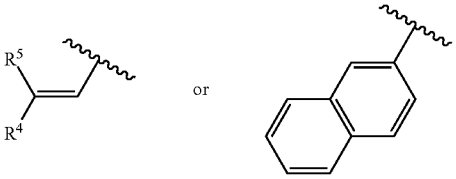

wherein R is

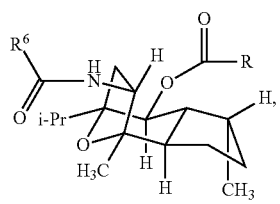

$R^4$ is $C_6$-$C_{10}$ aryl or $C_3$-$C_8$ cycloalkyl, wherein the aryl is optionally substituted with $C_1$-$C_6$ alkyl, $C_1$-$C_6$ hydroxyalkyl, $C_1$-$C_6$ alkoxy, halo, or nitro, $R^5$ is hydrogen or $C_1$-$C_6$ alkyl, and wherein $R^6$ is $C_1$-$C_6$ alkyl, hydroxy $C_1$-$C_6$ alkyl, or fluoro $C_1$-$C_6$ alkyl, comprising the steps of:
providing a compound of formula B:

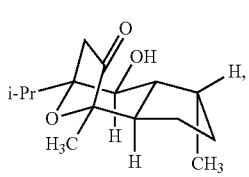

acylating compound B to provide compound C:

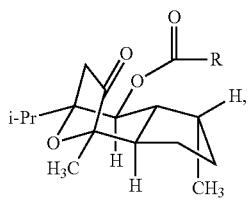

reducing compound C to provide compound D:

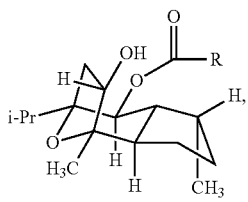

converting the hydroxyl group of compound D to a leaving group to provide compound E:

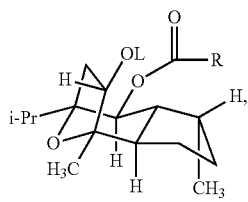

reacting compound E with an azide compound to provide compound F:

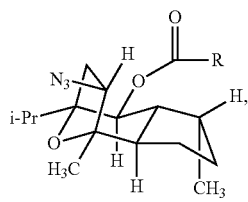

reducing the azido group of compound F to provide compound G:

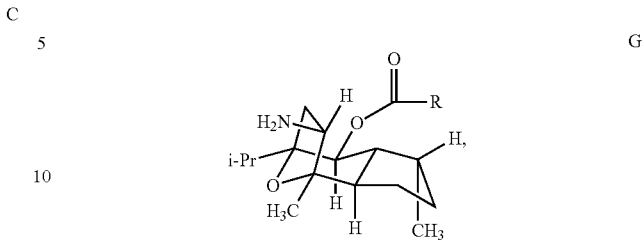

and acylating the amino group of compound G to provide compound A.

14. A method of treating an animal for a disease or condition associated with insulin resistance comprising administering to the animal an effective amount of a compound or epimer of claim 1, wherein the disease or condition associated with insulin resistance is diabetes, type 2 diabetes, obesity, inflammation, metabolic syndrome, polycystic ovary disease, arteriosclerosis, non-alcoholic fatty liver disease, reproductive abnormality in a female, and growth abnormality.

15. A method of activating transcriptional activity of heat shock factor 1 (HSF1) or inducing the expression of heat shock protein 70 (HSP70) in an animal in need thereof comprising administering to the animal an effective amount of a compound or epimer of claim 1.

16. A method of treating an HIV-infected animal or an HTLV-infected animal comprising co-administering to the animal an effective amount of a compound or epimer of claim 1 and at least one antiviral agent.

17. A method of increasing the activity of latent infected CD4+ cells of an animal carrying HIV comprising administering to the animal an effective amount of a compound or epimer of claim 1.

18. A method of inhibiting Treg activation and number in an animal carrying HTLV comprising administering to the animal an effective amount of a compound or epimer of claim 1.

19. A method of decreasing Glut1 expression in an ATL cell in an animal carrying HTLV comprising administering to the animal an effective amount of a compound or epimer of claim 1.

20. A pharmaceutical composition comprising a compound of claim 1 and at least one anti-retroviral agent.

* * * * *